US012805879B2

(12) United States Patent
Perler et al.

(10) Patent No.: US 12,805,879 B2
(45) Date of Patent: Nov. 24, 2026

(54) PATIENT-SPECIFIC SURGICAL METHODS AND INSTRUMENTATION

(71) Applicant: Treace Medical Concepts, Inc., Ponte Vedra, FL (US)

(72) Inventors: Adam D. Perler, St. Petersberg, FL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 156 days.

(21) Appl. No.: 18/753,735

(22) Filed: Jun. 25, 2024

(65) Prior Publication Data

US 2024/0341773 A1 Oct. 17, 2024

Related U.S. Application Data

(63) Continuation of application No. 17/681,674, filed on Feb. 25, 2022, now Pat. No. 12,490,992, which is a (Continued)

(51) Int. Cl.
*A61B 17/15* (2006.01)
*A61B 17/56* (2006.01)
*A61B 34/10* (2016.01)

(52) U.S. Cl.
CPC ............ *A61B 17/152* (2013.01); *A61B 17/56* (2013.01); *A61B 34/10* (2016.02); (Continued)

(58) Field of Classification Search
CPC ........ A61B 34/10; A61B 17/15; A61B 17/152; A61B 17/151; A61B 17/80; (Continued)

(56) References Cited

U.S. PATENT DOCUMENTS

| | | | |
|---|---|---|---|
| 3,664,022 | A | 5/1972 | Small |
| 4,069,824 | A | 1/1978 | Weinstock |

(Continued)

FOREIGN PATENT DOCUMENTS

| | | | |
|---|---|---|---|
| AU | 2009227957 | B2 | 7/2014 |
| AU | 2009222469 | B2 | 2/2015 |

(Continued)

OTHER PUBLICATIONS

Hunt et al., "Locked Versus Nonlocked Plate Fixation For Hallux MTP Arthrodesis," Foot and Ankle International, vol. 32, No. 7, Jul. 2011, pp. 704-709.

(Continued)

*Primary Examiner* — Christopher J Beccia
(74) *Attorney, Agent, or Firm* — Fredrikson & Byron, P.A.

(57) ABSTRACT

A patient specific instrument is disclosed for correcting a condition present in a patient. The patient specific instrument includes a body that includes an inferior side having a bone engagement surface shaped to match a first surface of a first bone and a second surface of a second bone of a joint. The instrument also includes a superior side having a first guide feature and a second guide feature that together, with the bone engagement surface overlying the first surface and the second surface, are positioned to guide resection of the first bone and the second bone during a surgical osteotomy for correcting the condition. The body is configured to seat transverse to the joint with the bone engagement surface engaging the first surface of the first bone and the second surface of the second bone.

20 Claims, 43 Drawing Sheets

Related U.S. Application Data continuation-in-part of application No. 17/020,630, filed on Sep. 14, 2020, now Pat. No. 11,931,106.

(60) Provisional application No. 62/900,294, filed on Sep. 13, 2019, provisional application No. 63/190,551, filed on May 19, 2021, provisional application No. 63/224,344, filed on Jul. 21, 2021.

(52) U.S. Cl.
CPC ... *A61B 2017/568* (2013.01); *A61B 2034/105* (2016.02); *A61B 2034/108* (2016.02)

(58) Field of Classification Search
CPC . A61B 17/8061; A61B 17/8095; A61B 17/17; A61B 17/1775; A61B 17/56; A61B 17/66; A61B 17/88; A61B 17/8863
See application file for complete search history.

(56) References Cited

U.S. PATENT DOCUMENTS

| | | | |
|---|---|---|---|
| 4,159,716 | A | 7/1979 | Borchers |
| 4,187,840 | A | 2/1980 | Watanabe |
| 4,335,715 | A | 6/1982 | Kirkley |
| 4,338,927 | A | 7/1982 | Volkov et al. |
| 4,349,018 | A | 9/1982 | Chambers |
| 4,409,973 | A | 10/1983 | Neufeld |
| 4,436,684 | A | 3/1984 | White |
| 4,440,168 | A | 4/1984 | Warren |
| 4,509,511 | A | 4/1985 | Neufeld |
| 4,565,191 | A | 1/1986 | Slocum |
| 4,570,624 | A | 2/1986 | Wu |
| 4,628,919 | A | 12/1986 | Clyburn |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,839,822 | A | 6/1989 | Dormond et al. |
| 4,895,141 | A | 1/1990 | Koeneman et al. |
| 4,959,066 | A | 9/1990 | Dunn et al. |
| 4,978,347 | A | 12/1990 | Ilizarov |
| 4,988,349 | A | 1/1991 | Pennig |
| 4,995,875 | A | 2/1991 | Coes |
| 5,049,149 | A | 9/1991 | Schmidt |
| 5,053,039 | A | 10/1991 | Hofmann et al. |
| 5,112,334 | A | 5/1992 | Alchermes et al. |
| 5,147,364 | A | 9/1992 | Comparetto |
| 5,171,244 | A | 12/1992 | Caspari et al. |
| 5,176,685 | A | 1/1993 | Rayhack |
| 5,207,676 | A | 5/1993 | Canadell et al. |
| 5,254,119 | A | 10/1993 | Schreiber |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,417,694 | A | 5/1995 | Marik et al. |
| 5,449,360 | A | 9/1995 | Schreiber |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,613,969 | A | 3/1997 | Jenkins, Jr. |
| 5,620,442 | A | 4/1997 | Bailey et al. |
| 5,643,270 | A | 7/1997 | Combs |
| 5,662,656 | A | 9/1997 | White |
| 5,667,510 | A | 9/1997 | Combs |
| H1706 | H | 1/1998 | Mason |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,788,695 | A | 8/1998 | Richardson |
| 5,803,924 | A | 9/1998 | Oni et al. |
| 5,810,822 | A | 9/1998 | Mortier |
| 5,836,950 | A | 11/1998 | Hansson |
| 5,839,438 | A | 11/1998 | Graettinger et al. |
| 5,843,085 | A | 12/1998 | Graser |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| 5,957,927 | A | 9/1999 | Magee et al. |
| 5,980,526 | A | 11/1999 | Johnson et al. |
| 5,984,931 | A | 11/1999 | Greenfield |
| 6,007,535 | A | 12/1999 | Rayhack et al. |
| 6,030,391 | A | 2/2000 | Brainard et al. |
| 6,162,223 | A | 12/2000 | Orsak et al. |
| 6,171,309 | B1 | 1/2001 | Huebner |
| 6,203,545 | B1 | 3/2001 | Stoffella |
| 6,248,109 | B1 | 6/2001 | Stoffella |
| 6,391,031 | B1 | 5/2002 | Toomey |
| 6,416,465 | B2 | 7/2002 | Brau |
| 6,478,799 | B1 | 11/2002 | Williamson |
| 6,511,481 | B2 | 1/2003 | Von Hoffmann et al. |
| 6,676,662 | B1 | 1/2004 | Bagga et al. |
| 6,712,824 | B2 | 3/2004 | Millard et al. |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,780,190 | B2 | 8/2004 | Maroney |
| 6,796,986 | B2 | 9/2004 | Duffner |
| 6,859,661 | B2 | 2/2005 | Tuke |
| 6,944,518 | B2 | 9/2005 | Roose |
| 6,964,645 | B1 | 11/2005 | Smits |
| 7,033,361 | B2 | 4/2006 | Collazo |
| 7,097,647 | B2 | 8/2006 | Segler |
| 7,153,310 | B2 | 12/2006 | Ralph et al. |
| 7,182,766 | B1 | 2/2007 | Mogul |
| 7,241,298 | B2 | 7/2007 | Nemec et al. |
| 7,282,054 | B2 | 10/2007 | Steffensmeier et al. |
| 7,351,203 | B2 | 4/2008 | Jelliffe et al. |
| 7,377,924 | B2 | 5/2008 | Raistrick et al. |
| 7,465,303 | B2 | 12/2008 | Riccione et al. |
| 7,473,255 | B2 | 1/2009 | Mcgarity et al. |
| 7,540,874 | B2 | 6/2009 | Trumble et al. |
| 7,572,258 | B2 | 8/2009 | Stiernborg |
| 7,641,660 | B2 | 1/2010 | Lakin et al. |
| D610,257 | S | 2/2010 | Horton |
| 7,670,345 | B2 | 3/2010 | Plassky et al. |
| 7,686,811 | B2 | 3/2010 | Byrd et al. |
| 7,691,108 | B2 | 4/2010 | Lavallee |
| 7,763,026 | B2 | 7/2010 | Egger et al. |
| 7,789,885 | B2 | 9/2010 | Metzger |
| D629,900 | S | 12/2010 | Fisher |
| 7,875,058 | B2 | 1/2011 | Holmes, Jr. |
| 7,972,338 | B2 | 7/2011 | O'Brien |
| 7,983,777 | B2 | 7/2011 | Melton et al. |
| D646,389 | S | 10/2011 | Claypool et al. |
| 8,057,473 | B2 | 11/2011 | Orsak et al. |
| 8,057,478 | B2 | 11/2011 | Kuczynski et al. |
| D651,315 | S | 12/2011 | Bertoni et al. |
| D651,316 | S | 12/2011 | May et al. |
| 8,080,010 | B2 | 12/2011 | Schulz et al. |
| 8,080,045 | B2 | 12/2011 | Wotton, III |
| 8,114,087 | B2 | 2/2012 | Long et al. |
| 8,123,753 | B2 | 2/2012 | Poncet |
| 8,147,530 | B2 | 4/2012 | Strnad et al. |
| 8,167,918 | B2 | 5/2012 | Strnad et al. |
| 8,172,848 | B2 | 5/2012 | Tomko et al. |
| 8,187,280 | B2 | 5/2012 | May et al. |
| 8,192,441 | B2 | 6/2012 | Collazo |
| 8,197,487 | B2 | 6/2012 | Poncet et al. |
| 8,206,153 | B2 | 6/2012 | Suttin et al. |
| 8,231,623 | B1 | 7/2012 | Jordan |
| 8,231,663 | B2 | 7/2012 | Kay et al. |
| 8,246,561 | B1 | 8/2012 | Agee et al. |
| 8,246,680 | B2 | 8/2012 | Betz et al. |
| D666,721 | S | 9/2012 | Wright et al. |
| 8,262,664 | B2 | 9/2012 | Justin et al. |
| 8,262,665 | B2 | 9/2012 | Massoud |

(56) References Cited

U.S. PATENT DOCUMENTS

| | | | |
|---|---|---|---|
| 8,277,455 | B2 | 10/2012 | Couture et al. |
| 8,282,644 | B2 | 10/2012 | Edwards |
| 8,282,645 | B2 | 10/2012 | Lawrence et al. |
| 8,287,541 | B2 | 10/2012 | Nelson et al. |
| 8,292,966 | B2 | 10/2012 | Morton |
| 8,303,596 | B2 | 11/2012 | Plaky et al. |
| 8,323,281 | B2 | 12/2012 | Hotchkiss et al. |
| 8,323,289 | B2 | 12/2012 | Re |
| 8,357,111 | B2 | 1/2013 | Caillouette et al. |
| 8,377,105 | B2 | 2/2013 | Bscher |
| 8,388,690 | B2 | 3/2013 | Singhatat et al. |
| D679,395 | S | 4/2013 | Wright et al. |
| 8,435,246 | B2 | 5/2013 | Fisher et al. |
| 8,475,462 | B2 | 7/2013 | Thomas et al. |
| 8,484,001 | B2 | 7/2013 | Glozman et al. |
| 8,518,045 | B2 | 8/2013 | Szanto |
| 8,523,870 | B2 | 9/2013 | Green, II et al. |
| 8,529,568 | B2 | 9/2013 | Bouadi |
| 8,532,807 | B2 | 9/2013 | Metzger |
| 8,551,106 | B2 | 10/2013 | Harrold |
| D694,884 | S | 12/2013 | Mooradian et al. |
| D695,402 | S | 12/2013 | Dacosta et al. |
| 8,641,721 | B2 | 2/2014 | Aram et al. |
| 8,652,142 | B2 | 2/2014 | Geissler |
| 8,657,820 | B2 | 2/2014 | Kubiak et al. |
| D701,303 | S | 3/2014 | Cook |
| 8,663,234 | B2 | 3/2014 | Grimm et al. |
| 8,668,700 | B2 | 3/2014 | Catanzarite et al. |
| 8,685,030 | B2 | 4/2014 | Gtte et al. |
| 8,696,719 | B2 | 4/2014 | Lofthouse et al. |
| 8,702,686 | B2 | 4/2014 | Geebelen et al. |
| 8,702,712 | B2 | 4/2014 | Jordan et al. |
| 8,715,289 | B2 | 5/2014 | Smith |
| 8,715,363 | B2 | 5/2014 | Ratron et al. |
| 8,728,084 | B2 | 5/2014 | Berelsman et al. |
| 8,758,354 | B2 | 6/2014 | Habegger et al. |
| 8,777,948 | B2 | 7/2014 | Bernsteiner |
| 8,784,457 | B2 | 7/2014 | Graham |
| 8,795,286 | B2 | 8/2014 | Sand et al. |
| 8,808,298 | B2 | 8/2014 | Raub et al. |
| 8,808,301 | B1 | 8/2014 | Nofsinger |
| 8,808,302 | B2 | 8/2014 | Roose et al. |
| 8,828,012 | B2 | 9/2014 | May et al. |
| 8,838,263 | B2 | 9/2014 | Sivak et al. |
| 8,858,602 | B2 | 10/2014 | Weiner et al. |
| 8,864,773 | B2 | 10/2014 | Paul et al. |
| 8,882,778 | B2 | 11/2014 | Ranft |
| 8,882,816 | B2 | 11/2014 | Kartalian et al. |
| 8,892,235 | B2 | 11/2014 | Choi et al. |
| 8,898,043 | B2 | 11/2014 | Ashby et al. |
| D720,456 | S | 12/2014 | Dacosta et al. |
| 8,900,247 | B2 | 12/2014 | Tseng et al. |
| 8,911,444 | B2 | 12/2014 | Bailey |
| 8,920,428 | B2 | 12/2014 | Zakaria et al. |
| 8,926,612 | B2 | 1/2015 | Graham |
| 8,932,299 | B2 | 1/2015 | Bono et al. |
| 8,939,982 | B2 | 1/2015 | Chellaoui |
| 8,939,984 | B2 | 1/2015 | Budoff |
| 8,945,132 | B2 | 2/2015 | Play et al. |
| 8,965,075 | B2 | 2/2015 | Arnaud et al. |
| 8,974,460 | B2 | 3/2015 | De La Fuente et al. |
| 8,979,856 | B2 | 3/2015 | Catanzarite et al. |
| 8,992,531 | B2 | 3/2015 | Chow et al. |
| 8,992,532 | B2 | 3/2015 | Wong |
| 8,998,903 | B2 | 4/2015 | Price et al. |
| 8,998,904 | B2 | 4/2015 | Zeetser et al. |
| 8,998,907 | B2 | 4/2015 | Myers |
| 8,998,909 | B2 | 4/2015 | Gillman et al. |
| 9,005,207 | B2 | 4/2015 | Dodds et al. |
| 9,011,451 | B2 | 4/2015 | Long et al. |
| 9,011,452 | B2 | 4/2015 | Iannotti et al. |
| 9,011,456 | B2 | 4/2015 | Ranawat et al. |
| 9,014,835 | B2 | 4/2015 | Azernikov et al. |
| 9,017,329 | B2 | 4/2015 | Tyber et al. |
| 9,017,336 | B2 | 4/2015 | Park et al. |
| 9,023,052 | B2 | 5/2015 | Lietz et al. |
| 9,044,250 | B2 | 6/2015 | Olsen et al. |
| 9,060,788 | B2 | 6/2015 | Bollinger |
| 9,060,822 | B2 | 6/2015 | Wright et al. |
| 9,089,376 | B2 | 7/2015 | Medoff et al. |
| 9,101,421 | B2 | 8/2015 | Blacklidge |
| 9,107,715 | B2 | 8/2015 | Blitz et al. |
| 9,113,915 | B2 | 8/2015 | Thomas et al. |
| 9,113,957 | B2 | 8/2015 | Axelson, Jr. et al. |
| 9,138,237 | B2 | 9/2015 | Meade et al. |
| 9,138,332 | B2 | 9/2015 | Harris et al. |
| D740,424 | S | 10/2015 | Dacosta et al. |
| 9,173,665 | B2 | 11/2015 | Couture |
| 9,173,691 | B2 | 11/2015 | Orbay et al. |
| 9,186,154 | B2 | 11/2015 | Li |
| 9,186,160 | B1 | 11/2015 | Song |
| 9,198,678 | B2 | 12/2015 | Frey et al. |
| 9,204,897 | B2 | 12/2015 | Jones et al. |
| 9,211,128 | B2 | 12/2015 | Gillman et al. |
| 9,220,509 | B2 | 12/2015 | Boyer et al. |
| 9,220,518 | B2 | 12/2015 | Neal et al. |
| 9,220,519 | B2 | 12/2015 | Kaneyama et al. |
| 9,220,551 | B2 | 12/2015 | Waizenegger |
| 9,232,951 | B2 | 1/2016 | Johannaber |
| 9,232,955 | B2 | 1/2016 | Bonin, Jr. et al. |
| 9,254,155 | B2 | 2/2016 | Iannotti et al. |
| 9,295,497 | B2 | 3/2016 | Schoenefeld et al. |
| 9,301,768 | B2 | 4/2016 | Buza et al. |
| 9,301,783 | B2 | 4/2016 | Gerold et al. |
| 9,308,006 | B2 | 4/2016 | Martin et al. |
| 9,308,037 | B2 | 4/2016 | Richter et al. |
| 9,320,609 | B2 | 4/2016 | Schon et al. |
| 9,345,497 | B2 | 5/2016 | Gonzalvez et al. |
| 9,351,738 | B2 | 5/2016 | Aram et al. |
| 9,351,743 | B2 | 5/2016 | Kehres et al. |
| 9,370,380 | B2 | 6/2016 | Riccione |
| 9,375,220 | B2 | 6/2016 | Horan et al. |
| 9,402,636 | B2 | 8/2016 | Collazo |
| 9,402,640 | B2 | 8/2016 | Reynolds et al. |
| 9,408,641 | B2 | 8/2016 | Zhang et al. |
| 9,414,846 | B2 | 8/2016 | Gillman et al. |
| 9,414,847 | B2 | 8/2016 | Kurtz |
| 9,414,877 | B2 | 8/2016 | Helenbolt et al. |
| 9,421,021 | B2 | 8/2016 | Keppler |
| 9,427,240 | B2 | 8/2016 | Von Zabern et al. |
| D765,844 | S | 9/2016 | Dacosta |
| D766,434 | S | 9/2016 | Dacosta |
| D766,437 | S | 9/2016 | Dacosta |
| D766,438 | S | 9/2016 | Dacosta |
| D766,439 | S | 9/2016 | Dacosta |
| 9,433,452 | B2 | 9/2016 | Weiner et al. |
| 9,445,823 | B2 | 9/2016 | Harris et al. |
| 9,452,050 | B2 | 9/2016 | Miles et al. |
| 9,456,902 | B2 | 10/2016 | Hacking et al. |
| 9,463,034 | B2 | 10/2016 | Wong et al. |
| 9,492,182 | B2 | 11/2016 | Keefer |
| 9,517,145 | B2 | 12/2016 | Meridew et al. |
| 9,522,023 | B2 | 12/2016 | Haddad et al. |
| 9,526,514 | B2 | 12/2016 | Kelley et al. |
| 9,545,276 | B2 | 1/2017 | Buchanan et al. |
| 9,561,041 | B2 | 2/2017 | Snider et al. |
| 9,566,103 | B2 | 2/2017 | Mayer |
| 9,579,106 | B2 | 2/2017 | Lo et al. |
| 9,579,107 | B2 | 2/2017 | Schoenefeld |
| 9,579,112 | B2 | 2/2017 | Catanzarite et al. |
| 9,592,084 | B2 | 3/2017 | Grant |
| 9,603,605 | B2 | 3/2017 | Collazo |
| 9,603,640 | B2 | 3/2017 | Palmer et al. |
| 9,622,820 | B2 | 4/2017 | Baloch et al. |
| 9,629,726 | B2 | 4/2017 | Reiley et al. |
| 9,652,889 | B2 | 5/2017 | Young et al. |
| 9,662,220 | B2 | 5/2017 | Warburton |
| 9,668,746 | B2 | 6/2017 | Lee et al. |
| 9,675,471 | B2 | 6/2017 | Bojarski et al. |
| 9,687,261 | B2 | 6/2017 | Serbousek et al. |
| 9,693,787 | B2 | 7/2017 | Ammann et al. |
| 9,693,878 | B2 | 7/2017 | Kunz et al. |
| 9,700,433 | B2 | 7/2017 | Myers |
| 9,713,484 | B2 | 7/2017 | Sammarco |

(56) References Cited

U.S. PATENT DOCUMENTS

| | | | |
|---|---|---|---|
| 9,737,311 | B2 | 8/2017 | Lavallee et al. |
| 9,737,367 | B2 | 8/2017 | Steines et al. |
| 9,750,538 | B2 | 9/2017 | Soffiatti et al. |
| 9,785,747 | B2 | 10/2017 | Geebelen |
| 9,788,958 | B2 | 10/2017 | Melamed et al. |
| 9,788,975 | B2 | 10/2017 | Li |
| 9,795,392 | B2 | 10/2017 | Zajac |
| 9,795,394 | B2 | 10/2017 | Bonutti |
| 9,814,474 | B2 | 11/2017 | Montoya et al. |
| 9,820,868 | B2 | 11/2017 | Witt et al. |
| 9,826,981 | B2 | 11/2017 | Schoenefeld et al. |
| 9,839,438 | B2 | 12/2017 | Eash |
| 9,848,929 | B2 | 12/2017 | Dacosta et al. |
| 9,849,019 | B2 | 12/2017 | Miller et al. |
| 9,877,754 | B2 | 1/2018 | Patel et al. |
| 9,883,954 | B1 | 2/2018 | Murphy |
| 9,888,931 | B2 | 2/2018 | Bake |
| 9,888,950 | B2 | 2/2018 | Perez et al. |
| 9,918,658 | B2 | 3/2018 | Mccaulley et al. |
| 9,918,769 | B2 | 3/2018 | Provencher et al. |
| 9,925,049 | B2 | 3/2018 | Goldstein et al. |
| 9,925,068 | B2 | 3/2018 | Bays et al. |
| 9,956,089 | B2 | 5/2018 | Kelman et al. |
| 9,968,456 | B2 | 5/2018 | Song |
| 9,980,760 | B2 | 5/2018 | Dacosta et al. |
| 9,987,092 | B2 | 6/2018 | Hladio et al. |
| 9,990,765 | B2 | 6/2018 | Ju et al. |
| 9,993,256 | B2 | 6/2018 | Lipman et al. |
| 10,002,227 | B2 | 6/2018 | Netravali et al. |
| 10,004,516 | B2 | 6/2018 | Johannaber |
| 10,010,431 | B2 | 7/2018 | Eraly et al. |
| 10,016,177 | B2 | 7/2018 | Aram et al. |
| 10,022,170 | B2 | 7/2018 | Leemrijse et al. |
| 10,028,756 | B2 | 7/2018 | Liu |
| 10,034,753 | B2 | 7/2018 | Dressler et al. |
| 10,052,114 | B2 | 8/2018 | Keppler et al. |
| 10,055,536 | B2 | 8/2018 | Maes et al. |
| 10,058,335 | B2 | 8/2018 | Lee et al. |
| 10,089,413 | B2 | 10/2018 | Wirx-Speetjens et al. |
| 10,098,761 | B2 | 10/2018 | Sherman et al. |
| 10,105,145 | B2 | 10/2018 | Lavallee |
| 10,123,807 | B2 | 11/2018 | Geebelen |
| 10,130,378 | B2 | 11/2018 | Bryan |
| 10,149,722 | B2 | 12/2018 | Aram et al. |
| 10,159,480 | B2 | 12/2018 | Tuten |
| 10,159,499 | B2 | 12/2018 | Dacosta et al. |
| 10,159,512 | B2 | 12/2018 | Robinson |
| 10,201,357 | B2 | 2/2019 | Aram et al. |
| 10,206,692 | B2 | 2/2019 | Sanders |
| 10,217,530 | B2 | 2/2019 | Couture et al. |
| 10,219,812 | B2 | 3/2019 | Torrie et al. |
| 10,226,292 | B2 | 3/2019 | Lundquist et al. |
| 10,231,745 | B2 | 3/2019 | Geebelen et al. |
| 10,238,382 | B2 | 3/2019 | Terrill et al. |
| 10,251,654 | B2 | 4/2019 | Fritzinger |
| 10,251,690 | B2 | 4/2019 | Katrana et al. |
| 10,262,084 | B2 | 4/2019 | Lavallee et al. |
| 10,265,080 | B2 | 4/2019 | Hughes et al. |
| 10,271,886 | B2 | 4/2019 | Abiven |
| 10,278,713 | B2 | 5/2019 | Richter et al. |
| 10,282,488 | B2 | 5/2019 | Eash |
| 10,286,197 | B2 | 5/2019 | Pouliot et al. |
| 10,325,065 | B2 | 6/2019 | Li et al. |
| 10,327,829 | B2 | 6/2019 | Dacosta et al. |
| 10,342,529 | B2 | 7/2019 | Fallin et al. |
| 10,350,022 | B2 | 7/2019 | Jansen et al. |
| 10,357,261 | B2 | 7/2019 | Kugler et al. |
| 10,357,299 | B2 | 7/2019 | Weiner et al. |
| 10,363,052 | B2 | 7/2019 | Park et al. |
| 10,398,510 | B2 | 9/2019 | Goto |
| 10,420,613 | B2 | 9/2019 | Azevedo Da Silva et al. |
| 10,456,205 | B2 | 10/2019 | Meridew et al. |
| 10,512,470 | B1 | 12/2019 | Bays et al. |
| 10,524,808 | B1 | 1/2020 | Hissong et al. |
| 10,524,845 | B2 | 1/2020 | Orsak et al. |
| 10,537,392 | B2 | 1/2020 | Millahn et al. |
| 10,543,100 | B2 | 1/2020 | Couture et al. |
| 10,548,667 | B2 | 2/2020 | Flett et al. |
| 10,548,668 | B2 | 2/2020 | Furrer et al. |
| 10,582,969 | B2 | 3/2020 | Couture et al. |
| 10,610,241 | B2 | 4/2020 | Wagner et al. |
| 10,631,878 | B2 | 4/2020 | Fritzinger |
| 10,631,902 | B2 | 4/2020 | Weiner et al. |
| 10,653,432 | B2 | 5/2020 | Luttrell et al. |
| 10,653,464 | B2 | 5/2020 | Hill et al. |
| 10,653,467 | B2 | 5/2020 | Brumfield et al. |
| 10,675,096 | B2 | 6/2020 | Utz et al. |
| 10,682,147 | B2 | 6/2020 | Grant et al. |
| 10,709,567 | B2 | 7/2020 | Welker et al. |
| 10,716,581 | B2 | 7/2020 | Fritzinger et al. |
| 10,722,309 | B2 | 7/2020 | Gillman |
| 10,722,310 | B2 | 7/2020 | Luby |
| 10,779,867 | B2 | 9/2020 | Penzimer et al. |
| 10,779,890 | B2 | 9/2020 | Weir |
| 10,786,291 | B2 | 9/2020 | Weiner et al. |
| 10,792,081 | B2 | 10/2020 | Weiner et al. |
| 10,806,469 | B2 | 10/2020 | Fiechter et al. |
| 10,849,665 | B2 | 12/2020 | Singh et al. |
| 10,849,670 | B2 | 12/2020 | Santrock et al. |
| 10,856,891 | B2 | 12/2020 | Rhodes et al. |
| 10,856,925 | B1 | 12/2020 | Pontell |
| 10,869,722 | B2 | 12/2020 | Caldwell et al. |
| 10,874,408 | B2 | 12/2020 | Couture |
| 10,881,416 | B2 | 1/2021 | Couture et al. |
| 10,881,417 | B2 | 1/2021 | Mahfouz |
| 10,888,340 | B2 | 1/2021 | Awtrey et al. |
| 10,905,444 | B2 | 2/2021 | Siccardi et al. |
| 10,912,574 | B2 | 2/2021 | Kim et al. |
| 10,925,622 | B2 | 2/2021 | Kehres et al. |
| 10,939,926 | B2 | 3/2021 | Kam et al. |
| 10,939,939 | B1 | 3/2021 | Gil et al. |
| 10,973,529 | B2 | 4/2021 | Lavallee et al. |
| 11,000,327 | B2 | 5/2021 | Schlotterback et al. |
| 11,020,128 | B2 | 6/2021 | Guilloux et al. |
| 11,033,336 | B2 | 6/2021 | Bohl |
| 11,065,011 | B2 | 7/2021 | Bake et al. |
| 11,074,688 | B2 | 7/2021 | Chabin et al. |
| 11,090,069 | B2 | 8/2021 | Park |
| 11,090,161 | B2 | 8/2021 | Hodorek |
| 11,112,770 | B2 | 9/2021 | Roh et al. |
| 11,116,518 | B2 | 9/2021 | Hafez |
| 11,129,625 | B2 | 9/2021 | Song et al. |
| 11,129,678 | B2 | 9/2021 | Park |
| 11,154,362 | B2 | 10/2021 | Kim et al. |
| 11,158,047 | B2 | 10/2021 | Shah |
| 11,160,567 | B2 | 11/2021 | Fallin et al. |
| 11,160,568 | B1 | 11/2021 | Park |
| 11,166,732 | B2 | 11/2021 | Maxson et al. |
| 11,172,945 | B1 | 11/2021 | Lian |
| 11,179,165 | B2 | 11/2021 | Schoenefeld |
| 11,179,168 | B2 | 11/2021 | Dacosta et al. |
| 11,207,134 | B2 | 12/2021 | Hafez |
| 11,213,305 | B2 | 1/2022 | Iannotti et al. |
| 11,213,406 | B2 | 1/2022 | Rodriguez et al. |
| 11,219,526 | B2 | 1/2022 | Mahfouz |
| 11,224,448 | B2 | 1/2022 | Bailey |
| 11,259,817 | B2 | 3/2022 | Fallin et al. |
| 11,284,909 | B2 | 3/2022 | Castricini et al. |
| 11,304,705 | B2 | 4/2022 | Fallin et al. |
| 11,304,735 | B2 | 4/2022 | Sayger et al. |
| 11,324,522 | B2 | 5/2022 | Metzger et al. |
| 11,324,607 | B2 | 5/2022 | Mauldin et al. |
| 11,331,148 | B2 | 5/2022 | Fritzinger |
| 11,331,205 | B2 | 5/2022 | Parr |
| 11,344,347 | B2 | 5/2022 | Treace et al. |
| 11,389,221 | B2 | 7/2022 | Tyber et al. |
| 11,399,849 | B2 | 8/2022 | Larche et al. |
| 11,419,726 | B2 | 8/2022 | Miller et al. |
| 11,426,184 | B2 | 8/2022 | Rivet-Sabourin et al. |
| 11,432,931 | B2 | 9/2022 | Lang |
| 11,436,801 | B2 | 9/2022 | Haslam et al. |
| 11,439,412 | B2 | 9/2022 | Woodard et al. |
| 11,457,980 | B2 | 10/2022 | Bonny et al. |
| 11,484,354 | B2 | 11/2022 | Singh et al. |

(56) References Cited

U.S. PATENT DOCUMENTS

| | | | |
|---|---|---|---|
| 11,497,557 | B2 | 11/2022 | Haslam et al. |
| 11,508,102 | B2 | 11/2022 | Su et al. |
| 11,510,738 | B2 | 11/2022 | Stifter et al. |
| 11,532,402 | B2 | 12/2022 | Farley et al. |
| 11,557,036 | B2 | 1/2023 | Mansi et al. |
| 11,571,312 | B1 | 2/2023 | Parekh et al. |
| 11,583,298 | B2 | 2/2023 | Robichaud et al. |
| 11,596,421 | B2 | 3/2023 | Saltzman et al. |
| 11,596,443 | B2 | 3/2023 | Treace et al. |
| 11,602,386 | B2 | 3/2023 | Smith et al. |
| 11,607,250 | B2 | 3/2023 | Treace et al. |
| 11,627,954 | B2 | 4/2023 | May et al. |
| 11,628,003 | B2 | 4/2023 | Nachtrab et al. |
| 11,633,195 | B2 | 4/2023 | Dhillon |
| 11,648,019 | B2 | 5/2023 | Bays et al. |
| 11,653,938 | B2 | 5/2023 | Siegler |
| 11,684,423 | B2 | 6/2023 | Jaramaz et al. |
| 11,690,725 | B2 | 7/2023 | Gemon et al. |
| 11,717,359 | B2 | 8/2023 | Chi |
| 11,741,277 | B2 | 8/2023 | Dayal et al. |
| 11,751,892 | B2 | 9/2023 | Woodard et al. |
| 11,756,051 | B2 | 9/2023 | Indani et al. |
| 11,766,268 | B2 | 9/2023 | Iannotti et al. |
| 11,779,467 | B2 | 10/2023 | Mimnaugh et al. |
| 11,786,257 | B2 | 10/2023 | Dayton et al. |
| 11,793,549 | B2 | 10/2023 | Rhodes et al. |
| 11,812,978 | B2 | 11/2023 | Trabish et al. |
| 11,819,223 | B2 | 11/2023 | Lee |
| 11,819,224 | B2 | 11/2023 | Allard et al. |
| 11,849,933 | B2 | 12/2023 | Denham et al. |
| 11,849,957 | B2 | 12/2023 | Couture et al. |
| 11,849,961 | B2 | 12/2023 | Khatibi et al. |
| 11,849,962 | B2 | 12/2023 | Singh et al. |
| 11,854,683 | B2 | 12/2023 | Casey et al. |
| D1,011,524 | S | 1/2024 | Santrock et al. |
| 11,857,206 | B2 | 1/2024 | Robichaud et al. |
| 11,864,778 | B2 | 1/2024 | Mcginley et al. |
| 11,864,959 | B2 | 1/2024 | Basta |
| 11,911,046 | B2 | 2/2024 | Carroll et al. |
| 11,925,417 | B2 | 3/2024 | Mosnier et al. |
| 11,931,106 | B2 | 3/2024 | Perler et al. |
| 11,944,546 | B2 | 4/2024 | Puncreobutr et al. |
| 11,950,786 | B2 | 4/2024 | Courtis et al. |
| 11,963,687 | B2 | 4/2024 | Langhorn et al. |
| 11,963,703 | B2 | 4/2024 | Dayton et al. |
| 11,963,729 | B2 | 4/2024 | Aljuri et al. |
| 11,980,377 | B2 | 5/2024 | Mauldin et al. |
| 12,004,789 | B2 | 6/2024 | Mcaleer et al. |
| 12,004,814 | B2 | 6/2024 | Ryan et al. |
| D1,034,985 | S | 7/2024 | Hartson et al. |
| 12,035,929 | B2 | 7/2024 | Athwal et al. |
| 12,045,943 | B2 | 7/2024 | Chaoui et al. |
| 12,048,600 | B2 | 7/2024 | Azernikov et al. |
| 12,050,999 | B2 | 7/2024 | Poltaretskyi et al. |
| 12,053,242 | B2 | 8/2024 | Landon et al. |
| 12,062,183 | B2 | 8/2024 | Chaoui et al. |
| 12,097,129 | B2 | 9/2024 | Deransart et al. |
| 12,115,083 | B2 | 10/2024 | Mullen et al. |
| 12,121,272 | B2 | 10/2024 | Marien et al. |
| 2002/0107519 | A1 | 8/2002 | Dixon et al. |
| 2003/0236522 | A1 | 12/2003 | Long et al. |
| 2004/0010259 | A1 | 1/2004 | Keller et al. |
| 2004/0039394 | A1 | 2/2004 | Conti et al. |
| 2004/0039396 | A1 | 2/2004 | Couture et al. |
| 2004/0097946 | A1 | 5/2004 | Dietzel et al. |
| 2004/0138669 | A1 | 7/2004 | Horn |
| 2005/0059978 | A1 | 3/2005 | Sherry et al. |
| 2005/0080424 | A1 | 4/2005 | Cuckler et al. |
| 2005/0267482 | A1 | 12/2005 | Hyde |
| 2005/0273112 | A1 | 12/2005 | Mcnamara |
| 2006/0129163 | A1 | 6/2006 | Mcguire |
| 2006/0206044 | A1 | 9/2006 | Simon |
| 2006/0229621 | A1 | 10/2006 | Cadmus |
| 2006/0241607 | A1 | 10/2006 | Myerson et al. |
| 2006/0241608 | A1 | 10/2006 | Myerson et al. |
| 2006/0264961 | A1 | 11/2006 | Murray-Brown |
| 2007/0010818 | A1 | 1/2007 | Stone et al. |
| 2007/0123857 | A1 | 5/2007 | Deffenbaugh et al. |
| 2007/0233138 | A1 | 10/2007 | Figueroa et al. |
| 2007/0265634 | A1 | 11/2007 | Weinstein |
| 2007/0276383 | A1 | 11/2007 | Rayhack |
| 2008/0009863 | A1 | 1/2008 | Bond et al. |
| 2008/0039850 | A1 | 2/2008 | Rowley et al. |
| 2008/0091197 | A1 | 4/2008 | Coughlin |
| 2008/0140081 | A1 | 6/2008 | Heavener et al. |
| 2008/0161815 | A1 | 7/2008 | Schoenefeld et al. |
| 2008/0172054 | A1 | 7/2008 | Claypool et al. |
| 2008/0288004 | A1 | 11/2008 | Schendel |
| 2009/0036931 | A1 | 2/2009 | Pech et al. |
| 2009/0089081 | A1 | 4/2009 | Haddad |
| 2009/0093849 | A1 | 4/2009 | Grabowski |
| 2009/0099567 | A1 | 4/2009 | Zajac |
| 2009/0105767 | A1 | 4/2009 | Reiley |
| 2009/0198244 | A1 | 8/2009 | Leibel |
| 2009/0216089 | A1 | 8/2009 | Davidson |
| 2009/0222047 | A1 | 9/2009 | Graham |
| 2009/0254092 | A1 | 10/2009 | Albiol Llorach |
| 2009/0254126 | A1 | 10/2009 | Orbay et al. |
| 2009/0265012 | A1 | 10/2009 | Engh et al. |
| 2009/0287309 | A1 | 11/2009 | Walch et al. |
| 2010/0069910 | A1 | 3/2010 | Hasselman |
| 2010/0130981 | A1 | 5/2010 | Richards |
| 2010/0168799 | A1 | 7/2010 | Schumer |
| 2010/0185202 | A1 | 7/2010 | Lester et al. |
| 2010/0217270 | A1 | 8/2010 | Polinski et al. |
| 2010/0256687 | A1 | 10/2010 | Neufeld et al. |
| 2010/0274253 | A1 | 10/2010 | Ure |
| 2010/0318088 | A1 | 12/2010 | Warne et al. |
| 2011/0009865 | A1 | 1/2011 | Orfaly |
| 2012/0065689 | A1 | 3/2012 | Prasad et al. |
| 2012/0116203 | A1 | 5/2012 | Vancraen et al. |
| 2012/0123420 | A1 | 5/2012 | Honiball |
| 2012/0130434 | A1 | 5/2012 | Stemniski |
| 2012/0150242 | A1 | 6/2012 | Mannion |
| 2012/0191199 | A1 | 7/2012 | Raemisch |
| 2012/0234329 | A1 | 9/2012 | Vancraen et al. |
| 2012/0253350 | A1 | 10/2012 | Anthony et al. |
| 2012/0265301 | A1 | 10/2012 | Demers et al. |
| 2012/0277745 | A1 | 11/2012 | Lizee |
| 2013/0211410 | A1 | 8/2013 | Landes et al. |
| 2013/0236874 | A1 | 9/2013 | Iannotti et al. |
| 2013/0237989 | A1 | 9/2013 | Bonutti |
| 2013/0274778 | A1 | 10/2013 | Mercier et al. |
| 2013/0289570 | A1 | 10/2013 | Chao |
| 2013/0292870 | A1 | 11/2013 | Roger |
| 2014/0005672 | A1 | 1/2014 | Edwards et al. |
| 2014/0039501 | A1 | 2/2014 | Schickendantz et al. |
| 2014/0074099 | A1 | 3/2014 | Vigneron et al. |
| 2014/0094861 | A1 | 4/2014 | Fallin |
| 2014/0163568 | A1 | 6/2014 | Wong et al. |
| 2014/0257402 | A1 | 9/2014 | Barsoum |
| 2014/0259629 | A1 | 9/2014 | Dion et al. |
| 2014/0263674 | A1 | 9/2014 | Cerveny |
| 2014/0343555 | A1 | 11/2014 | Russi et al. |
| 2014/0371866 | A1 | 12/2014 | Chao et al. |
| 2014/0371897 | A1 | 12/2014 | Lin et al. |
| 2015/0032215 | A1 | 1/2015 | Slamin et al. |
| 2015/0045903 | A1 | 2/2015 | Neal |
| 2015/0066094 | A1 | 3/2015 | Anderson et al. |
| 2015/0081029 | A1 | 3/2015 | Bojarski et al. |
| 2015/0088142 | A1 | 3/2015 | Gibson |
| 2015/0093283 | A1 | 4/2015 | Miller et al. |
| 2015/0112348 | A1 | 4/2015 | Schoenefeld et al. |
| 2015/0142000 | A1 | 5/2015 | Seedhom et al. |
| 2015/0182342 | A1 | 7/2015 | Hafez |
| 2015/0227679 | A1 | 8/2015 | Kamer et al. |
| 2015/0230843 | A1 | 8/2015 | Palmer et al. |
| 2015/0305752 | A1 | 10/2015 | Eash |
| 2015/0342616 | A1 | 12/2015 | Fryman |
| 2015/0351780 | A1 | 12/2015 | Anderson et al. |
| 2015/0351916 | A1 | 12/2015 | Kosarek et al. |
| 2016/0015426 | A1 | 1/2016 | Dayton |
| 2016/0038161 | A1 | 2/2016 | Gibson |
| 2016/0100773 | A1 | 4/2016 | Ching et al. |

(56) References Cited

U.S. PATENT DOCUMENTS

| | | | | |
|---|---|---|---|---|
| 2016/0100847 | A1 | 4/2016 | Maxson | |
| 2016/0151165 | A1 | 6/2016 | Fallin et al. | |
| 2016/0175089 | A1 | 6/2016 | Fallin et al. | |
| 2016/0192951 | A1 | 7/2016 | Gelaude et al. | |
| 2016/0199198 | A1 | 7/2016 | Dietz et al. | |
| 2016/0256176 | A9 | 9/2016 | Lowery et al. | |
| 2016/0270829 | A1 | 9/2016 | Duggal et al. | |
| 2016/0270855 | A1 | 9/2016 | Kunz et al. | |
| 2016/0287395 | A1 | 10/2016 | Khalili et al. | |
| 2016/0338715 | A1 | 11/2016 | Bojarski et al. | |
| 2016/0354128 | A1 | 12/2016 | Jeng et al. | |
| 2016/0367270 | A1 | 12/2016 | Garlock et al. | |
| 2017/0014169 | A1 | 1/2017 | Dean et al. | |
| 2017/0020537 | A1 | 1/2017 | Tuten | |
| 2017/0027593 | A1 | 2/2017 | Bojarski et al. | |
| 2017/0042599 | A1 | 2/2017 | Bays et al. | |
| 2017/0079803 | A1 | 3/2017 | Lang | |
| 2017/0143511 | A1 | 5/2017 | Cachia | |
| 2017/0209189 | A9 | 7/2017 | Hatch et al. | |
| 2017/0231645 | A1 | 8/2017 | Metzger et al. | |
| 2017/0245906 | A1 | 8/2017 | Kugler et al. | |
| 2017/0245935 | A1 | 8/2017 | Kugler et al. | |
| 2017/0249440 | A1 | 8/2017 | Lang et al. | |
| 2017/0281353 | A1 | 10/2017 | Al Hares et al. | |
| 2017/0360578 | A1 | 12/2017 | Shin et al. | |
| 2018/0021145 | A1 | 1/2018 | Seavey et al. | |
| 2018/0028325 | A1 | 2/2018 | Bojarski et al. | |
| 2018/0049758 | A1 | 2/2018 | Amis et al. | |
| 2018/0116804 | A1 | 5/2018 | Hafez et al. | |
| 2018/0221071 | A1 | 8/2018 | Isch | |
| 2018/0235706 | A1 | 8/2018 | Asseln et al. | |
| 2018/0242987 | A1 | 8/2018 | Lintula et al. | |
| 2018/0289423 | A1 | 10/2018 | Singh et al. | |
| 2018/0317986 | A1 | 11/2018 | Jackman et al. | |
| 2018/0344326 | A1 | 12/2018 | Chan et al. | |
| 2019/0000629 | A1 | 1/2019 | Winslow | |
| 2019/0008532 | A1 | 1/2019 | Fitz et al. | |
| 2019/0117239 | A1 | 4/2019 | Verma | |
| 2019/0175277 | A1 | 6/2019 | Chav et al. | |
| 2019/0175351 | A1 | 6/2019 | Bojarski et al. | |
| 2019/0307495 | A1 | 10/2019 | Geldwert | |
| 2019/0365543 | A1 | 12/2019 | Slamin et al. | |
| 2020/0008813 | A1 | 1/2020 | Bonny et al. | |
| 2020/0046425 | A1 | 2/2020 | Lopes et al. | |
| 2020/0100909 | A1 | 4/2020 | Lang et al. | |
| 2020/0155323 | A1 | 5/2020 | Lang et al. | |
| 2020/0163721 | A1 | 5/2020 | Aghazadeh | |
| 2020/0214719 | A1 | 7/2020 | Fraone et al. | |
| 2020/0337714 | A1 | 10/2020 | Hafez et al. | |
| 2020/0356073 | A1 | 11/2020 | Tokushima | |
| 2020/0405322 | A1 | 12/2020 | Brailovski et al. | |
| 2021/0007760 | A1 | 1/2021 | Reisin | |
| 2021/0022781 | A1 | 1/2021 | Dacosta et al. | |
| 2021/0030429 | A1 | 2/2021 | Rose et al. | |
| 2021/0045756 | A1 | 2/2021 | Zakhary et al. | |
| 2021/0059691 | A1 | 3/2021 | Zille | |
| 2021/0059837 | A1 | 3/2021 | Rhodes | |
| 2021/0077120 | A1 | 3/2021 | Hatch et al. | |
| 2021/0077192 | A1 | 3/2021 | Perler et al. | |
| 2021/0085338 | A1 | 3/2021 | Dacosta et al. | |
| 2021/0090248 | A1 | 3/2021 | Choi et al. | |
| 2021/0106427 | A1 | 4/2021 | Mahfouz | |
| 2021/0113223 | A1 | 4/2021 | Schaumann et al. | |
| 2021/0121297 | A1 | 4/2021 | Cavanagh et al. | |
| 2021/0137537 | A1 | 5/2021 | Zille | |
| 2021/0161543 | A1 | 6/2021 | Mcauliffe et al. | |
| 2021/0186704 | A1 | 6/2021 | Fitz et al. | |
| 2021/0192759 | A1 | 6/2021 | Lang | |
| 2021/0196290 | A1 | 7/2021 | Iannotti et al. | |
| 2021/0212705 | A1 | 7/2021 | Reynolds et al. | |
| 2021/0219989 | A1 | 7/2021 | Chao | |
| 2021/0244477 | A1* | 8/2021 | Singh | A61B 34/10 |
| 2021/0256171 | A1 | 8/2021 | Hosseini | |
| 2021/0275196 | A1 | 9/2021 | Wodajo | |
| 2021/0282790 | A1 | 9/2021 | Sellman et al. | |
| 2021/0282823 | A1 | 9/2021 | Day et al. | |
| 2021/0290250 | A1 | 9/2021 | Denham et al. | |
| 2021/0298766 | A1 | 9/2021 | Loring et al. | |
| 2021/0307833 | A1 | 10/2021 | Farley et al. | |
| 2021/0307834 | A1 | 10/2021 | Gillman et al. | |
| 2021/0346038 | A1 | 11/2021 | Fiechter et al. | |
| 2021/0378752 | A1 | 12/2021 | Paul et al. | |
| 2021/0386437 | A1 | 12/2021 | Dacosta et al. | |
| 2021/0391058 | A1* | 12/2021 | Kostrzewski | G16H 20/40 |
| 2021/0393304 | A1 | 12/2021 | Geldwert | |
| 2022/0039965 | A1 | 2/2022 | Casey et al. | |
| 2022/0087822 | A1 | 3/2022 | Radermacher et al. | |
| 2022/0096157 | A1 | 3/2022 | Pollock et al. | |
| 2022/0133484 | A1 | 5/2022 | Lang | |
| 2022/0160405 | A1 | 5/2022 | Casey et al. | |
| 2022/0167998 | A1 | 6/2022 | Siccardi et al. | |
| 2022/0192685 | A1 | 6/2022 | Gazonnet et al. | |
| 2022/0202495 | A1 | 6/2022 | Pack | |
| 2022/0211387 | A1 | 7/2022 | Perler et al. | |
| 2022/0233203 | A1 | 7/2022 | Rhodes et al. | |
| 2022/0249106 | A1 | 8/2022 | Akallal et al. | |
| 2022/0249143 | A1 | 8/2022 | Hollis et al. | |
| 2022/0270762 | A1 | 8/2022 | Crawford et al. | |
| 2022/0273450 | A1 | 9/2022 | Steines et al. | |
| 2022/0296285 | A1 | 9/2022 | Besque et al. | |
| 2022/0313284 | A1 | 10/2022 | Korman | |
| 2022/0323086 | A1 | 10/2022 | Stemniski et al. | |
| 2022/0338934 | A1 | 10/2022 | Perler et al. | |
| 2022/0346806 | A1 | 11/2022 | Leemrijse et al. | |
| 2022/0370211 | A1 | 11/2022 | Campbell et al. | |
| 2023/0013727 | A1 | 1/2023 | Korman et al. | |
| 2023/0014384 | A1 | 1/2023 | Cordonnier et al. | |
| 2023/0077222 | A1 | 3/2023 | Awtrey | |
| 2023/0157705 | A1 | 5/2023 | Reynolds | |
| 2023/0190306 | A1 | 6/2023 | Kowalczyk et al. | |
| 2023/0281842 | A1 | 9/2023 | Ribeiro et al. | |
| 2023/0310013 | A1 | 10/2023 | Perler et al. | |
| 2023/0310051 | A1 | 10/2023 | Hafez et al. | |
| 2023/0363773 | A1 | 11/2023 | Perler et al. | |
| 2023/0371966 | A1 | 11/2023 | Spitler | |
| 2023/0389937 | A1 | 12/2023 | Penner et al. | |
| 2023/0404673 | A1 | 12/2023 | Spitler et al. | |
| 2024/0005504 | A1 | 1/2024 | Ribeiro et al. | |
| 2024/0008880 | A1 | 1/2024 | Spitler et al. | |
| 2024/0099778 | A1 | 3/2024 | Hlad et al. | |
| 2024/0108414 | A1 | 4/2024 | Dreyer et al. | |
| 2024/0252180 | A1 | 8/2024 | Khan et al. | |
| 2024/0252181 | A1 | 8/2024 | Perler et al. | |
| 2024/0268966 | A1 | 8/2024 | Spitler et al. | |
| 2024/0277350 | A1 | 8/2024 | Spitler et al. | |
| 2024/0282221 | A1 | 8/2024 | Perler et al. | |

FOREIGN PATENT DOCUMENTS

| | | | |
|---|---|---|---|
| AU | 2015203808 | B2 | 9/2017 |
| AU | 2020220169 | A1 | 9/2020 |
| AU | 2021286392 | A1 | 1/2022 |
| CA | 2491824 | A1 | 9/2005 |
| CA | 2608464 | C | 7/2012 |
| CA | 2854997 | A1 | 5/2013 |
| CA | 2713309 | C | 7/2013 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |

(56) References Cited

FOREIGN PATENT DOCUMENTS

| | | | |
|---|---|---|---|
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| CN | 106236185 | A | 12/2016 |
| CN | 205924106 | U | 2/2017 |
| CN | 206151532 | U | 5/2017 |
| CN | 105105853 | B | 7/2017 |
| CN | 108030532 | A | 5/2018 |
| CN | 207721902 | U | 8/2018 |
| CN | 112914724 | B | 2/2022 |
| CN | 117297772 | B | 2/2024 |
| CN | 117322951 | B | 2/2024 |
| CN | 109223098 | B | 5/2024 |
| DE | 2910627 | A1 | 9/1980 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124832 | B1 | 8/2012 |
| EP | 2750617 | A1 | 7/2014 |
| EP | 2856951 | A1 | 4/2015 |
| EP | 2624764 | B1 | 12/2015 |
| EP | 3000443 | A3 | 7/2016 |
| EP | 2083758 | B1 | 11/2017 |
| EP | 2632349 | B1 | 3/2018 |
| EP | 3013256 | B1 | 11/2018 |
| EP | 3171795 | B1 | 11/2018 |
| EP | 3672535 | A1 | 7/2020 |
| EP | 2558010 | B1 | 5/2021 |
| EP | 3948895 | A1 | 2/2022 |
| EP | 3740141 | B1 | 4/2022 |
| EP | 2844162 | B1 | 7/2022 |
| FR | 2362616 | A1 | 3/1978 |
| FR | 2764183 | A1 | 12/1998 |
| FR | 2953120 | B1 | 1/2012 |
| FR | 3030221 | A1 | 6/2016 |
| FR | 3117328 | B1 | 3/2023 |
| GB | 2154143 | A | 9/1985 |
| GB | 2154144 | A | 9/1985 |
| GB | 2334214 | B | 1/2003 |
| GB | 2589960 | A | 6/2021 |
| JP | S635739 | A | 1/1988 |
| JP | 2004174265 | A | 6/2004 |
| JP | 2006158972 | A | 6/2006 |
| JP | 4134243 | B2 | 8/2008 |
| JP | 2011092405 | A | 5/2011 |
| JP | 4796943 | B2 | 10/2011 |
| JP | 2014511207 | A | 5/2014 |
| JP | 2014521384 | A | 8/2014 |
| KR | 100904142 | B1 | 6/2009 |
| KR | 1020160090006 | A | 7/2016 |
| KR | 1020180118476 | A | 10/2018 |
| KR | 101952368 | B1 | 2/2019 |
| MD | 756 | Z | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| RU | 182499 | U1 | 8/2018 |
| RU | 2789960 | C2 | 2/2023 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009001083 | A1 | 12/2008 |
| WO | 2009029798 | A1 | 3/2009 |
| WO | 2009032101 | A2 | 3/2009 |
| WO | 2010099231 | A3 | 11/2010 |
| WO | 2011005327 | A1 | 1/2011 |
| WO | 2011037885 | A1 | 3/2011 |
| WO | 2012024317 | A2 | 2/2012 |
| WO | 2012029008 | A1 | 3/2012 |
| WO | 2012176077 | A1 | 12/2012 |
| WO | 2013026786 | A1 | 2/2013 |
| WO | 2013041618 | A1 | 3/2013 |
| WO | 2013134387 | A1 | 9/2013 |
| WO | 2013156816 | A2 | 10/2013 |
| WO | 2014020561 | A1 | 2/2014 |
| WO | 2014020562 | A1 | 2/2014 |
| WO | 2014022055 | A1 | 2/2014 |
| WO | 2014085882 | A1 | 6/2014 |
| WO | 2014147099 | A1 | 9/2014 |
| WO | 2014152219 | A2 | 9/2014 |
| WO | 2014200017 | A1 | 12/2014 |
| WO | 2015003284 | A2 | 1/2015 |
| WO | 2015094409 | A1 | 6/2015 |
| WO | 2015127515 | A2 | 9/2015 |
| WO | 2016012731 | A1 | 1/2016 |
| WO | 2016102025 | A1 | 6/2016 |
| WO | 2017031000 | A1 | 2/2017 |
| WO | 2017122076 | A2 | 7/2017 |
| WO | 2017151833 | A1 | 9/2017 |
| WO | 2018167369 | A1 | 9/2018 |
| WO | 2019060780 | A2 | 3/2019 |
| WO | 2019052622 | A4 | 5/2019 |
| WO | 2019180747 | A1 | 9/2019 |
| WO | 2020060349 | A1 | 3/2020 |
| WO | 2021054518 | A1 | 3/2021 |
| WO | 2021091071 | A1 | 5/2021 |
| WO | 2021118733 | A1 | 6/2021 |
| WO | 2021127625 | A1 | 6/2021 |
| WO | 2021240290 | A1 | 12/2021 |
| WO | 2022155208 | A1 | 7/2022 |
| WO | 2022182312 | A1 | 9/2022 |
| WO | 2023096516 | A1 | 6/2023 |
| WO | 2024025840 | A1 | 2/2024 |

OTHER PUBLICATIONS

Integra, "Integra Large Qwix Positioning and Fixation Screw, Surgical Technique," 2012, 16 pages.

Jackson III et al., "The Surgical Learning Curve for Modified Lapidus Procedure for Hallux Valgus Deformity," Foot & Ankle Specialist, Jul. 2021, 5 pages.

Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.

KLS Martin Group, "Individual Patient Solutions IPS Implants" , https://www.klsmartin.com/en-na/products/individual-patient-solutions/ips-implants/, Downloaded: Jun. 1, 2022, pp. 8.

Kurup et al., "Midfoot arthritis—current concepts review," Journal of Clinical Orthopaedics and Trauma, vol. 11, 2020, pp. 399-405.

La Reaux et al., "Metatarsus adductus and hallux abducto valgus: their correlation," The Journal of Foot Surgery, vol. 26, No. 4, Jul. 1987, pp. 304-308, Abstract Only.

Langan et al., "Maintenance of Correction of the Modified Lapidus Procedure With a First Metatarsal to Intermediate Cuneiform Cross-

(56) References Cited

OTHER PUBLICATIONS

Screw Technique," Foot & Ankle International, vol. 41, No. 4, Apr. 1, 2020, published online: Dec. 26, 2019, pp. 426-436.
Lapidus, "The Author's Bunion Operation From 1931 to 1959," Clinical Orthopaedics, vol. 16, 1960, pp. 119-135.
Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Le et al., "Tarsometatarsal Arthrodesis," Operative Techniques in Foot and Ankle Surgery, Section II, Chapter 40, 2011, pp. 281-285.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
Little, "Joint Arthrodesis For Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Machacek Jr. et al., "Salvage of a Failed Keller Resection Arthroplasty," The Journal of Bone and Joint Surgery, vol. 86A, No. 6, Jun. 2004, pp. 1131-1138.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Marshall et al., "The identification and appraisal of assessment tools used to evaluate metatarsus adductus: a systematic review of their measurement properties," Journal of Foot and Ankle Research, vol. 11, No. 25, 2018, 10 pages.
Mcaleer et al., "A systematic approach to the surgical correction of combined hallux valgus and metatarsus adductus deformities," The Journal of Foot & Ankle Surgery, May 21, 2021, 6 pages.
Mcaleer et al., "Radiographic Outcomes Following Triplanar Correction of Combined Hallux Valgus and Metatarsus Adductus Deformities," ACFAS Scientific Conference, Poster, Feb. 2022, 1 page.
Mccabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Michelangelo Bunion System, Surgical Technique ", Instratek Incorporated, publication date unknown, 4 pages."
Miller et al., "Variable Angle Locking Compression Plate as Alternative Fixation for Jones Fractures: A Case Series," Kansas Journal of Medicine, vol. 12, No. 2, May 2019, pp. 28-32.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mizuno et al., "Detorsion Osteotomy of the First Metatarsal Bone in Hallux Valgus," Japanese Orthopaedic Association, Tokyo, 1956; 30:813-819.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
Mortier et al., "Axial Rotation of the First Metatarsal Head in a Normal Population and Hallux Valgus Patients," Orthopaedics and Traumatology: Surgery and Research, vol. 98, 2012, pp. 677-683.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Musculoskeletal Key "Arthrodesis of the Tarsmetatarsal Joint" https://musculoskeletalkey.com/arthrodesis-of-the-tarsometatarsal-joint/, Retrieved May 8, 2020, pp. 11.
Myerson, "Cuneiform-Metatarsal Arthrodesis," The Foot and Ankle, Chapter 9, 1997, pp. 107-117.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Nix et al., "Prevalence of hallux valgus in the general population: a systematic review and meta-analysis," Journal of Foot and Ankle Research, vol. 3, No. 21, 2010, 9 pages.
Novastep, "Pecaplasty Percutaneous Bunion Correction" Downloaded Jun. 29, 2022, pp. 24.
Novastep, "Pecaplasty Percutaneous Bunion Correction—Brochure Pecaplasty Targeting Guide" Downloaded Dec. 15, 2021, pp. 4.
Odenbring et al., "A guide instrument for high tibial osteotomy," Acta Orthopaedica Scandinavica, vol. 60, No. 4, 1989, pp. 449-451.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Instratek, "Michelangelo Bunion System, Surgical Technique", Instratek Incorporated, publication date unknown, 4 pages.
Tricot et al., "3D-corrective osteotomy using surgical guides for posttraumatic distal humeral deformity," Acta Orthopaedica Belgica, vol. 78, No. 4, 2012, pp. 538-542.
Vaida et al., "Effect on Foot Width With Triplanar Tarsometatarsal Arthrodesis for Hallux Valgus," Foot & Ankle Orthopaedics, vol. 5, No. 3, 2020, pp. 1-5.
Nyska, Synergy 3D Med, "Anatomical Model: Calcaneus" , 2022, pp. 3.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.

(56) References Cited

OTHER PUBLICATIONS

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Perler, "Cuboid Suspension in Charcot Reconstruction. Using 3D Imaging for Planning, Printing and Execution for Complex Deformity Correction" Downloaded Apr. 2021, pp. 4.
Peters et al., "Flexor Hallucis Longus Tendon Laceration as a Complication of Total Ankle Arthroplasty," Foot & Ankle International, vol. 34, No. 1, 2013, pp. 148-149.
Ray et al., "Hallux Valgus," Foot & Ankle Orthopaedics, vol. 4, No. 2, 2019, pp. 1-12.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Santrock et al., "Hallux Valgus Deformity and Treatment: A Three-Dimensional Approach: Lapiplasty," Foot & Ankle Clinics, vol. 23, No. 2, 2018, pp. 281-295.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Schon et al., "Cuneiform-Metatarsal Arthrodesis for Hallux Valgus," The Foot and Ankle, Second Edition, Chapter 8, 2002, pp. 99-117.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Shima et al., "Operative Treatment for Hallux Valgus With Moderate to Severe Metatarsus Adductus," Foot & Ankle International, vol. 40, No. 6, 2019, pp. 641-647.
Shurnas et al., "Proximal Metatarsal Opening Wedge Osteotomy," Operative Techniques in Foot and Ankle Surgery, Section I, Chapter 13, 2011, pp. 73-78.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Smith et al., "Intraoperative Multiplanar Alignment System to Guide Triplanar Correction of Hallux Valgus Deformity," Techniques in Foot & Ankle Surgery, 2017, 8 pages.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Smith et al., "Understanding Frontal Plane Correction in Hallux Valgus Repair," Clinics in Podiatric Medicine and Surgery, vol. 35, 2018, pp. 27-36.
Sokoloff, "Lapidus Procedure," Textbook of Bunion Surgery, Chapter 15, 1981, pp. 277-287.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Stamatis et al., "Mini Locking Plate as Medial Buttress for Oblique Osteotomy for Hallux Valgus," Foot & Ankle International, vol. 31, No. 10, Oct. 2010, pp. 920-922.
Stryker, "PROstep Minimally Invasive Surgery" https://www.stryker.com/us/en/foot-and-ankle/products/prostep.html, Downloaded Jun. 23, 2023, pp. 10.
Synergy 3D Med, "Anatomical Model: Calcaneus" Downloaded Mar. 2, 2023, pp. 2.
Synopsys, "Medical Image Segmentation with Machine Learning—Simpleware Automated Solution Modules" , https://www.synopsys.com/simpleware/software/auto-segmenter-modules.html#simpleware-as-ortho, 2022, pp. 12.
Talbot et al., "Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Tornier Technology, "Tornier Blueprint 3D Planning + PSI" , https://www.wrightemedia.com/ProductFiles/Files/PDFs/CAW-8609_EN_HR_LE.pdf, Feb. 2017, pp. 12.
Total Ankle Institute, "Prophecy: Preoperative Navigation Guides" , https://www.totalankleinstitute.com/infinity-products/prophecy-preoperative-navigation-guides/, 2019, pp. 6.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Treace "FastGrafter Autograft Harvesting System" Downloaded from https://www.lapiplasty.com/surgeons/other-products/fastgrafter/, Dec. 4, 2024, pp. 8.
Treace Medical Concepts, "Adductoplasty Midfoot Correction System", https://www.lapiplasty.com/surgeons/other-products/adductoplasty-system/, Downloaded May 2, 2022, pp. 9.
Use for BME Speed Nitinol Staple Fixation for the Lapidus Procedure, "date unknown, 1 page."
Virzi et al. "Comprehensive Review of 3D Segmentation Software Tools for MRI Usable for Pelvic Surgery Planning", Journal of Digital Imaging (2020) 33, pp. 99-110.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Decarbo et al., "The Weil Osteotomy: A Refresher," Techniques in Foot and Ankle Surgery, vol. 13, No. 4, Dec. 2014, pp. 191-198.
Defendant Fusion Orthopedics LLC's Invalidity Contentions, No. CV-22-00490-PHX-SRB, US District Court for the District of Arizona, Aug. 27, 2022, 41 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dinapoli et al., "Metatarsal Osteotomy for the Correction of Metatarsus Adductus," Reconstructive Surgery of the Foot and Leg, 1989, pp. 242-250.
Disior, "Bonelogic Foot & Ankle Module" , https://www.disior.com/foot--ankle.html, Downloaded Jun. 1, 2022, pp. 6.

(56) References Cited

OTHER PUBLICATIONS

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics—The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Fazal et al., "First metatarsophalangeal joint arthrodesis with two orthogonal two hole plates," Acta Orthopaedica et Traumatologica Turcica, vol. 52, 2018, pp. 363-366.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Fibretuff, "3D Printing, CNC Machining, Molding and Extruding Biocompatible material's with "bone like" Qualities for 3D Printing" https://fibretuff.us, Downloaded Feb. 24, 2023, pp. 22.
Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fraissler et al., "Treatment of hallux valgus deformity," Efort Open Reviews, vol. 1, Aug. 2016, pp. 295-302.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.
Garthwait, "Accu-Cut System Facilitates Enhanced Precision," Podiatry Today, vol. 18, No. 6, Jun. 2005, 6 pages.
Gerard et al., "The Modified Lapidus Procedure," Orthopedics, vol. 31, No. 3, Mar. 2008, 7 pages.
Ghali et al., "The Management of Metatarsus Adductus et Supinatus," The Journal of Bone and Joint Surgery, vol. 66-B, No. 3, May 1984, pp. 376-380.
Giannoudis et al., "Hallux Valgus Correction," Practical Procedures in Elective Orthopaedic Surgery, Pelvis and Lower Extremity, Chapter 38, 2012, 22 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems fr die Knieendoprothetik," Forschungsberichte, Technische Universitat Munchen, 165, 2002, 11 pages, including partial English Translation.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gregg et al., "Plantar plate repair and Weil osteotomy for metatarsophalangeal joint instability," Foot and Ankle Surgery, vol. 13, 2007, pp. 116-121.
Greiner, "The Jargon of Pedal Movements," Foot & Ankle International, vol. 28, No. 1, Jan. 2007, pp. 109-125.
Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).
Groves, "Functional Position Joint Sectioning: Pre-Load Method for Lapidus Arthrodesis," The Podiatry Institute, Update 2015, Chapter 6, 2015, pp. 23-29.
Groves, "Operative Report," St. Tammany Parish Hospital, Date of Procedure, Mar. 26, 2014, 2 pages.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Hardy et al., "Observations on Hallux Valgus," The Journal of Bone and Joint Surgery, vol. 33B, No. 3, Aug. 1951,pp. 376-391.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Ho et al., "Hallux rigidus," Efort Open Reviews, vol. 2, Jan. 2017, pp. 13-20.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.

(56) References Cited

OTHER PUBLICATIONS

"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Acumed "Acumed Osteotomy System" with partial English Translation, 2014, pp. 19.
Additive Orthopaedics, "The First and Only FDA Approved Patient Specific Talus Spacer" , https://totaltalusreplacement.com, Downloaded: Mar. 4, 2022, pp. 11.
Aiyer et al. "Prevalence of Metatarsus Adductus in Patients Undergoing Hallux Valgus Surgery" Foot & Ankle International 2014, vol. 35(12), pp. 1292-1297.
Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.
Alvine et al. "Peg and Dowel Fusion of the Proximal Interphalangeal Joint" Foot & Ankle vol. 1, No. 2, 1980 American Orthopaedic Foot Society, pp. 5.
Arthrex "Chevron Osteotomy" https://www.arthrex.com/foot-ankle/chevron-osteotomy, Retrieved Nov. 30, 2022, pp. 7.
Arthrex "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, pp. 3.
Arthrex, "Distal Tibia Allograft Workstation for Glenoid Bone Loss, Surgical Technique" Arthrex.com, 2018, pp. 8.
Baravarian, "Why the Lapidus Procedure is Ideal for Bunions" Podiatry Today, https://www.hmpgloballearningnetwork.com/site/podiatry/article/5542, May 2006 pp. 8.
Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.
Bednarz et al. "Modified Lapidus Procedure for the Treatment of Hypermobile Hallux Valgus" Foot & Ankle, American Orthopaedic Foot & Ankle Society, 2000, pp. 6.
Bennett et al. "Intraosseous Sliding Plate Fixation Used in Double Osteotomy Bunionectomy" Foot & Ankle International, 2019, vol. 40(1), pp. 85-88.
Biopro "Accu-Cut Osteotomy Guide System Accurate and consistent hallux valgus correction" Document Dates Sep. 16, 2019, pp. 2.
Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.
Bouaicha et al. "Fixation of Maximal Shift Scarf Osteotomy with Inside-Out Plating: Technique Tip" Foot & Ankle International, vol. 32, No. 5, May 2011, pp. 567-569.
Buda et al. "Effect of Fixation Type and Bone Graft on Tarsometatarsal Fusion" Foot & Ankle International 2018, vol. 39(12), pp. 1394-1402.
Carr et al. "Correctional Osteotomy for Metatarsus Primus Varus and Hallux Valgus*" The Journal of Bone and Joint Surgery, vol. 50-A, No. 7, Oct. 1968, pp. 1353-1367.
Catanese et al. "Measuring Sesamoid Position in Hallux Valgus When Is the Sesamoid Axial View Necessary?" Foot & Ankle Specialist, Downloaded Aug. 15, 2016, pp. 1-3.
Chesser et al. "New Advances With The Tarsometatarsal" Podiatry Today, vol. 30, Issue 10, Oct. 2017, pp. 28-36.
Chomej et al. "Lateralising DMMO (MIS) for simultaneous correction of a pes adductus during surgical treatment of a hallux valgus" Journal Pre-proof, The Foot, Accepted Jul. 16, 2020, pp. 33.
Cichero et al. "Different fixation constructs and the risk of non-union following first metatarsophalangeal joint arthrodesis" Foot and Ankle Surgery, 27, 2021, Accepted Oct. 15, 2020, pp. 789-792.
Coetzee et al., "Revision Hallux Valgus Correction," Operative Techniques in Foot and Ankle Surgery, Section I, Chapter 15, 2011, pp. 84-96.
Collan et al., "The biomechanics of the first metatarsal bone in hallux valgus: A preliminary study utilizing a weight bearing extremity CT," Foot and Ankle Surgery, vol. 19, 2013, pp. 155-161.
"Futura Forefoot Implant Arthroplasty Products," Tornier, Inc., 2008, 14 pages.
"Hat-Trick Lesser Toe Repair System, Foot and Ankle Technique Guide, Metatarsal Shortening Osteotomy Surgical Technique," Smith & Nephew, 2014, 16 pages.
"Hat-Trick Lesser Toe Repair System," Smith & Nephew, Brochure, Aug. 2014, 12 pages.
"Hoffmann II Compact External Fixation System", Stryker, Brochure, Literature No. 5075-1-500, 2006, 12 pages.
"Hoffmann II Micro Lengthener", Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Patient to Patient Precision, Accu-Cut, Osteotomy Guide System, BioPro, Foot & Ankle International Journal, vol. 23, No. 8, Aug. 2002, 2 pages.
Blomer "Problems and complications of knee endoprostheses from a manufacturer's point of view" Orthopade 200, 29, pp. 688-696, English Abstract.
"Prophecy Inbone Preoperative Navigation Guides", Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Smith & Nephew scores a Hat-Trick with its entry into the high-growth hammer toe repair market, Smith & Nephew, Jul. 31, 2014, 2 pages.
"Lag Screw Target Bow," Stryker Leibinger GmbH & Co. KG, Germany 2004, 8 pages.
Anderson et al., "Uncemented Star Total Ankle Protheses" Journal of Bone Joint Surgery America, Sep. 2004, Abstract of Article, pp. 6.
Coetzee et al., "The Lapidus Procedure: A Prospective Cohort Outcome Study," Foot & Ankle International, vol. 25, No. 8, Aug. 2004, pp. 526-531.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

(56) References Cited

OTHER PUBLICATIONS

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Weber et al., "A Simple System For Navigation Of Bone Alignment Osteotomies Of The Tibia," International Congress Series, vol. 1268, Jan. 2004, pp. 608-613, (Abstract Only).
Wukich et al., "Hypermobility of the First Tarsometatarsal Joint," Foot and Ankle Clinics, vol. 10, No. 1, Mar. 2005, pp. 157-166.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fuchirurgie Das V-tek-System," ABW Wissenschaftsverlag GmbH, 2009, 11 pages, including English Abstract.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wienke et al., "Bone Stimulation For Nonunions: What the Evidence Reveals," Podiatry Today, vol. 24, No. 9, Sep. 2011, pp. 52-57.
Williams et al., "Metatarsus adductus: Development of a nonsurgical treatment pathway," Journal of Paediatrics and Child Health, vol. 49, 2013, pp. E428-433.
Yasuda et al., "Proximal Supination Osteotomy of the First Metatarsal for Hallux Valgus," Foot and Ankle International, vol. 36, No. 6, Jun. 2015, pp. 696-704.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Wright Medical, "How Blueprint Works—from CT to 3D [CAW-9389]", https://www.wrightmeded.com/videos/how-blueprint-works-from-ct-to-3d-caw-9389, video time mark 32 seconds to 48 seconds, Dated May 26, 2022.
European Patent Office, "Extended European Search Report and Written Opinion", From Application No. 20862480.9, Dated Sep. 4, 2023, pp. 8.
International Searching Authority, "International Preliminary Report on Patentability and Written Opinion", From Application No. PCT/US2020/050764, Mailed Dec. 17, 2020, pp. 9.
D'Amico et al., "Motion of the First Ray: Clarification Through Investigation," Journal of the American Podiatry Association, vol. 69, No. 1, Jan. 1979, pp. 17-23.
Dayton et al., "Biwinged Excision for Round Pedal Lesions," The Journal of Foot and Ankle Surgery, vol. 35, No. 3, 1996, pp. 244-249.
Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Principles of Management of Growth Plate Fractures in the Foot and Ankle," Clinics in Podiatric Medicine and Surgery, Pediatric Foot Deformities, Oct. 2013, 17 pages.
Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.

(56) References Cited

OTHER PUBLICATIONS

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton, "Tarsal-Metatarsal Joint: Primary & Revision Arthrodesis" Disclosure: Speaker for Orthofix and Biomet, Apr. 2014, pp. 38.
Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.
Dayton et al., "A new triplanar paradigm for bunion management," Lower Extremity Review, Apr. 2015, 9 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.
Dayton "Evidence-Based Bunion Surgery: A Critical Examination of Current and Emerging Concepts and Techniques" Springer International Publishing, 2017, pp. 254.
Dayton et al. "Biomechanical Characteristics of Biplane Multiplanar Tension-Side Fixation for Lapidus Fusion" The Journal of Foot & Ankle Surgery, 2018, pp. 1-5.
Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Conti et al., "Effect of the Modified Lapidus Procedure for Hallux Valgus on Foot Width," Foot & Ankle International, Feb. 1, 2020, published online: Oct. 30, 2019, 6 pages.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Dayton et al. "Comparison of Radiographic Measurements Before and After Triplane Tarsometatarsal Arthrodesis for Hallux Valgus" The Journal of Foot & Ankle Surgery 59, 2020, pp. 291-297.
Curran et al. "Functional Capabilities After First Metatarsal Phalangeal Joint Arthrodesis Using a Locking Plate and Compression Screw Construct" The Journal of Foot & Ankle Surgery, 2021, pp. 1-5.
De Carvalho, et al. "Automated Three-dimensional distance and coverage mapping of hallux valgus: a case-control study" Journal of Foot and Ankle, 2022; 16(1), pp. 5.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
De Heer et al., "Procedure-Specific Hardware Removal After Evans Osteotomy" Journal of the American Podiatric Medical Association, vol. 110, No. 2, Mar./Apr. 2020, pp. 1-7.
DeCarbo et al., "Locking Plates: Do They Prevent Complications?," Podiatry Today, Apr. 2014, 7 pages.
DeCarbo et al., "Resurfacing Interpositional Arthroplasty for Degenerative Joint Disease of the First Metatarsalphalangeal Joint," Podiatry Management, Jan. 2013, pp. 137-142.

* cited by examiner

PATIENT-SPECIFIC SURGICAL METHODS AND INSTRUMENTATION

CROSS-REFERENCE TO RELATED APPLICATIONS

This application is a continuation of U.S. patent application Ser. No. 17/681,674 filed on Feb. 25, 2022, entitled "PATIENT-SPECIFIC SURGICAL METHODS AND INSTRUMENTATION", which is a continuation-in-part of U.S. patent application Ser. No. 17/020,630 filed on Sep. 14, 2020, entitled "PATIENT-SPECIFIC SURGICAL METHODS AND INSTRUMENTATION" and issued as U.S. Pat. No. 11,931,106 on Mar. 19, 2024, which claims the benefit of U.S. Provisional Application No. 62/900,294, filed Sep. 13, 2019, each of which are hereby incorporated by reference in their entirety. This application also claims the benefit of U.S. Provisional Application No. 63/190,551, filed May 19, 2021 and claims the benefit of U.S. Provisional Application No. 63/224,344, filed Jul. 21, 2021, each of which are hereby incorporated by reference in their entirety.

TECHNICAL FIELD

The present disclosure relates to surgical devices, systems, instruments, and methods. More specifically, the present disclosure relates to patient-specific cutting guides and implants, and methods of designing and using the same.

BACKGROUND

Various bone conditions may be corrected using an osteotomy, in which one or more bones are cut, replaced, and/or reoriented. Cutting guides are often used to help the surgeon properly locate, position, and make one or more cuts. Unfortunately, many known cutting guides are not patient-specific, and can be difficult to properly position to perform the osteotomy on a specific patient. Even if properly positioned, many known cutting guides are difficult to secure at the desired position, without moving away from the desired position prior to performing the osteotomy. As a result, many known osteotomy procedures carry risk of an improper cut that fails to correct the underlying condition, or even endangers surrounding tissues.

SUMMARY

The various apparatus, devices, systems, and/or methods of the present disclosure have been developed in response to the present state of the art, and in particular, in response to the problems and needs in the art that have not yet been fully solved by currently available technology. One general aspect of the present disclosure can include a patient specific instrument for correcting a condition present in a patient. The patient specific instrument may include a body that may include: a proximal side, a distal side, a medial side, and a lateral side; an inferior side that may include a bone engagement surface shaped to match a first surface of a first bone and a second surface of a second bone of a joint; a superior side that may include a first guide feature and a second guide feature that together, with the bone engagement surface overlying the first surface and the second surface, are positioned to guide resection of the first bone and the second bone during a surgical osteotomy for correcting the condition. The instrument includes where the body is configured to seat transverse to the joint with the bone engagement surface engaging the first surface of the first bone and the second surface of the second bone.

Implementations may include one or more of the following features. The patient specific instrument where when the bone engagement surface seats over the joint: the first guide feature is configured to define a first cut surface formed by resection of the first bone; the second guide feature is configured to define a second cut surface formed by resection of the second bone; where the second cut surface extends inferiorly away from the first cut surface at a first angle measured from the first cut surface and extends posteriorly away from the first cut surface at a second angle measured relative to the first cut surface; and where the first cut surface is perpendicular to a longitudinal axis of the first bone. One of the first guide feature and the second guide feature may include a position and an orientation, at least one of which is based on patient imaging data. In one implementation, the patient imaging data is used to define a distance between at least one of a first top edge of the first guide feature and the first surface and a second top edge of the second guide feature and the second surface.

The body may include: a proximal arm extending from the body; and a distal arm extending from the body and away from the proximal arm; and where: the distal arm may include a first bone attachment feature positioned perpendicular to the first guide feature and parallel with a first alignment feature configured to be coupled to the first bone; the proximal arm may include a second bone attachment feature and a second alignment feature each positioned perpendicular to the second guide feature; and where the first alignment feature and first bone attachment feature are not aligned and the first alignment feature and the second alignment feature are configured to align when the first bone is rotated. The second bone attachment feature and the second alignment feature may include a single feature.

The body may extend between a lateral end of the joint and a medial end of the joint and the proximal arm and the distal arm are aligned and extend proximal to the lateral end of the joint. At least one of the body, the proximal arm, the distal arm, and the bone engagement surface of the inferior side of the body is configured to engage a dorsal surface of one or more of the first bone and the second bone. The first alignment feature and second alignment feature are configured to couple with an active compression instrument that compresses the first bone and the second bone for deployment of fasteners that connect the first bone and the second bone. The lateral side of the body may include a lateral superior surface and a lateral inferior surface that meet at a lateral edge, the lateral inferior surface angled to connect the inferior side of the body and the lateral edge such that the lateral inferior surface does not impinge upon soft tissue near the joint.

The medial side of the body may include a medial superior surface and a medial inferior surface that meet at a medial edge, the medial inferior surface angled to connect the inferior side of the body and the medial edge such that the medial inferior surface does not impinge upon soft tissue near the joint. The bone engagement surface of the inferior side of the body is configured to engage a dorsal surface of one or more of the first bone and the second bone.

One general aspect of the present disclosure can include a method for making a patient specific cutting guide configured to mitigate a condition present in a patient. The method includes accessing a bone model of one or more bones of a patient based on the condition and/or the bone model; defining one or more guide features of a preliminary cutting guide model for an osteotomy procedure, the preliminary cutting guide model may include a superior surface and an inferior surface; defining at least a portion of the inferior surface of the preliminary cutting guide model according to a topographical surface of at least one bone of the bone model such that the inferior surface substantially matches a contour of the topographical surface; and where the preliminary cutting guide model is configured for fabrication of a patient specific cutting guide corresponding to the preliminary cutting guide model.

Implementations may include one or more of the following features. The method may include defining one or more alignment features of the preliminary cutting guide model for the osteotomy procedure. Accessing the bone model further may include: modifying a bone model may include a first modeled bone and a second modeled bone of a joint of the patient such that the first modeled bone is rotated about a longitudinal axis of the first modeled bone from a first position to a second position; defining a first cut surface in the first modeled bone, where the first cut surface is perpendicular to the longitudinal axis of the first modeled bone; defining a first angle for a second cut surface of the second modeled bone, the first angle measured relative to the first cut surface and extends inferiorly away from the first cut surface; defining a second angle for the second cut surface of the second modeled bone, the second angle measured relative to the first cut surface and configured to mitigate the condition; modifying the bone model of the first modeled bone to include the first cut surface and the second modeled bone to include the second cut surface; and where the one or more guide features of a preliminary cutting guide model are configured to enable a surgeon to form the first cut surface and the second cut surface.

Defining one or more guide features of the preliminary cutting guide model further may include: defining a first slot configured to guide formation of a first cut surface of a first bone of the patient corresponding to a first modeled bone; defining a second slot configured to guide formation of a second cut surface of a second bone of the patient corresponding to a second modeled bone; and where the first slot and second slot are positioned such that fixing the first cut surface of the first bone to the second cut surface of the second bone mitigates the condition. The method may include selecting the preliminary cutting guide model from a repository of template cutting guide models, each template cutting guide model configured for an osteotomy procedure configured to correct one of a plurality of conditions. The method may include defining a coupler configured to engage an alignment guide, the alignment guide configured to indicate a resulting alignment of patient body parts upon completion of the osteotomy procedure. The bone model is derived from patient imaging data generated while the patient places their weight on at least one joint involved in the osteotomy procedure.

One general aspect of the present disclosure can include a system for correcting a condition present in a patient. The system may include a cut guide that may include: a first guide feature configured to define a first cut surface configured for resection of a first metatarsal of a patient, a second guide feature configured to define a second cut surface configured for resection of a medial cuneiform of a patient, an inferior side may include a bone engagement surface shaped to match a first surface of the first metatarsal and a second surface of the medial cuneiform, a medial cuneiform alignment feature coupled to the medial cuneiform, where one of the first guide feature and the second guide feature is configured based on patient imaging data such that fusion of the first metatarsal at the first cut surface to the medial cuneiform at the second cut surface mitigates the condition. The system includes a first metatarsal alignment feature coupled to the first metatarsal, the first metatarsal alignment feature configured to enable a user to rotate the first metatarsal from a malrotation position to a desired rotation position; and a compressor/distractor configured to engage the medial cuneiform alignment feature and the first metatarsal alignment feature and compress the first cut surface of the first metatarsal against the second cut surface of the medial cuneiform.

Implementations may include one or more of the following features. The system where: the first metatarsal alignment feature may include a pin guide configured to position alignment pins for a desired rotation angle of the first metatarsal about its longitudinal axis; the compressor/distractor may include a pair of legs that are closer to each other at distal end of each leg than at a proximal end of each leg.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

DETAILED DESCRIPTION

Figures 1A, 1B:
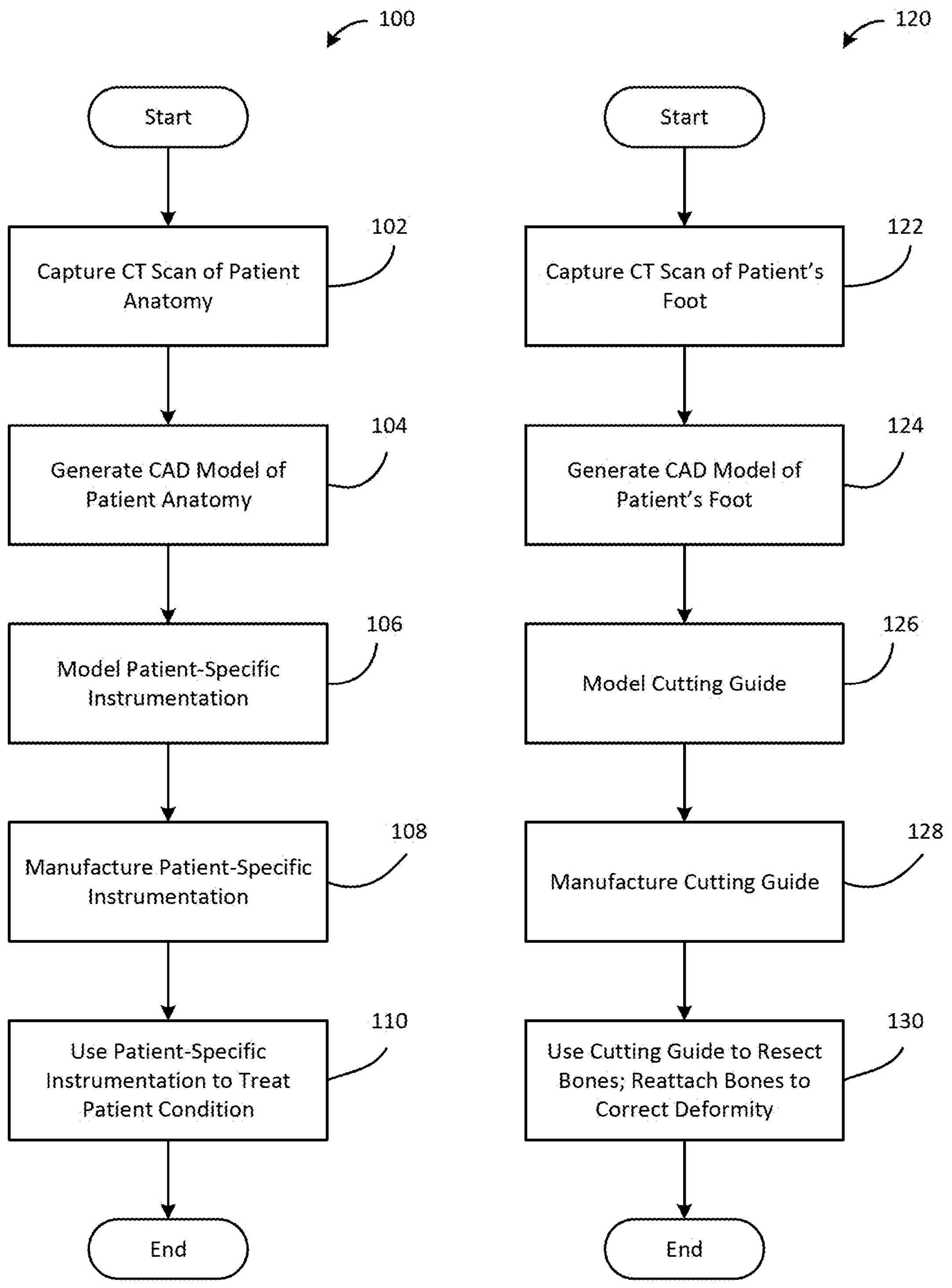
FIG. 1A is a flowchart diagram depicting a method for correcting a bone condition, according to one embodiment.
FIG. 1B is a flowchart diagram depicting a method for correcting bunion deformity of the human foot, according to one embodiment.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

The present disclosure discloses surgical systems and methods by which a bone condition, such as a deformity, may be corrected using patient-specific instrumentation. Known methods of correcting bone conditions are often limited to a finite range of discretely sized instruments. A patient with an unusual condition, or anatomy that falls between instrument sizes, may not be readily treated with such systems. One example is correction of a bunion, in particular, via adjustment of the angulation between a cuneiform and a metatarsal.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may entail capturing a scan of only the particular bone(s) to be treated, or may entail capture of additional anatomic information, such as the surrounding tissues. Additionally or alternatively, the step 102 may entail receiving a previously captured image, for example, at a design and/or fabrication facility. Performance of the step 102 may result in possession of a three-dimensional model of the patient's anatomy, or three-dimensional surface points that can be used to construct such a three-dimensional model.

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiogramand others, represent other technologies that produce data susceptible to representation as a parameter graph vs. time or maps that contain data about the measurement locations. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable in the translation of models to the clinical setting with both diagnostic and therapeutic applications. (Id.) In certain embodiments, medical image computing can be used to generate a bone model, a patient specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.) As used herein, "additive manufacturing" refers to a manufacturing process in which materials are joined together in a process that repeatedly builds one layer on top of another to generate a three-dimensional structure or object. Additive manufacturing may also be referred to using different terms including: additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a cutting guide that is attachable to one or more bones, with one or more guide features that facilitate resection of the one or more bones pursuant to a procedure such as arthroplasty or arthrodesis. In some embodiments, performance of the step 106 may include modelling an instrument with a bone apposition surface that is shaped to match the contour of a surface of the bone, such that the bone apposition surface can lie directly on the corresponding contour.

As used herein, a "resection" refers to a method, procedure, or step that removes tissue from another anatomical structure or body. A resection is typically performed by a surgeon on a part of a body of a patient. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

As used herein, a "guide" refers to a part, component, or structure designed, adapted, configured, or engineered to guide or direct one or more other parts, components, or structures. A guide may be part of, integrated with, connected to, attachable to, or coupled to, another structure. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, and the like. As used herein, "feature" refers to a distinctive attribute or aspect of something. (Search "feature" on google.com. Oxford Languages, 2021. Web. 20 Apr. 2021.) A feature may include a modifier that identifies a particular function or operation and/or a particular structure relating to the feature. Examples of such modifiers applied to a feature, include, but are not limited to, "attachment feature," "securing feature," "protruding feature," "engagement feature," "disengagement feature," "guide feature", and the like.

Those of skill in the art will appreciate that a guide feature may take a variety of forms and may include a single feature or one or more features that together form the guide feature. In certain embodiments, the guide feature may take the form of one or more slots. Alternatively, or in addition, a guide feature may be referenced using other names including, but not limited to, channel, cut channels, and the like.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a cutting guide with the bone apposition surface and one or more guide features as described above.

In addition to, or in the alternative to the step 108, the model(s) may be used to select from available sizes of implants and/or instruments and advise the surgeon accordingly. For example, where a range of cutting guides are available for a given procedure, analysis of the CAD data may facilitate pre-operative selection of the optimal cutting guide and/or optimal placement of the cutting guide on the bone. Similarly, if a range of implants may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may be provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may entail placing the modelled bone apposition surface against the corresponding contour of the bone used to obtain its shape, and then using the guide feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, advanced computer analysis, machine learning and automated/artificial intelligence may be used to generate a CAD model and/or one or more patient-specific instruments and/or operation plans. For example, a patient-specific cutting guide may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g. one or more bones of a patient's foot). Next, the patient-specific cutting guide and the patient-specific synthetic cadaver can be provided to a surgeon who can then rehearse an operation procedure in full before going into an operating room with the patient.

In certain embodiments, the patient-specific cutting guide can be used to preposition and pre-drill a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of the cut through the patient-specific cutting guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific cutting guide and/or implant. The details for such lengths, trajectories, and components can be detailed in a report provided to the surgeon preparing to do a procedure.

FIG. 1B is a flowchart diagram depicting a method 120 for correcting bunion deformity of the human foot, according to one embodiment. The method 120 may be used to carry out an arthrodesis procedure by which the first metatarsocuneiform joint is removed and the first cuneiform and first metatarsal are secured together in a manner that properly aligns the first metatarsal, providing correction of the deformity.

As shown, the method 120 may begin with a step 122 in which a CT scan (or another three-dimensional image) of the patient's foot is obtained. The step 122 may entail capturing a scan of only the first cuneiform and first metatarsal, or may entail capture of additional anatomic information, such as the entire foot. Additionally or alternatively, the step 122 may entail receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct the bunion deformity. Such instrumentation may include a cutting guide that is attachable to the first cuneiform and the first metatarsal, with two guide features that facilitate resection of the cuneiform and the metatarsal in preparation for arthrodesis. In some embodiments, performance of the step 126 may include modelling the cutting guide with a bone apposition surface that is shaped to match contours of the surfaces of the cuneiform and the metatarsal, such that the bone apposition surface can lie directly on the corresponding contours of the first cuneiform and the first metatarsal.

In a step 128, the model(s) may be used to manufacture patient-specific instrumentation and/or instruments. This may include manufacturing the cutting guide with the bone apposition surface and the guide features as described above. As in the step 108, the step 128 may additionally or alternatively involve provision of one or more instruments and/or implants from among a plurality of predetermined configurations or sizes. Further, the step 128 may additionally or alternatively involve provision of instructions for placement and/or anchorage of one or more instruments and/or instruments to carry out the procedure.

In a step 130, the manufactured cutting guide may be used in surgery to facilitate treatment of the condition. Specifically, the bone apposition surface of the cutting guide may be placed against the corresponding contours of the first cuneiform and the first metatarsal. The guide features (for example, slots) may then be positioned on either side of the joint between the first cuneiform and the first metatarsal to guide resection of the first metatarsal and the first cuneiform to remove the intervening joint. The cutting guide may then be removed, and the remaining portions of the first cuneiform and the first metatarsal may be placed to abut each other. The cutting guide may have been shaped such that the cuts made to the first cuneiform and the first metatarsal are properly oriented to bring the first metatarsal back into its proper orientation relative to the rest of the foot. The first cuneiform and the first metatarsal may be secured together using a bone plate or the like. The surgical wound may be closed to allow the foot to heal, and to allow the first cuneiform and the first metatarsal to fuse together.

The method 100 and the method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with FIGS. 2 through 7D. Those of skill in the art will recognize that the method 120 may be used in connection with different instruments; likewise, the instruments of FIGS. 2 through 7D may be used in connection with methods different from the method 100 and the method 120.

Figure 2:
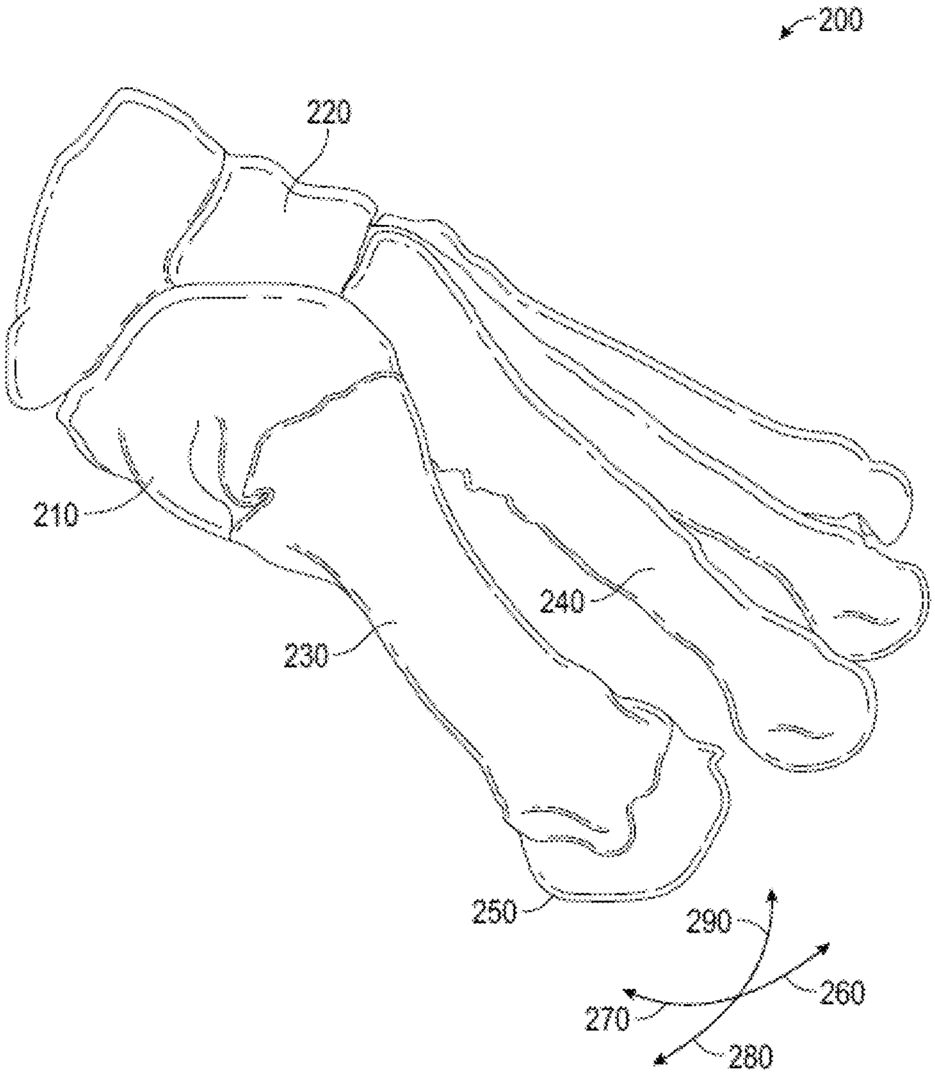
FIG. 2 is a perspective view of a portion of a foot with a bunion deformity to be treated through use of the methods of FIGS. 1A and/or 1B, according to one embodiment.
Figure 3A:
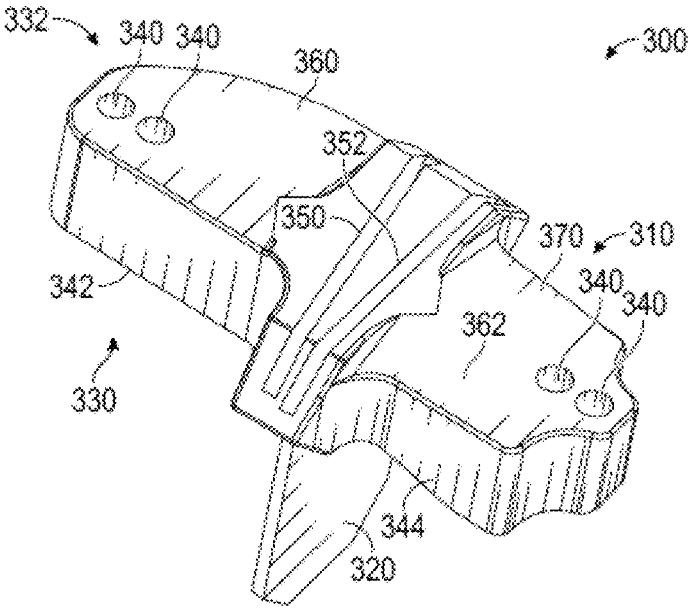
FIGS. 3A, 3B, 3C, and 3D are top perspective, alternative top perspective, front elevation, and bottom perspective views, respectively, of a patient-specific cutting guide, according to one embodiment
Figure 3B:
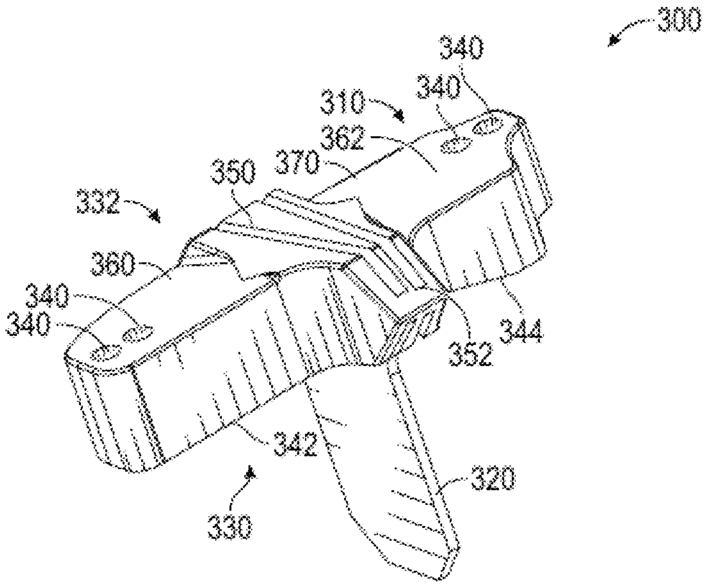
Figure 3C:
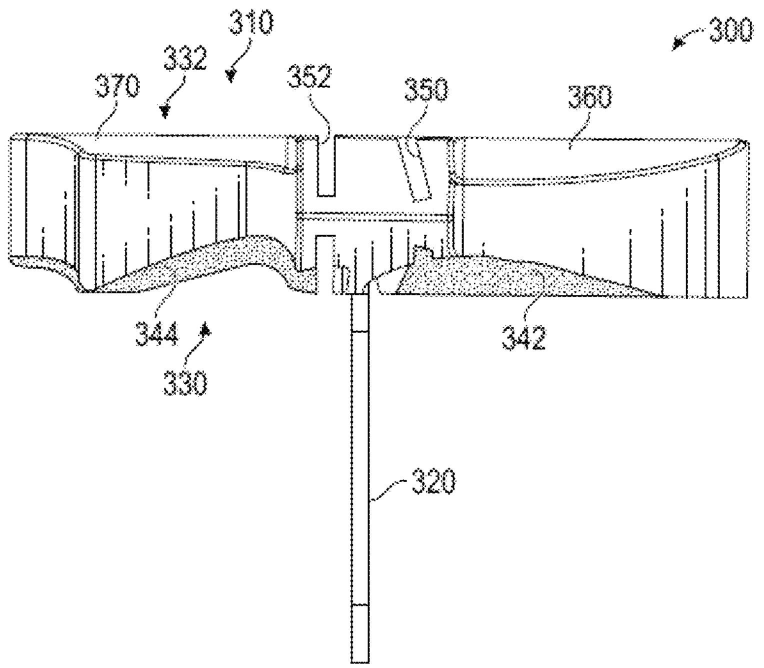
Figure 3D:
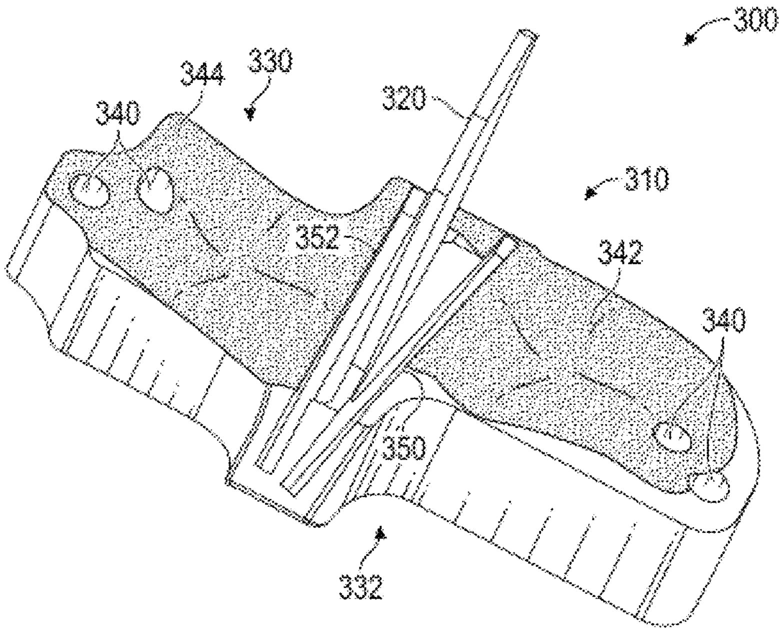

FIG. 2 is a perspective view of a portion of a foot 200 with a bunion deformity to be treated through use of the method 100 (and more specifically, the method 120) described above. The foot 200 may have a first cuneiform 210, a second cuneiform 220, a first metatarsal 230, and a second metatarsal 240. The first cuneiform 210 and the second cuneiform 220 may be joined together at a first metatarsocuneiform joint, and the first metatarsal 230 and the second metatarsal 240 may be joined together at a second metatarsocuneiform joint.

The first metatarsal 230 may be excessively angled in a medial direction 270 (i.e., toward the lower left-hand corner of the page), causing a painful protrusion at a distal end 250 of the first metatarsal 230, and further causing the phalanges (not shown) attached to the distal end 250 to be angled excessively in a lateral direction 260 (i.e., pointing toward the other phalanges of the foot, rather than pointing directly forward). The excessive medial angulation of the first metatarsal 230 may also result in an excessive gap between the first metatarsal 230 and the second metatarsal 240.

The first metatarsal 230 may further be offset in a plantar direction 280 or in a dorsal direction 290, relative to the remainder of the foot 200. Accordingly, the orientation of the first metatarsal 230 may need to be adjusted to move the distal end 250 in the lateral direction 260 and in the plantar direction 280 and/or in the dorsal direction 290.

Every deformity is different; accordingly, the degree of angular adjustment needed in each direction may be different for every patient. Use of a patient-specific cutting guide may help the surgeon obtain the optimal realignment in the lateral direction 260 and in the plantar direction 280 or the dorsal direction 290. Conversely, use of one of several differently-sized cutting guides may provide only approximate correction, as the surgeon may not have a guide that precisely matches the correction needed for the foot 200, and must thus choose the cutting guide that most closely provides the desired correction. Such differently sized cutting guides would not be contoured to fit the first cuneiform 210 or the first metatarsal 230, thus introducing additional potential for error as the surgeon must properly align the selected cutting guide.

Thus, providing a patient-specific cutting guide may provide unique benefits. Specifically, the patient-specific cutting guide may provide precise correction of the deformity present in the foot 200 and may also reduce the likelihood of improper correction due to misalignment of the cutting guide on the foot 200. The optimal cut provided by such a cutting guide may further reduce the likelihood that additional procedures, such as attachment of the first metatarsal 230 to the second metatarsal 240 to each other with screws or the like, will be needed to provide the desired correction. Any such additional procedure carries its own added surgical burden and risk of failure. Thus, the use of patient-specific instrumentation may shorten surgery, accelerate recovery, and reduce the risk of complications.

FIGS. 3A, 3B, 3C, and 3D are top perspective, alternative top perspective, front elevation, and bottom perspective views, respectively, of a patient-specific cutting guide, or cutting guide 300, according to one embodiment. The cutting guide 300 may be designed to facilitate resection of the first cuneiform 210 and the first metatarsal 230 with planar cuts at the proper angles to provide dual-plane correction of the orientation of the first metatarsal 230, thereby providing correction in the lateral direction 260 and in the plantar direction 280 or the dorsal direction 290.

As shown, the cutting guide 300 may have a body 310 with a monolithic construction and the general shape of a rectangular prism. The cutting guide 300 may further have a joint alignment feature that helps align the body 310 with the metatarsocuneiform joint between the first cuneiform 210 and the first metatarsal 230. The joint alignment feature may consist of a joint probe 320 that extends from the body 310 and has a blade-like shape. The body 310 may reside on the dorsal surfaces of the first cuneiform 210 and the first metatarsal 230, while the joint probe 320 may protrude into the metatarsocuneiform joint between the first cuneiform 210 and the first metatarsal 230 to provide proper alignment of the body 310 with the metatarsocuneiform joint.

The body 310 may have a bone facing side 330 that, upon attachment of the body 310 to the first cuneiform 210 and the first metatarsal 230, is to face toward the first cuneiform 210 and the first metatarsal 230. The body 310 may also have an outward-facing side 332 that, upon attachment of the body 310 to the first cuneiform 210 and the first metatarsal 230, faces outward, away from the first cuneiform 210 and the first metatarsal 230. Further, the body 310 may have one or more bone attachment features that facilitate attachment of the body 310 to the first cuneiform 210 and/or the first metatarsal 230. Such bone attachment features may comprise any of a wide variety of holes, spikes, fastening devices, and/or the like. As embodied in FIGS. 3A through 3D, the bone attachment features may take the form of holes 340 that extend from the bone facing side 330 to the outward-facing side 332 and/or one or more fixation devices. The holes 340 may be shaped to accommodate pins, K-wires, and/or other elongated bone fixation elements that can be anchored in the first cuneiform 210 and/or the first metatarsal 230 to keep the cutting guide 300 in place.

The bone facing side 330 may be custom contoured to match the shapes of the first cuneiform 210 and/or the first metatarsal 230. As embodied in FIGS. 3A through 3D, the bone facing side 330 may have a cuneiform apposition portion 342 shaped to lie against the dorsal surface of the first cuneiform 210, and a metatarsal apposition portion 344 shaped to lie against the dorsal surface of the first metatarsal 230. As shown, the cuneiform apposition portion 342 may be contoured to match the contour of the dorsal surface of the first cuneiform 210 on which it is to rest, and the metatarsal apposition portion 344 may similarly be contoured to match the contour of the dorsal surface of the first metatarsal 230 on which it is to rest. Thus, the body 310 may have only one stable position and orientation relative to the first cuneiform 210 and the first metatarsal 230.

Generation of the contours of the cuneiform apposition portion 342 and the metatarsal apposition portion 344 may be performed relative easily in various CAD programs. In some embodiments, the shapes of the corresponding dorsal surfaces of the first cuneiform 210 and the first metatarsal 230 may be obtained directly from the CAD models and/or CT scan data, and simply copied onto the model for the body 310 of the cutting guide 300. Various operations may be used to copy surfaces from one object to another. Additionally or alternatively, various Boolean operations, such as a Boolean subtraction operation, may be used to remove material from a model for the body 310 with a shape that matches the dorsal surfaces of the first cuneiform 210 and the first metatarsal 230.

The body 310 may further have guide features that guide a cutter to resect the first cuneiform 210 and the first metatarsal 230 in the manner needed to make the desired correction. For example, the guide features may be used to guide a planar cutting blade, an arcuate cutting blade, a drill or mill, a burr, and/or the like.

In the embodiment of FIGS. 3A through 3D, the guide features may guide a reciprocating planar blade, such as that of a surgical bone saw, that forms planar cuts in the first cuneiform 210 and the first metatarsal 230. Thus, the guide features may take the form of a first slot 350 and a second slot 352, which may be positioned toward the center of the body 310, on opposite sides of the joint probe 320. Thus, upon proper positioning of the cutting guide 300, the first slot 350 may be positioned over the first cuneiform 210 to facilitate resection of the first cuneiform 210, while the second slot 352 may be positioned over the first metatarsal 230 to facilitate resection of the first metatarsal 230.

In alternative embodiments, a guide feature may be designed to guide a different type of cutter, such as a drill, mill, or side-cutting burr. In such embodiments, the guide feature may not be a slot, but may instead be a translatable or rotatable cutter retainer that guides translation and/or rotation of the cutter relative to the bone.

Returning to FIGS. 3A through 3D, the body 310 may further have features that facilitate proper positioning of the cutting guide 300 on the first cuneiform 210 and the first metatarsal 230. More specifically, the body 310 may have a first bone indicator 360 with the text "CUN," indicating that the end of the body 310 with the first bone indicator 360 is to be positioned over the first cuneiform 210. Similarly, the body 310 may have a second bone indicator 362 with the text "MET," indicating that the end of the body 310 with the second bone indicator 362 is to be positioned over the first metatarsal 230. In addition, the body 310 may have a side indicator 370 with the text "LEFT," indicating that the cutting guide 300 is to be used in connection with the patient's left foot. The side indicator 370 may be particularly helpful when bunion corrections are to be provided on both of the patient's feet. In such a case, the surgeon may manufacture or receive two separate cutting guides: one for the left foot (the foot 200 of FIG. 2) and another for the right foot (not shown).

Figure 4:
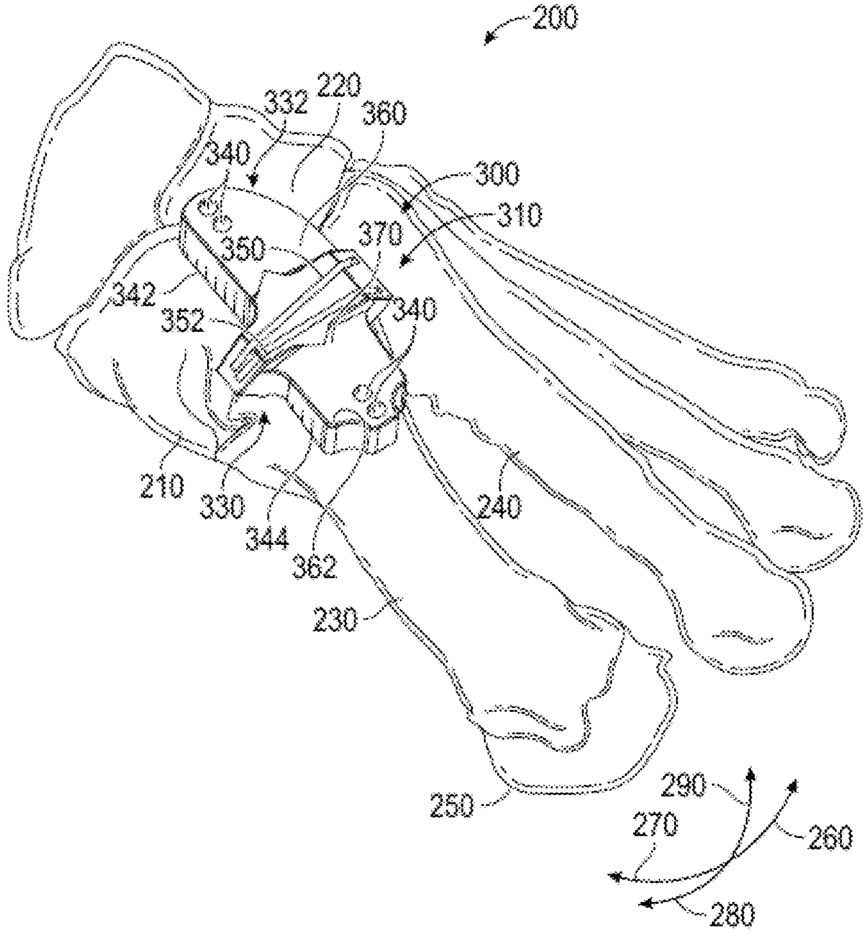
FIG. 4 is a perspective view of the foot of FIG. 2, with the cutting guide of FIGS. 3A, 3B, 3C and 3D properly positioned on the first cuneiform and the first metatarsal, but as yet not attached to the first cuneiform and the first metatarsal.

FIG. 4 is a perspective view of the foot 200 of FIG. 2, with the cutting guide 300 of FIGS. 3A, 3B, 3C and 3D properly positioned on the first cuneiform 210 and the first metatarsal 230, but as yet not attached to the first cuneiform 210 and the first metatarsal 230. The surgeon has made the incision(s) to expose the dorsal surfaces of the first cuneiform 210 and the first metatarsal 230, and has inserted the cutting guide 300 such that the cuneiform apposition portion 342 (identified by the first bone indicator 360 on the outward-facing side 332 of the body 310) is resting on the corresponding dorsal surface of the first cuneiform 210, and the metatarsal apposition portion 344 (identified by the second bone indicator 362 on the outward-facing side 332 of the body 310) is resting on the corresponding dorsal surface of the first metatarsal 230. Since the cuneiform apposition portion 342 and the metatarsal apposition portion 344 are contoured to match the bone surfaces on which they rest, the body 310 may readily slide into its proper position on the first cuneiform 210 and the first metatarsal 230.

Notably, the joint probe 320 (not visible) may reside between the first cuneiform 210 and the first metatarsal 230 (i.e., distal to the first cuneiform 210 and proximal to the first metatarsal 230). The surgeon may need to cut the metatarsocuneiform joint between the first cuneiform 210 and the first metatarsal 230 to form a space between the first cuneiform 210 and the first metatarsal 230 to receive the joint probe 320. Positioning the joint probe 320 in this space may further help to ensure that the cutting guide 300 is properly aligned relative to the first cuneiform 210 and the first metatarsal 230.

Figure 5:
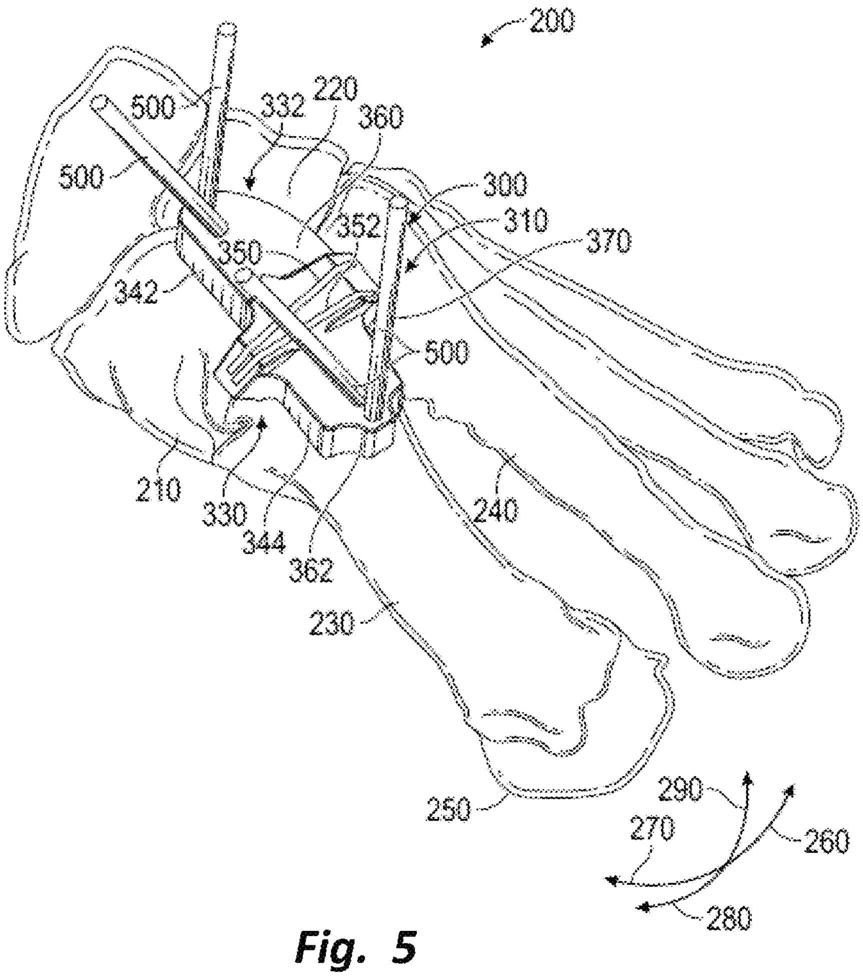
FIG. 5 is a perspective view of the foot of FIG. 2, with the cutting guide of FIGS. 3A, 3B, 3C, and 3D properly positioned on the first cuneiform and the first metatarsal and attached to the first cuneiform and the first metatarsal in preparation for resection of the first cuneiform and the first metatarsal, according to one embodiment.

FIG. 5 is a perspective view of the foot 200 of FIG. 2, with the cutting guide 300 of FIGS. 3A, 3B, 3C, and 3D properly positioned on the first cuneiform 210 and the first metatarsal 230 and attached to the first cuneiform 210 and the first metatarsal 230 in preparation for resection of the first cuneiform 210 and the first metatarsal 230. Specifically, pins 500 may be inserted through the holes 340 in the body 310 and anchored in the first cuneiform 210 and the first metatarsal 230. Each of the pins 500 may have a sharp and/or threaded distal end that can penetrate and/or readily be retained in the bone of the first cuneiform 210 or the first metatarsal 230. Additionally or alternatively, a drill or other hole-forming instrument may be used to pre-form holes in the first cuneiform 210 and/or the first metatarsal 230 to receive the distal ends of the pins 500.

As shown, the body 310 may have two holes 340 positioned over the first cuneiform 210, and two holes 340 positioned over the first metatarsal 230. This is merely exemplary; in some embodiments, a cutting guide may be secured to one of the first cuneiform 210 and the first metatarsal 230 or may be secured to either of the first cuneiform 210 and the first metatarsal 230 with one pin 500, or with more than two pins 500. Further, in some alternative embodiments, different fasteners may be used, such as screws, clamps, clips, and/or the like.

Once the cutting guide 300 has been secured relative to the first cuneiform 210 and the first metatarsal 230, the first cuneiform 210 and the first metatarsal 230 may be resected. In some embodiments, a reciprocating blade may be inserted into the first slot 350 and moved medially and laterally, between opposite ends of the first slot 350, to make a planar cut that removes the distal end of the first cuneiform 210. Similarly, the reciprocating blade (or a different reciprocating blade) may be inserted into the second slot 352 and moved medially and laterally, between opposite ends of the second slot 352, to make a planar cut that removes the proximal end of the first metatarsal 230. The cuts in the first cuneiform 210 and the first metatarsal 230 may be made in either order. In either case, once both cuts are made, the metatarsocuneiform joint between the first cuneiform 210 and the first metatarsal 230 may be removed, resulting in exposure of "bleeding" bone at the distal end of the first cuneiform 210 and the proximal end of the first metatarsal 230. The cutting guide 300 may be removed, along with some or all of the pins 500. If desired, at least two of the pins 500 may remain in place and used to attach a distractor (not shown) to the first cuneiform 210 and the first metatarsal 230, such that the distractor can temporarily widen the space between the first cuneiform 210 and the first metatarsal 230 to allow for fenestration and/or other preparation of the cut surfaces of the first cuneiform 210 and the first metatarsal 230. Once such preparation has been carried out, the remaining pins 500 may also be removed.

The resulting bleeding and/or prepared bone may readily grow together and fuse, upon abutment of the distal end of the first cuneiform 210 to the proximal end of the first metatarsal 230, particularly with application of some compression across the juncture of the two bones. Since the positions and orientations of the first slot 350 and the second slot 352 were carefully selected to provide the proper correction, the first metatarsal 230 may be positioned to abut the first cuneiform 210, resulting in reorientation of the first metatarsal 230 to a desired orientation, relative to the lateral direction 260 and the plantar direction 280 and/or the dorsal direction 290. Further, the surgeon may optionally rotate the first metatarsal 230, relative to the first cuneiform 210, about an axis perpendicular to the cutting planes, if desired.

Figure 6A:
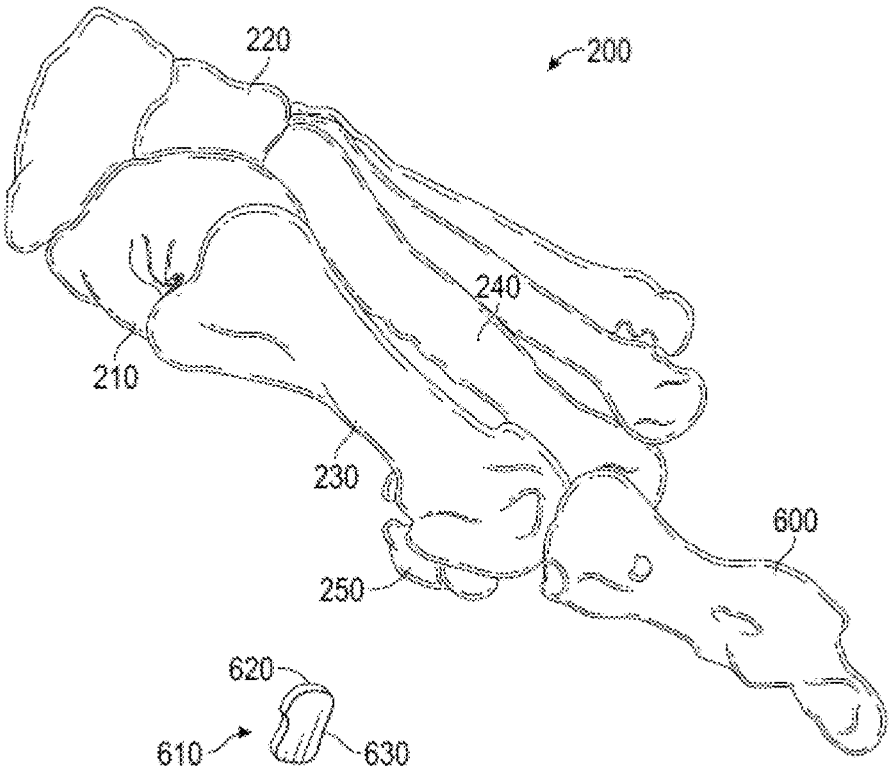
FIG. 6A is a perspective view of the foot of FIG. 2, after resection of the first cuneiform and the first metatarsal, removal of the cutting guide, and placement of the first metatarsal to abut the first cuneiform, according to one embodiment.

FIG. 6A is a perspective view of the foot 200 of FIG. 2, after resection of the first cuneiform 210 and the first metatarsal 230, removal of the cutting guide 300, and placement of the first metatarsal 230 to abut the first cuneiform 210. As shown, the distal end 250 of the first metatarsal 230 may now be positioned much closer to the second metatarsal 240, in a more natural position. Further, FIG. 6A depicts a first proximal phalanx 600, which may now be properly oriented generally parallel to the other phalanges (not shown), rather than pointing in the lateral direction 260. If desired, further steps may be performed relative to the joint between the first metatarsal 230 and the first proximal phalanx 600 in order to keep them in the proper relative orientation. The distal end 250 may also have been shifted in the plantar direction 280 or in the dorsal direction 290 from the position of FIG. 2. Thus, the desired dual-plane correction of the orientation of the first metatarsal 230 may be complete.

The first metatarsal 230 may be secured to the first cuneiform 210, at least until proper bone in-growth has occurred between the first cuneiform 210 and the first metatarsal 230. In some embodiments, a bone plate (not shown) or other fastener (not shown) may be used to secure the first cuneiform 210 and the first metatarsal 230 together. Additional hardware (not shown) may be used to stabilize the position and/or orientation of the first proximal phalanx 600 relative to the first metatarsal 230, if desired. The surgical wound may be closed, and the foot 200 may be allowed to heal with the bunion deformity corrected.

Figure 6B:
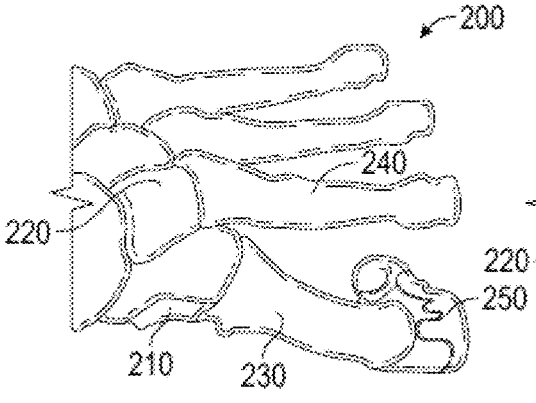
FIGS. 6B and 6C are dorsal views of the foot of FIG. 2, before and after correction, respectively, according to one embodiment.
Figure 6C:
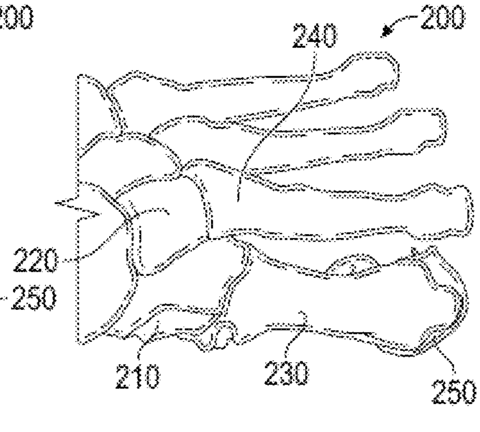
Figure 7A:
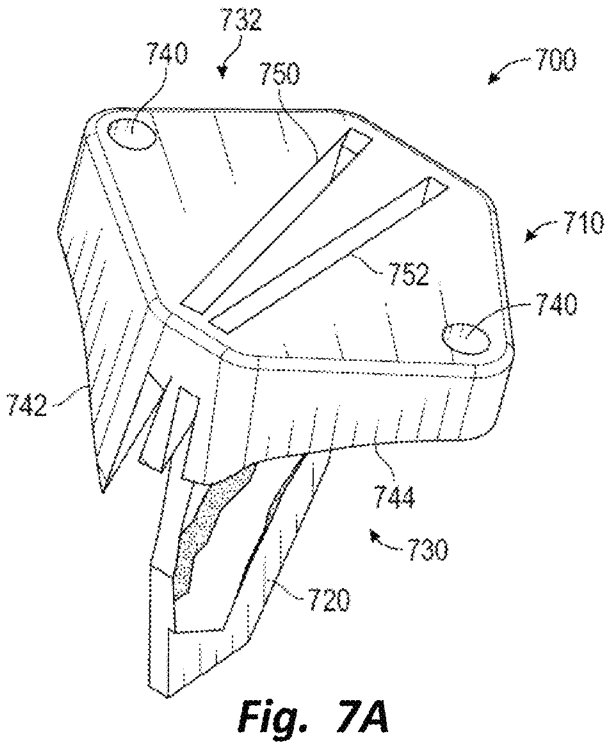
FIGS. 7A, 7B, 7C, and 7D are top perspective, alternative top perspective, front elevation, and bottom perspective views, respectively, of a patient-specific cutting guide according to one alternative embodiment.
Figure 7B:
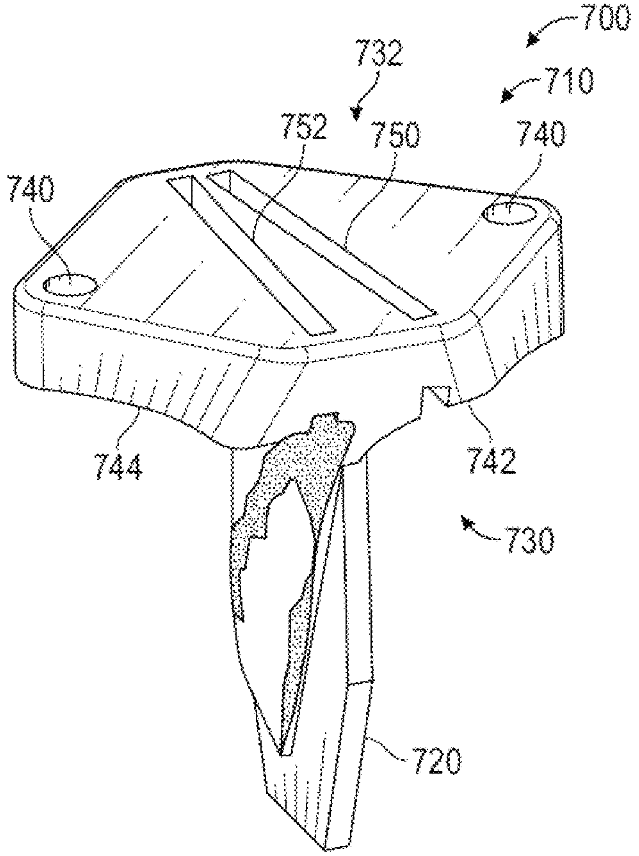
Figure 7C:
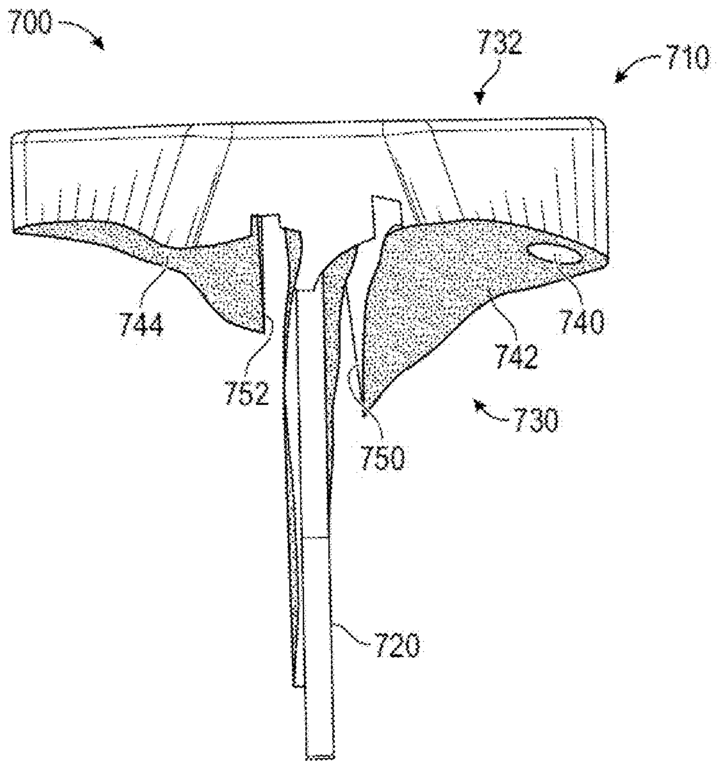
Figure 7D:
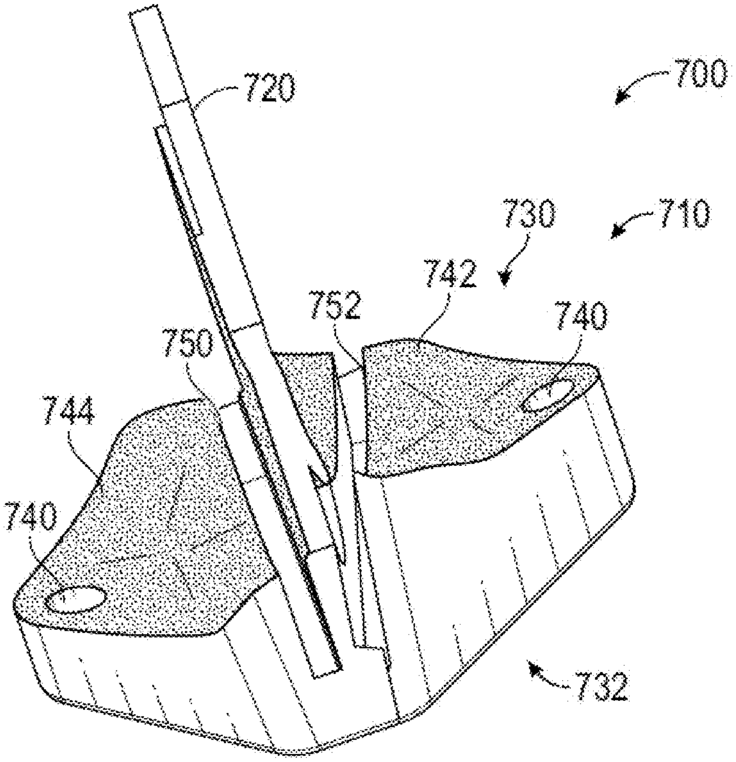

FIGS. 6B and 6C are dorsal views of the foot 200, before and after correction, respectively. FIGS. 6B and 6C illustrate the correction of the angulation of the first metatarsal 230, by which the distal end 250 of the first metatarsal 230 is moved in the lateral direction 260. In some embodiments, an implant 610 may be inserted in the space between the first metatarsal 230 and the first cuneiform 210 in order hold the first metatarsal 230 and the first cuneiform 210 together and/or facilitate bony fusion between the first metatarsal 230 and the first cuneiform 210.

In some embodiments, the implant 610 may be patient-specific. For example, the implant 610 may have a cuneiform-facing side 620 that is shaped and/or sized to be secured to the adjoining, resected surface of the first cuneiform 210, and a metatarsal-facing side 630 that is shaped and/or sized to be secured to the adjoining, resected surface of the first metatarsal 230. As the resections made to the first metatarsal 230 and the first cuneiform 210 may both planar, the cuneiform-facing side 620 and/or the metatarsal-facing side 630 may also be planar. However, the cuneiform-facing side 620 and/or the metatarsal-facing side 630 may advantageously each be shaped to match the profile of the resected surface of the first cuneiform 210 and the first metatarsal 230, respectively.

This shaping may be accomplished by custom-designing the implant 610 for the patient, using the same models (for example, from CT scans) of the first metatarsal 230 and the first cuneiform 210 that were used to generate the cutting guide 300. Thus, the implant 610 may have a shape that provides secure attachment and/or fusion between the first metatarsal 230 and the first cuneiform 210 while avoiding proud edges or other protruding features that could otherwise interfere with surrounding tissues.

As indicated previously, the cutting guide 300 is one of many patient-specific instruments that may be used in connection with the method 100 and/or the method 120. An alternative cutting guide suitable for use with the method 120 will be shown and described in connection with FIGS. 7A, 7B, 7C, and 7D.

FIGS. 7A, 7B, 7C, and 7D are top perspective, alternative top perspective, front elevation, and bottom perspective views, respectively, of a patient-specific cutting guide, or cutting guide 700, according to one alternative embodiment. The cutting guide 700 may be used to correct a bunion deformity, such as that of the foot 200 of FIG. 2. Thus, the cutting guide 700 may also be designed to facilitate resection of the first cuneiform 210 and the first metatarsal 230 with planar cuts at the proper angles to provide dual-plane correction of the orientation of the first metatarsal 230, thereby providing correction in the lateral direction 260 and in the plantar direction 280 or the dorsal direction 290.

As shown, the cutting guide 700 may have a body 710 with a monolithic construction and the general shape of a rectangular prism. The cutting guide 700 may further have a joint alignment feature that helps align the body 710 with the metatarsocuneiform joint between the first cuneiform 210 and the first metatarsal 230. The joint alignment feature may consist of a joint probe 720 that extends from the body 710 and has a blade-like shape. The body 710 may reside on the dorsal surfaces of the first cuneiform 210 and the first metatarsal 230, while the joint probe 720 may protrude into the metatarsocuneiform joint between the first cuneiform 210 and the first metatarsal 230 to provide proper alignment of the body 710 with the metatarsocuneiform joint. Notably, the joint probe 720 may have surfaces that are not simply planar, but rather have some contouring by which the shape of the joint probe 720 is matched to the adjoining surfaces of the first cuneiform 210 and/or the first metatarsal 230. Such contouring of the joint probe 720 may enable more precise alignment of the body 710 with the metatarsocuneiform joint.

The body 710 may have a bone facing side 730 that, upon attachment of the body 710 to the first cuneiform 210 and the first metatarsal 230, is to face toward the first cuneiform 210 and the first metatarsal 230. The body 710 may also have an outward-facing side 732 that, upon attachment of the body 710 to the first cuneiform 210 and the first metatarsal 230, faces outward, away from the first cuneiform 210 and the first metatarsal 230. Further, the body 710 may have one or more bone attachment features that facilitate attachment of the body 710 to the first cuneiform 210 and/or the first metatarsal 230. Such bone attachment features may comprise any of a wide variety of holes, spikes, fastening devices, and/or the like. As embodied in FIGS. 7A through 7D, the bone attachment features may take the form of holes 740 that extend from the bone facing side 330 to the outward-facing side 332 and/or one or more fixation devices. The holes 340 may be shaped to accommodate pins, K-wires, and/or other elongated bone fixation elements that can be anchored in the first cuneiform 210 and/or the first metatarsal 230 to keep the cutting guide 700 in place. As embodied in FIGS. 7A through 7D, only one hole 340 may be present on each side of the body 710. Thus, the body 710 may be secured to the first cuneiform 210 with only a single pin or K-wire (not shown) and to the first metatarsal 230 with only another single pin or K-wire (not shown).

The bone facing side 730 may be custom contoured to match the shapes of the first cuneiform 210 and/or the first metatarsal 230. As embodied in FIGS. 7A through 7D, the bone facing side 730 may have a cuneiform apposition portion 742 shaped to lie against the dorsal surface of the first cuneiform 210, and a metatarsal apposition portion 744 shaped to lie against the dorsal surface of the first metatarsal 230. As shown, the cuneiform apposition portion 742 may be contoured to match the contour of the dorsal surface of the first cuneiform 210 on which it is to rest, and the metatarsal apposition portion 744 may similarly be contoured to match the contour of the dorsal surface of the first metatarsal 230 on which it is to rest. Thus, the body 710 may have only one stable position and orientation relative to the first cuneiform 210 and the first metatarsal 230. Alternatively, or in addition, the cuneiform apposition portion 742 may be contoured to match the contour of a surface that is between the dorsal surface and a medial or lateral surface and/or the surface includes at least a portion of the dorsal surface of the first cuneiform 210 on which it is to rest, and the metatarsal apposition portion 744 may similarly be contoured to match the contour of a surface that is between the dorsal surface and a medial or lateral surface and/or the surface includes at least a portion of the dorsal surface of the dorsal surface of the first metatarsal 230.

In certain embodiments, the topography of the articular surfaces of a joint may not factor into the form and/or shape of the cuneiform apposition portion 742 and/or the metatarsal apposition portion 744 because those parts of the bones will be resected during the procedure. Alternatively, or in addition, the topography of the articular surfaces of a joint may be factored into the form and/or shape of the cuneiform apposition portion 742 and/or the metatarsal apposition portion 744 even though those parts of the bones will be resected during the procedure.

Like the cuneiform apposition portion 342 and the metatarsal apposition portion 344 of the cutting guide 300, generation of the contours of the cuneiform apposition portion 742 and the metatarsal apposition portion 744 may be performed relative easily in various CAD programs through surface copy operations, Boolean operations, and/or the like.

The body 710 may further have guide features that guide a cutter to resect the first cuneiform 210 and the first metatarsal 230 in the manner needed to make the desired correction. For example, the guide features may be used to guide a planar cutting blade, an arcuate cutting blade, a drill or mill, and/or the like.

In the embodiment of FIGS. 7A through 7D, the guide features may guide a reciprocating planar blade, such as that of a surgical bone saw, that forms planar cuts in the first cuneiform 210 and the first metatarsal 230. Thus, the guide features may take the form of a first slot 750 and a second slot 752, which may be positioned toward the center of the body 710, on opposite sides of the joint probe 720. Thus, upon proper positioning of the cutting guide 700, the first slot 750 may be positioned over the first cuneiform 210 to facilitate resection of the first cuneiform 210, while the second slot 752 may be positioned over the first metatarsal 230 to facilitate resection of the first metatarsal 230.

In operation, the cutting guide 700 may be used in a manner similar to that of the cutting guide 300. However, the cutting guide 700 may only be secured to each of the first cuneiform 210 and the first metatarsal 230 with a single pin or K-wire (not shown), as mentioned previously. Further, the cutting guide 700 is smaller than the cutting guide 300. Thus, the cutting guide 700 may be placed through a smaller, less invasive incision. One advantage to patient-specific instrumentation may be that instruments may be made smaller, since they are not limited to certain sizes. Many known instruments come in discrete sizes, each of which is designed to accommodate a range of patient anatomic dimensions. Thus, for given patient anatomy, the instrument must be large enough to treat the anatomy at either end of its range. This typically requires the instrument to be oversized for many anatomic dimensions it is designed to treat. Notably, the cutting guide 700 is merely one compact example; other cutting guides may be made even smaller; in some embodiments, cutting guides may be made that have a smaller width between holes (e.g., holes 740 on the cutting guide 700). As long as the holes are sufficiently far apart to avoid interference of the pins 500 with the operation of the cutting blade, the cutting guide may function appropriately. Thus, Lapidus and other procedures may be accomplished through a very narrow incision through the use of patient-specific instrumentation.

Those of skill in the art will recognize that a wide variety of differently configured cutting guides may be used in conjunction with the method 120 set forth above. Further, a wide variety of patient-specific instruments may be used in connection with the method 100, including but not limited to cutting guides, gages, implant positioning guides, joint distractors, joint compressors, soft tissue retractors, and the like. "Patient specific cutting guide" refers to a cutting guide designed, engineered, and/or fabricated for use with a specific patient. In one aspect, a patient specific cutting guide is unique to a single patient and may include features unique to the patient such as a surface contour or other features.

Furthermore, patient-specific cutting guides may be used for various other procedures on the foot, or on other bones of the musculoskeletal system. Patient-specific cutting guides may be used for various procedures involving osteotomy, including but not limited to arthroplasty, fusion, and deformity correction procedures. According to one example, patient-specific cutting guides similar to the cutting guide 300 and the cutting guide 700 may be used for the metatarsophalangeal ("MTP") joint. A method similar to the method 100 may be employed.

In some embodiments, one or more articulating surfaces of a joint may be replaced and/or resurfaced. For example, for the MTP joint, a patient-specific cutting guide may be used to determine the angles of cuts on the distal metatarsal or the proximal phalanx in preparation for replacement or resurfacing of the metatarsal head and/or the proximal phalangeal base. Implants for either the metatarsal or the phalanx may be customized to match the patient's original anatomy, such as the curvature of the MTP joint. In other embodiments, an MTP joint may be fused through the use of patient-specific cutting guides. Patient-specific cutting guides may be used to treat (for example, via fusion, resurfacing, and/or arthroplasty) any joint in the body, using methods similar to the method 100.

According to other examples, patient-specific cutting guides may be used to carry out an Evans calcaneal osteotomy and/or a medializing calcaneal osteotomy. Patient-specific instruments will be shown and described in connection with FIGS. 8A through 11, in relation to an Evans calcaneal osteotomy, and a medializing calcaneal osteotomy.

As used herein, "osteotomy procedure" or "surgical osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.) As used herein, "patient specific osteotomy procedure" refers to an osteotomy procedure that has been adjusted, tailored, modified, or configured to specifically address the anatomy, physiology, condition, abnormalities, needs, or desires of a particular patient. In certain aspects, one patient specific osteotomy procedure may be useable in connection with only one patient. In other aspects, one patient specific osteotomy procedure may be useable with a number of patients having a particular class of characteristics.

Figure 8A:
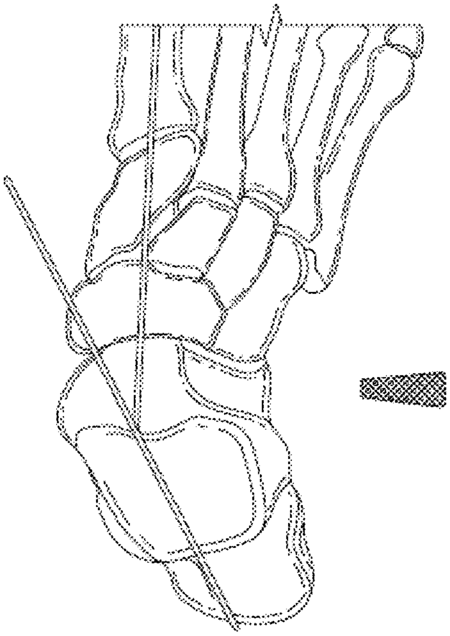
FIGS. 8A, 8B, and 8C are dorsal pre-operative, dorsal post-operative, and lateral post-operative views, respectively, of a foot treated with an Evans calcaneal osteotomy, according to one embodiment.
Figure 8B:
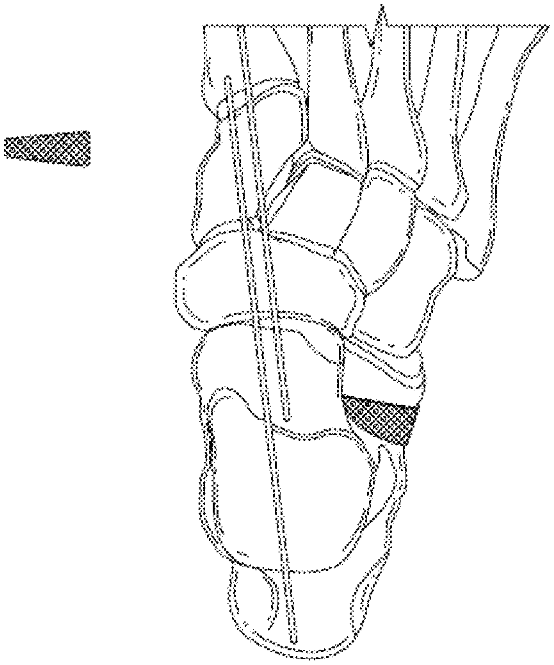
Figure 8C:
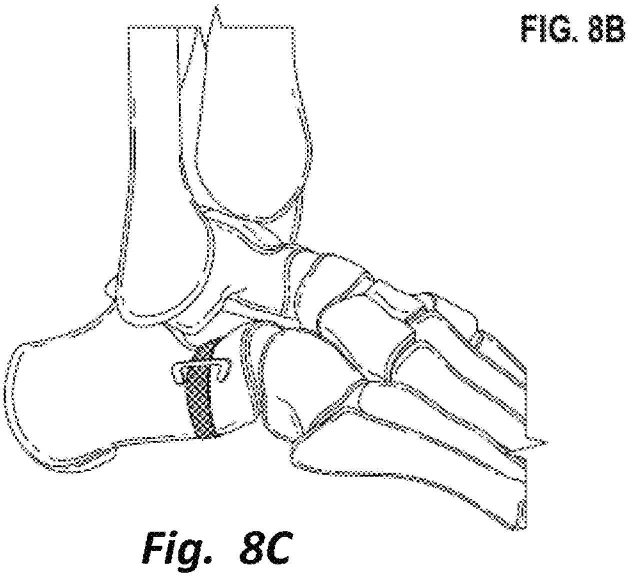

FIGS. 8A, 8B, and 8C are dorsal pre-operative, dorsal post-operative, and lateral post-operative views, respectively, of a foot treated with an Evans calcaneal osteotomy, according to one embodiment. Outward rotation of the foot may occur in patients with flatfoot. An Evans or lateral column lengthening procedure is sometimes performed for these patients. An incision is made on the outside of the foot, and the front half of the heel bone is cut. A bone wedge (typically either titanium or a bone-based graft) is then placed into the cut area of the heel bone. This wedge helps to "lengthen" the heel bone and rotate the foot back into its correct position. The wedge is usually kept in place using screws or a surgical staple.

Figure 9A:
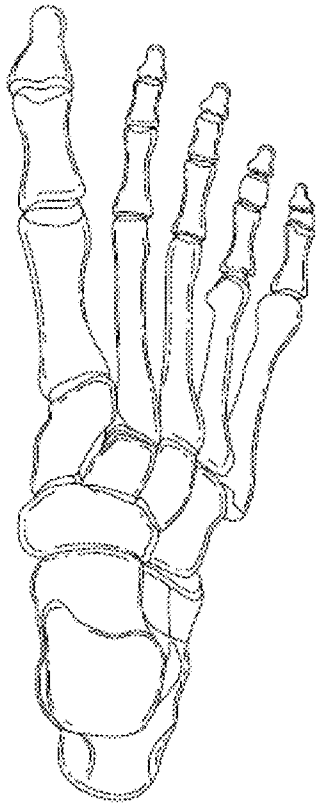
FIGS. 9A and 9B are dorsal post-operative and lateral post-operative views, respectively, of a foot treated with a medializing calcaneal osteotomy, according to one embodiment.
Figure 9B:
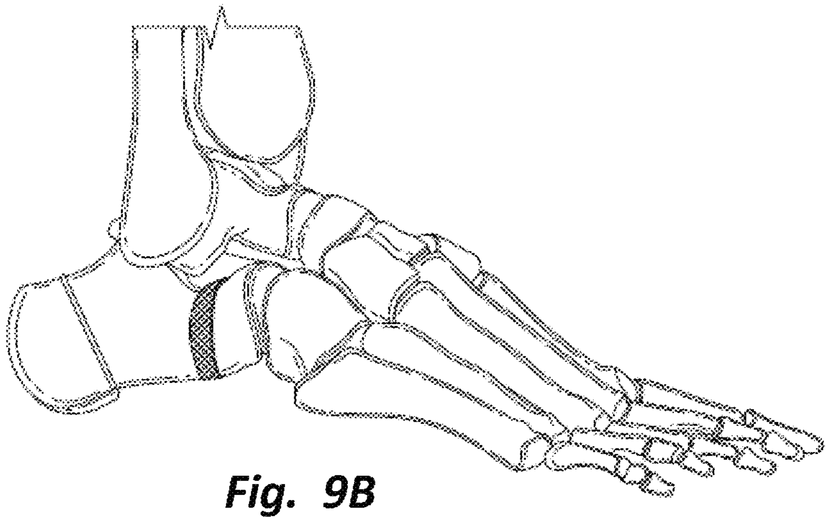

FIGS. 9A and 9B are dorsal post-operative and lateral post-operative views, respectively, of a foot treated with a medializing calcaneal osteotomy, according to one embodiment. A medializing calcaneal osteotomy (heel slide) procedure is often used when the calcaneus (heel bone) has shifted out from underneath the leg. An incision is made on the outside of the heel, and the back half of the heel bone is cut and slid back underneath the leg. The heel is then fixed in place using metal screws or a plate. This also helps to reposition the Achilles tendon towards the center of the ankle/rearfoot. The medializing calcaneal osteotomy can be used in place of, or in addition to, an Evans calcaneal osteotomy.

Figure 10:
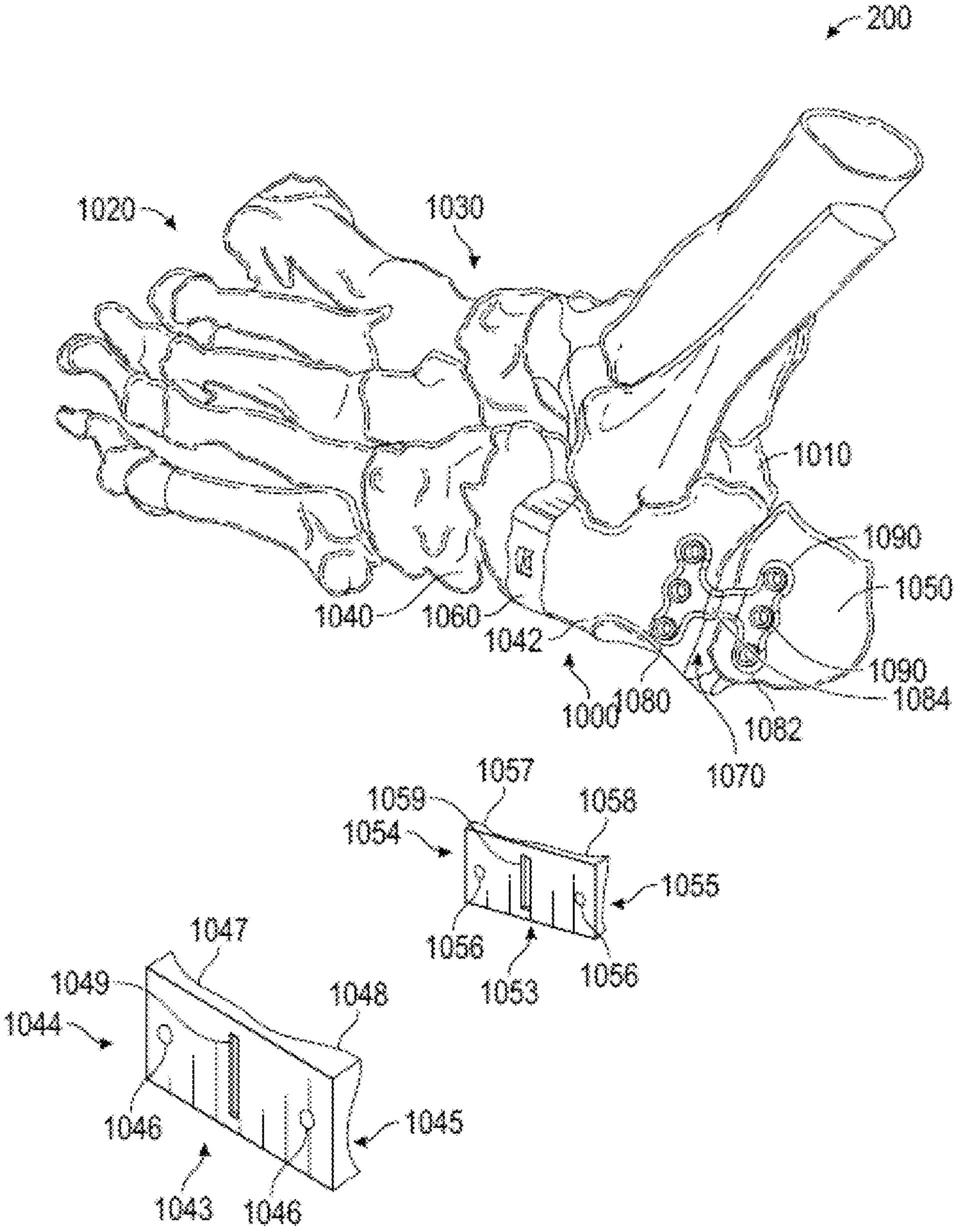
FIG. 10 is a rear, perspective view of the foot of FIG. 2, after performance of an Evans calcaneal osteotomy and a medializing calcaneal osteotomy with patient-specific instruments and/or implants, according to one embodiment.

FIG. 10 is a rear, perspective view of the foot 200 of FIG. 2, after performance of an Evans calcaneal osteotomy and a medializing calcaneal osteotomy with patient-specific instruments and/or implants, according to one embodiment. The foot 200 may have a calcaneus 1000 and a talus 1010, in addition to the metacarpals 1020 and cuneiforms 1030 depicted in FIG. 2. Pursuant to the Evans calcaneal osteotomy, an anterior portion of the calcaneus 1000 may be cut along the medial-lateral direction to separate a first bone segment 1040 of the calcaneus 1000 from a second bone segment 1042 of the calcaneus 1000. The second bone segment 1042 may be reoriented medially, relative to the first bone segment 1040, such that a heel 1050 of the calcaneus 1000 is moved medially, simulating a natural, healthy arch in the foot 200.

The cut between the first bone segment 1040 and the second bone segment 1042 may be carried out virtually (for example, in CAD) on a model of the calcaneus 1000 obtained from a CT scan or other imaging of the patient's foot. Thus, the optimal realignment of the posterior end of the calcaneus 1000 can be obtained. If desired, a patient-specific cutting guide, or cutting guide 1043, may be generated in order to facilitate resection of the calcaneus 1000.

As shown, the cutting guide 1043 may have a first end 1044 and a second end 1045, each of which has a bone attachment feature 1046. The bone attachment features 1046 may be used to secure the first end 1044 and the second end 1045 to the first bone segment 1040 and the second bone segment 1042, respectively. The first end 1044 may have a first bone engagement surface 1047 that is shaped to match a corresponding contour on the first bone segment 1040, and the second end 1045 may have a second bone engagement surface 1048 that is shaped to match a corresponding contour on the second bone segment 1042. Thus, the cutting guide 1043 may naturally lie flush with the surface of the calcaneus 1000, in the optimal position on the calcaneus 1000 to facilitate resection of the calcaneus 1000 to divide the first bone segment 1040 from the second bone segment 1042. The cutting guide 1043 may have a guide feature 1049, such as a slot, that can be used to guide a cutter to form a single cut between the first bone segment 1040 and the second bone segment 1042.

After the cut has been made to split the calcaneus 1000 into the first bone segment 1040 and the second bone segment 1042, the surgeon may angle the second bone segment 1042 relative to the first bone segment 1040 in the predetermined (previously modeled) relative orientation. This reorientation between the first bone segment 1040 and the second bone segment 1042 may leave a wedge-shaped gap between the first bone segment 1040 and the second bone segment 1042. In order to maintain the desired relative orientation, an implant 1060 with a wedge shape may be inserted into the gap and secured to the first bone segment 1040 and the second bone segment 1042. The implant 1060 may be fabricated specifically for the patient, since the precise angulation and position of the realignment may also be patient specific. As shown, the implant 1060 may have exterior surfaces that are contoured to match the contours of the adjoining portions of the first bone segment 1040 and the second bone segment 1042. Thus, the implant 1060 may provide secure fixation, while not protrude beyond the adjoining surfaces of the first bone segment 1040 and the second bone segment 1042. Thus, the implant 1060 may be devoid of proud edges or other protrusions that could otherwise interfere with motion between the calcaneus 1000 and the talus 1010, or with surrounding soft tissues, thus interfering with the patient's post-operative gait. "Soft tissue" refers to tissue of a patient (i.e., human or animal). Examples of soft tissue include but are not limited to skin, ligament, tendon, fascia, fat muscle, fibrous tissue, blood vessels, lymph vessels, brain tissue, and/or nerves.

The implant 1060 may be made of any biocompatible material, including but not limited to Titanium and alloys thereof, stainless steel, PEEK, and/or the like. The implant 1060 may be formed by any method known in the art, including but not limited to forging, casting, milling, additive manufacturing, and/or the like. In some embodiments, the implant 1060 may have an interior void that can be filled with bone graft or other material designed to promote boney in-growth between the cut surfaces of the first bone segment 1040 and the second bone segment 1042. In alternative embodiments, the implant 1060 may have a mesh and/or lattice structure that facilitates such boney in-growth, which structure may be formed via additive manufacturing.

As mentioned previously, a medializing calcaneal osteotomy may optionally be performed in addition to or in place of the Evans calcaneal osteotomy. As shown, the heel 1050 may be cut from the remainder of the second bone segment 1042 and may be displaced medially. This displacement may also help to restore normal gait and tendon function in the foot 200, particularly when coupled with the Evans calcaneal osteotomy. The proper displacement of the heel 1050 relative to the remainder of the second bone segment 1042 may be determined based on analysis of the CAD models from scans of the foot 200. If desired, the model of the calcaneus 1000 may be divided and manipulated in CAD to simulate the repositioning of the heel 1050 pursuant to the medializing calcaneal osteotomy. Thus, the alignment of the heel 1050 relative to the remainder of the foot 200 can easily be assessed and optimized prior to surgery.

Such preoperative alignment and planning may be particularly useful where multiple procedures, such as the Evans calcaneal osteotomy and the medializing calcaneal osteotomy, are combined for a single patient. Without such planning, it may be difficult to properly assess the effect of the combined procedures on the patient's anatomy. For example, the effect of the Evans calcaneal osteotomy, and that of the medializing calcaneal osteotomy, is to shift the heel 1050 medially. The combined shift may be difficult to assess in the operating room but may be much more easily and accurately gauged via manipulation of the modeled anatomy.

In some embodiments, one or more additional procedures may be carried out, in addition to or in the alternative to those of FIG. 9. For example, in addition to or in the alternative to the Evans calcaneal osteotomy and the medializing calcaneal osteotomy, a cotton osteotomy (medial cuneiform opening wedge osteotomy) and/or a first metatarsal midfoot osteotomy may be performed. Patient-specific cutting guides may be designed, fabricated, and surgically used to facilitate any of these procedures through the presence of bone engagement surfaces that are shaped to rest on the particular bony surfaces adjacent to the osteotomy.

As in the case of the Evans calcaneal osteotomy, a custom cutting guide, or cutting guide 1053, may be generated to help the surgeon obtain the correction that was previously modeled and/or planned using the computer models of the foot 200. The cutting guide 1053 may have a structure and function similar to that of the cutting guide 1043 used for the Evans calcaneal osteotomy. Such a cutting guide may have contoured surfaces that match the contours of the adjoining boney surfaces of the remainder of the second bone segment 1042 and/or the heel 1050.

More specifically, the cutting guide 1053 may have a first end 1054 and a second end 1055, each of which has a bone attachment feature 1056. The bone attachment features 1056 may be used to secure the first end 1054 and the second end 1055 to the second bone segment 1042 and the heel 1050, respectively. The first end 1054 may have a first bone engagement surface 1057 that is shaped to match a corresponding contour on the second bone segment 1042, and the second end 1055 may have a second bone engagement surface 1058 that is shaped to match a corresponding contour on the heel 1050. Thus, the cutting guide 1053 may naturally lie flush with the surface of the calcaneus 1000, in the optimal position on the calcaneus 1000 to facilitate resection of the calcaneus 1000 to divide the second bone segment 1042 from the heel 1050. The cutting guide 1053 may have a guide feature 1059, such as a slot, that can be used to guide a cutter to form a single cut between the second bone segment 1042 and the heel 1050.

In order to maintain the heel 1050 in the proper position relative to the remainder of the second bone segment 1042, a bone plate 1070 may be secured to the heel 1050 and to the remainder of the second bone segment 1042. The bone plate 1070 may include a first end 1080 secured to the remainder of the second bone segment 1042, a second end 1082 secured to the heel 1050, and an intermediate portion 1084 that extends from the first end 1080 to the second end 1082, and provides the desired medial shift between the first end 1080 and the second end 1082. The first end 1080 and the second end 1082 may be secured to the remainder of the second bone segment 1042 and to the heel 1050, respectively, through the use of screws 1090.

Like the implant 1060, the bone plate 1070 may be made of any known biocompatible material, through the use of any manufacturing process known in the art. In some embodiments, the bone plate 1070 may also be fabricated specifically for the foot 200, enabling the bone plate 1070 to precisely maintain the desired level of correction. When made specifically for the foot 200 in combination with each other, the implant 1060 and the bone plate 1070 may provide a highly predictable, precise, and customizable level of correction of the flat foot deformity.

Figure 11:
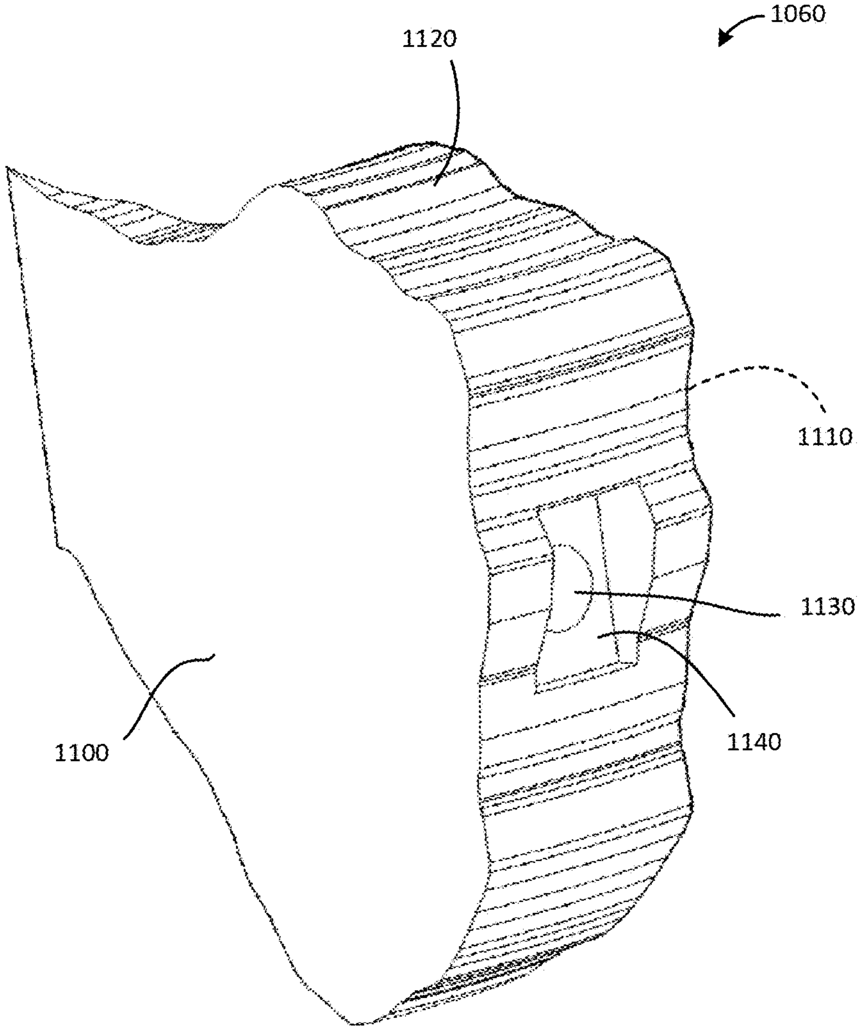
FIG. 11 is a perspective view of the implant of FIG. 10, in isolation, according to one embodiment.

FIG. 11 is a perspective view of the implant 1060, in isolation. As shown, the implant 1060 may have a first bone-facing surface 1100 that is generally flat and shaped to match the cut surface of the first bone segment 1040. The first bone-facing surface 1100 is shown in FIG. 11 with a smooth shape; however, in alternative embodiments, the first bone-facing surface 1100 may be roughened and/or may have teeth, spikes, ridges, and/or other features intended to penetrate the first bone segment 1040 in order to provide for more secure engagement of the implant 1060 with the first bone segment 1040. Similarly, the implant 1060 may have a second bone-facing surface 1110 (not visible) that is also generally flat and shaped to match the cut surface of the second bone segment 1042. Like the first bone-facing surface 1100, the second bone-facing surface 1110 may be roughened or have protruding features that strengthen engagement of the implant 1060 with the second bone segment 1042. If desired, the implant 1060 may be further held in place through the use of bone screws, cement, one or more bone plates, and/or other features known in the art to secure an implant to bone.

The edges of the first bone-facing surface 1100 and the second bone-facing surface 1110 may be shaped to line up with the edges of the cut surfaces of the first bone segment 1040 and the second bone segment 1042, respectively. The implant 1060 may also have a contoured surface 1120 that extends between the edges of the first bone-facing surface 1100 and the second bone-facing surface 1110. The contoured surface 1120 may also be contoured to match the contours of the adjoining portions of the first bone segment 1040 and the second bone segment 1042. Thus, the contoured surface 1120 may provide a continuous surface, devoid of protrusions, that extends between the adjoining surfaces of the first bone segment 1040 and the second bone segment 1042.

A threaded hole 1130 may optionally be provided in the contoured surface 1120. The threaded hole 1130 may be used to secure the implant 1060 to an insertion instrument, a positioning instrument, and/or a removal instrument. The threaded hole 1130 may be formed in a recess 1140 in the contoured surface 1120 so that the threaded hole 1130 can have the desired orientation, without affecting the shape of the contoured surface 1120 more than necessary. Of course, many other features may be used to secure an instrument to the implant 1060, including various clips, clamps, fasteners, and interfacing features, as known in the art.

The present disclosure is not limited to cutting guides or extremity procedures. In some embodiments, patient-specific instrumentation may be used to correct a wide variety of bone conditions. Such conditions include, but are not limited to, any angular deformities from within one bone segment in either the lower or upper extremities (for example, tibial deformities, calcaneal deformities, femoral deformities, and radial deformities). The present disclosure may also be used to treat an interface between two bone segments (for example, the ankle joint, metatarsal cuneiform joint, lisfranc's joint, complex charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cubiod or subtalar joint or at the ankle between the tibia and talar junction. Additionally, patient-specific instruments could be used in the proximal leg between two bone segments or in the upper extremity such as found at the wrist or metacarpal levels.

FIGS. 12A, 12B, 12C, 12D, 12E, 12F, 12G, and 12H are top perspective, top, bottom, front elevation, rear elevation, right, left, and alternative top perspective, respectively, of a patient-specific cutting guide, or cutting guide 1200, according to one alternative embodiment.

The cutting guide 1200 may be designed to facilitate resection of a first cuneiform and a first metatarsal with planar cuts at the proper angles to provide dual-plane correction of the orientation of the first metatarsal, thereby providing correction in a lateral direction and in a plantar direction or a dorsal direction.

As shown, the cutting guide 1200 may have a body 1210 with a monolithic construction and the general shape of a rectangular prism. The body 1210 may reside on the dorsal surfaces of the first cuneiform and the first metatarsal to provide proper alignment of the body 1210 with the metatarsocuneiform joint.

Further, the body 1210 may have one or more bone attachment features that facilitate attachment of the body 1210 to the first cuneiform and/or the first metatarsal. Such bone attachment features may comprise any of a wide variety of holes, spikes, fastening devices, and/or the like. As embodied in FIGS. 12A through 12H, the bone attachment features may take the form of holes 1240 that extend from a bone facing side 1230 to the outward-facing side 1232 and/or one or more fixation devices. The holes 1240 may be shaped to accommodate pins, K-wires, and/or other elongated bone fixation elements that can be anchored in the first cuneiform and/or the first metatarsal to keep the cutting guide 1200 in place.

The bone facing side 1230 may be custom contoured to match the shapes of the first cuneiform and/or the first metatarsal. As embodied in FIGS. 12A through 12F, the bone facing side 1230 may have a cuneiform apposition portion 1242 shaped to lie against the surface of the first cuneiform, and a metatarsal apposition portion 1244 shaped to lie against the surface of the first metatarsal. As shown, the cuneiform apposition portion 1242 may be contoured to match the contour of the surface of the first cuneiform on which it is to rest, and the metatarsal apposition portion 1244 may similarly be contoured to match the contour of the surface of the first metatarsal on which it is to rest. Thus, the body 1210 may have only one stable position and orientation relative to the first cuneiform and the first metatarsal.

The body 1210 may further have guide features that guide a cutter to resect the first cuneiform and the first metatarsal in the manner needed to make the desired correction. For example, the guide features may be used to guide a planar cutting blade, an arcuate cutting blade, a drill or mill, a burr, and/or the like.

In the embodiment of FIGS. 12A through 12F, the guide features may guide a reciprocating planar blade, such as that of a surgical bone saw, that forms planar cuts in the first cuneiform and the first metatarsal. Thus, the guide features may take the form of a first slot 1250 and a second slot 1252, which may be positioned toward the center of the body 1210. Thus, upon proper positioning of the cutting guide 1200, the first slot 1250 may be positioned over the first cuneiform to facilitate resection of the first cuneiform, while the second slot 1252 may be positioned over the first metatarsal to facilitate resection of the first metatarsal.

In alternative embodiments, a guide feature may be designed to guide a different type of cutter, such as a drill, mill, or side-cutting burr. In such embodiments, the guide feature may not be a slot, but may instead be a translatable or rotatable cutter retainer that guides translation and/or rotation of the cutter relative to the bone.

Returning to FIGS. 12A through 12H, the body 1210 may further have features that facilitate desired translation and orientation of the first metatarsal in order to fuse or join the first cuneiform and the first metatarsal to complete the procedure. For example, in the illustrated embodiment, the cutting guide 1200 may include two alignment features 1260*a* and 1260*b*.

Figure 12A:
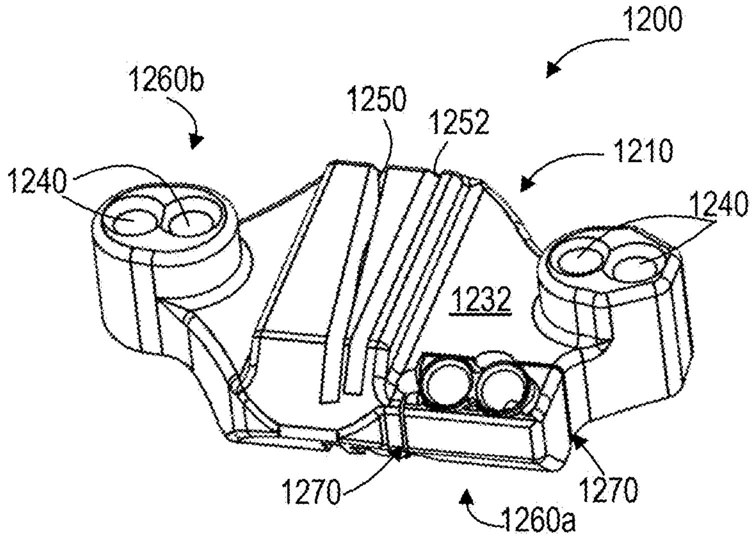
FIGS. 12A, 12B, 12C, 12D, 12E, 12F, 12G, and 12H are top perspective, top, bottom, front elevation, rear elevation, right, left, and alternative top perspective, respectively, of a patient-specific cutting guide according to one alternative embodiment.
Figure 12B:
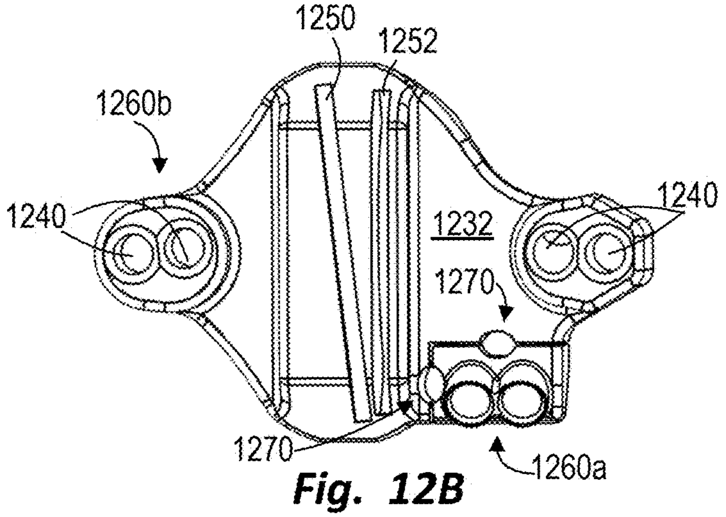
Figure 12C:
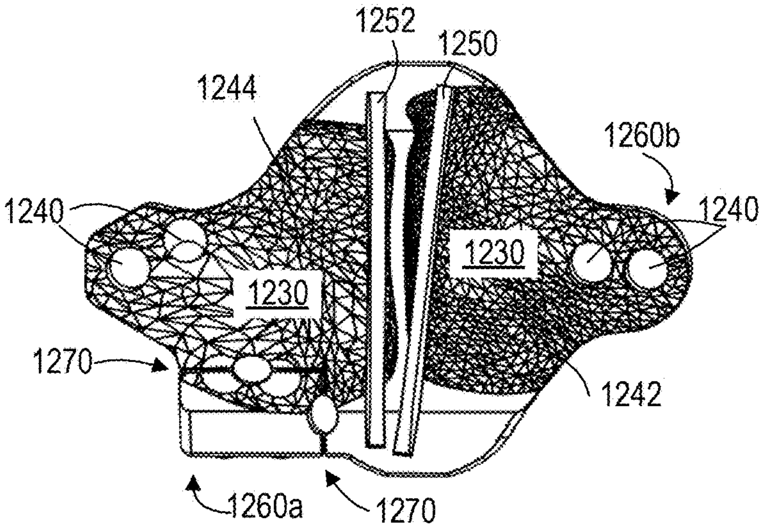
Figure 12D:
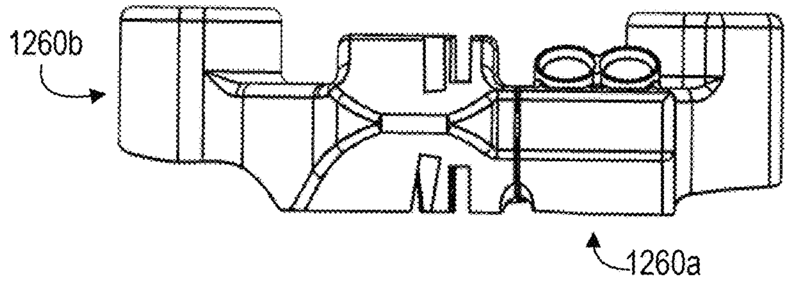
Figure 12E:
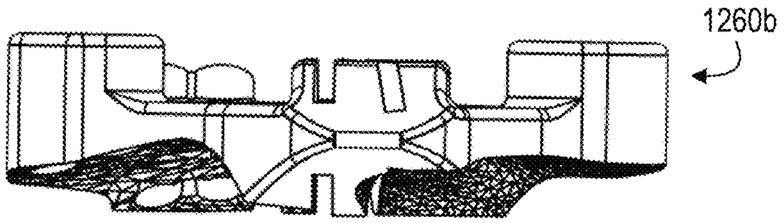
Figure 12F:
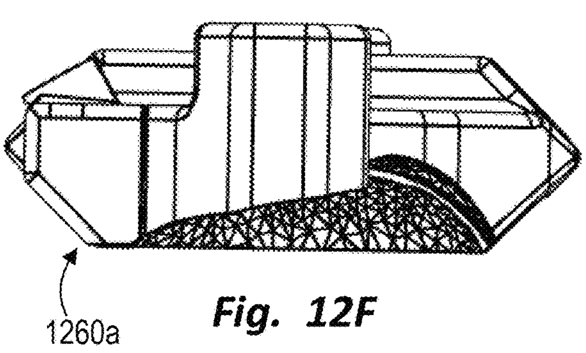
Figure 12G:
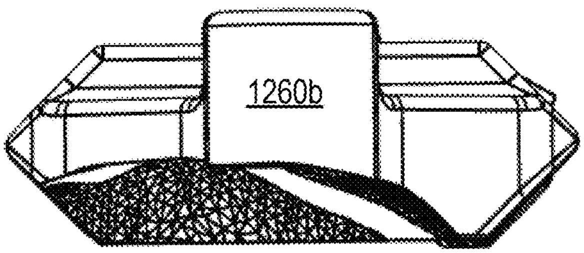

In the embodiment of FIG. 12A, one alignment feature 1260*a* is in the lower right-hand side of the body 1210, the distal side of the body, and the other alignment feature 1260*b* is on a proximal side of the body 1210. The two alignment features 1260*a* and 1260*b* may be separate features, or certain features such as one or more attachment features may serve a dual purpose as both an attachment feature and as an alignment feature. For example, in the embodiment of FIG. 12A, alignment feature 1260*b* may use the same structure as the bone attachment features and may take the form of holes 1240 that extend from a bone facing side 1230 to the outward-facing side 1232 and/or one or more fixation devices.

Figure 12H:
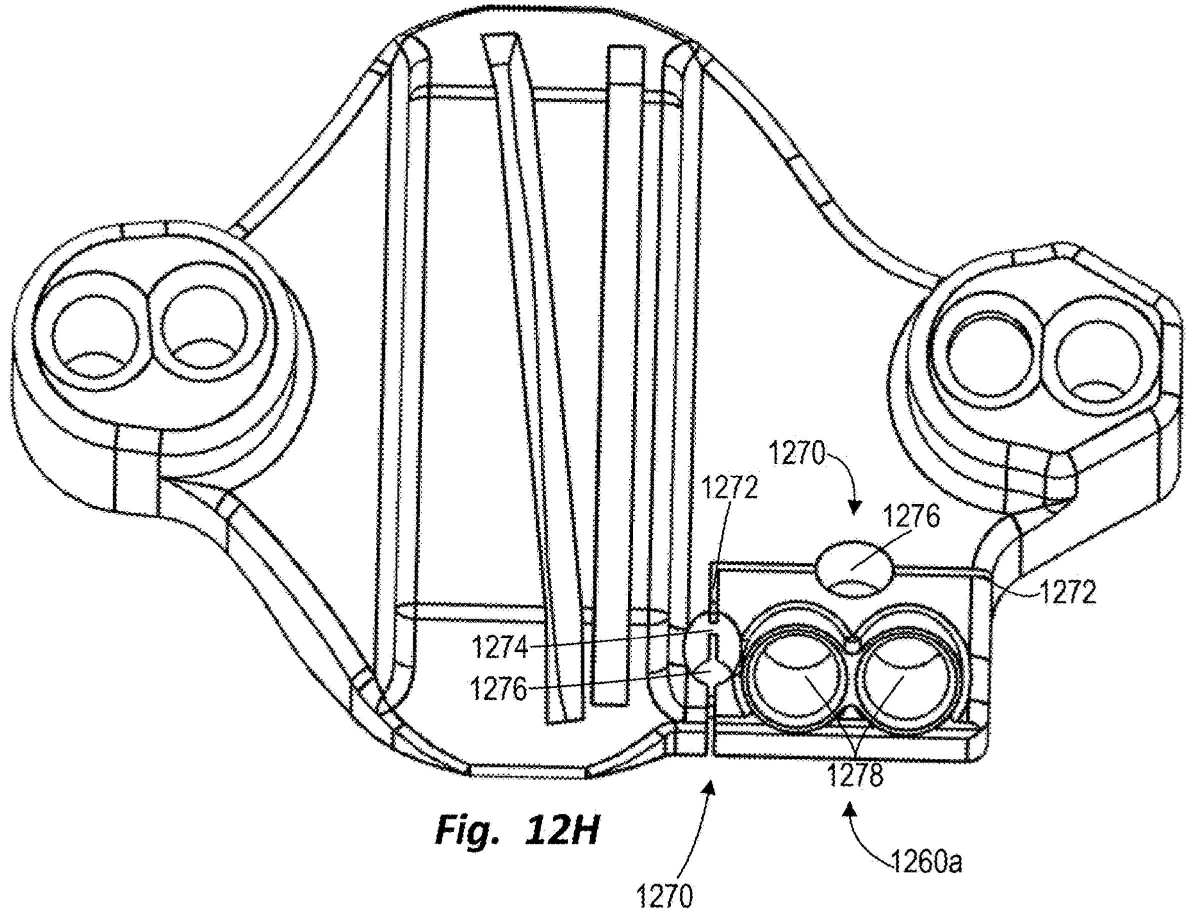

Referring to FIG. 12H, in certain embodiments, the cutting guide 1200 may include a detachable connector 1270 that couples an alignment feature 1260*a*, 1260*b* to the body 1210. The detachable connector 1270 may connect or couple the alignment feature 1260*a* to the body 1210 and/or the alignment feature 1260*b* to the body 1210. In one embodiment, the detachable connector 1270 may comprise a breakaway structure designed, engineered, and fabricated to securely connect an alignment feature 1260*a*, 1260*b* to the body 1210 for one part of a procedure and to readily separate or breakaway from the body 1210 when a breaker tool 1271 (See FIG. 14) is used to activate the breakaway function or feature.

In one embodiment, the detachable connector 1270 may include one or more grooves 1272 between an alignment feature 1260*a* and the body 1210. The groove 1272 is an opening between the alignment feature 1260 and the body 1210. Within a groove 1272 one or more bridges 1274 connect the alignment feature 1260 with the body 1210. In one embodiment, the size, position, number, and configuration of one or more grooves 1272 and the corresponding one or more bridges 1274 is determined such that the alignment feature 1260 remains securely connected to the body 1210 for one part of the procedure and can be readily separated using a breaker tool 1271 for another part of the procedure.

In certain embodiments, the detachable connector 1270 may include one or more receivers 1276. The receiver 1276 is sized, configured, and positioned to accept an end of the breaker tool 1271 such that insertion of the end of the breaker tool 1271 breaks one or more bridges 1274 and thus separates the alignment feature 1260 from the body 1210. The receiver 1276 may have any cross-section shape including circular, elliptical, square, rectangular, or the like.

In one embodiment, the alignment feature 1260, such as alignment feature 1260*a*, can include one or more bone attachment features that may take the form of holes 1278 that extend from a bone facing side 1230 to the outward-facing side 1232 and/or one or more fixation devices. In certain embodiments, a pair of parallel holes 1278 form a guide for pins 1280 (See FIG. 13) as part of a bone attachment feature. Advantageously, the holes 1278 may be angled with respect to a bone such as the first metatarsal. The angle for the holes 1278 may be customized based on the patient and the amount of adjustment desired for the first metatarsal.

Figure 13:
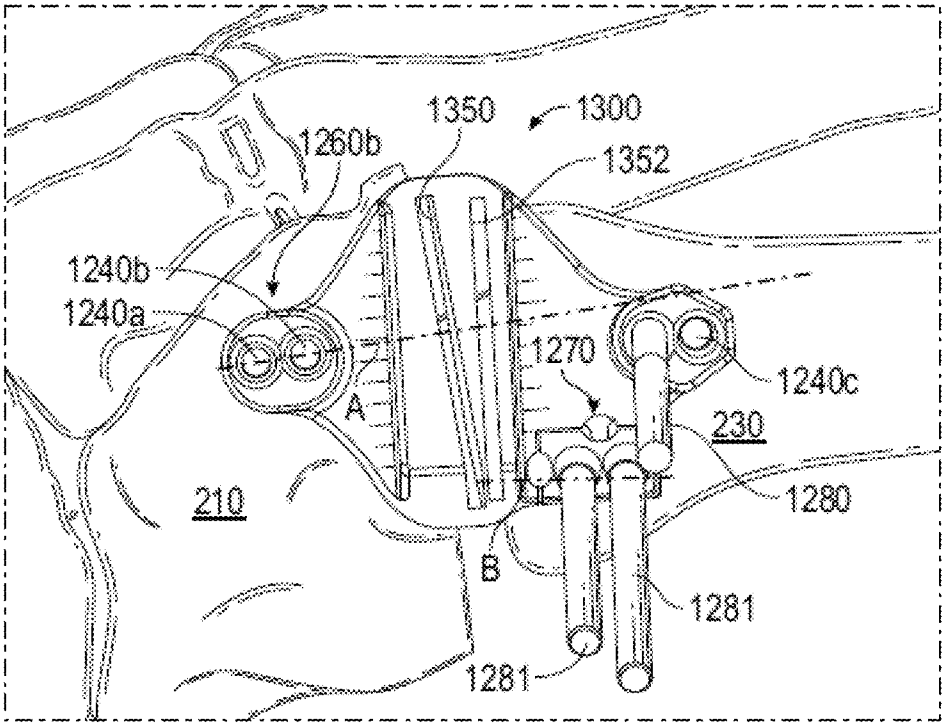
FIG. 13 illustrates a perspective view of a first cuneiform and first metatarsal with one embodiment of a cutting guide secured to the two bones.

FIG. 13 illustrates a perspective view of a first cuneiform 210 and first metatarsal 230 with one embodiment of a cutting guide 1300 secured to the two bones. The cutting guide 1300 includes pins 1280 in the holes 1240 to secure the cutting guide 1300 to the bones. (Pins 1280 for hole 1240*a* and hole 1240*b* and hole 1240*c* are omitted to facilitate certain disclosure.)

FIG. 13 illustrates that in one embodiment, the holes 1240 of each bone attachment feature can be parallel to each other such that pins 1280 in the holes 1240 are parallel to each other. Red line A illustrates that the holes 1240*a*, 1240*b* are aligned perpendicular to a resection cut that has been made on the first cuneiform 210 through slot 1350. Pins 1280 in holes 1240*a,b* may be referred to as cuneiform pins and these parallel cuneiform pins form a line (red line A) perpendicular to a cut plane in the first cuneiform 210. Red line B illustrates that the holes and corresponding parallel pins 1281 (which may be referred to as metatarsal pins) may form a line perpendicular to a cut plane in the first metatarsal 230. The metatarsal pins 1281 are aligned perpendicular to a resection cut (also referred to as a MET cut) that has been made on the first metatarsal 230 through slot 1352.

Figure 14:
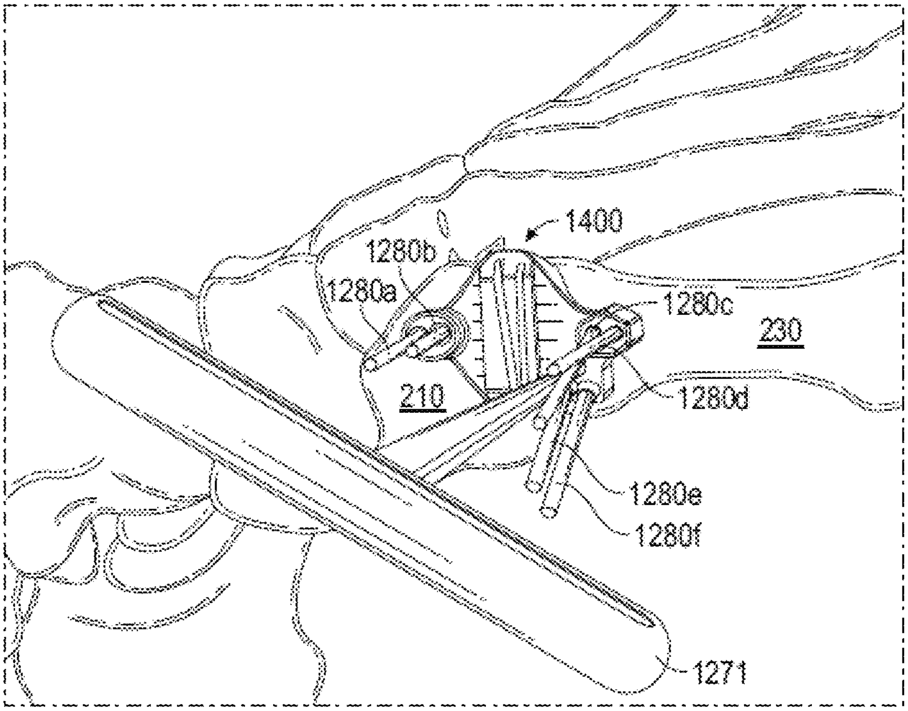
FIG. 14 illustrates a perspective view of a first cuneiform and first metatarsal with one embodiment of a cutting guide secured to the two bones.

FIG. 14 illustrates a perspective view of a first cuneiform 210 and first metatarsal 230 with one embodiment of a cutting guide 1400 secured to the two bones. The cutting guide 1400 includes pins 1280*a-f* in the holes 1240 of bone attachment features and the holes 1278 of the alignment features 1260, such as alignment feature 1260*a*.

At this stage in a surgical procedure, the cutting guide 1400 is placed on the first cuneiform 210 and the first metatarsal 230 and pins 1280*a-d* are connected to the bones through the respective holes 1240. Next, a surgeon uses the guide features of the cutting guide 1400 to reset the first cuneiform 210 and the first metatarsal 230. Then, a surgeon may insert pins 1280*e,f* into holes 1278 of the alignment feature 1260*a*. Alternatively, in another embodiment, a surgeon may insert pins 1280*e,f* into holes 1278 of the alignment feature 1260*a* before resecting the first cuneiform 210 and/or first metatarsal 230.

In one embodiment, a surgeon may next remove the pins 1280*c,d*. Alternatively, a surgeon may remove the pins 1280*c,d* after breaking the alignment feature 1260*a* away from the body 1210, as described below.

Advantageously, with pins 1280*a,b* in place and pins 1280*e,f* in place the cutting guide 1400 has been fabricated and custom engineered such that bringing pins 1280*a,b* and pins 1280*e,f* in parallel alignment with each other will align the resected surfaces of the first cuneiform 210 and first metatarsal 230 to accomplish a desired translation, rotation, and/or orientation of the first metatarsal 230 relative to the first cuneiform 210 for the procedure. In other words, the alignment features 1260*a,b* are placed and configured in the cutting guide 1400 such that bringing pins 1280*a,b* and pins 1280*e,f* in parallel alignment provides a desired frontal plane correction required to bring sesamoids into proper alignment, based on an evaluation of a pre-operative CAD model. Because the cutting guide 1400 is custom fabricated for a particular patient, the alignment features 1260*a,b* are positioned such that aligning these alignment features 1260*a* after the resection will provide a desired frontal plane rotation that is unique to each patient and built into, designed into, the cutting guide 1400. The detachable connector 1270 connecting the alignment feature 1260*a* to the body 1210 is what enables a single cutting guide 1200 to become two during a procedure and provide a custom translation and rotation of a first metatarsal 230 that can be unique for each patient.

Furthermore, fabricating a cutting guide that is customized to a particular patient and a specific desired correction/adjustment enables correction of a variety of angular deformities (in all 3 planes) of the midfoot or hind foot and ankle where an osteotomy could be used. The alignment features 1260 disclosed in this solution and the corresponding pins formed within a cutting guide that may also include a detachable connector 1270 enable correction procedures for a variety of angular deformities (in all 3 planes) of the midfoot or hind foot and ankle where an osteotomy could be used. For example, embodiments of the procedures and devices herein disclosed can be used to address cavus, and mid foot dislocations, fracture malunion, metatarsal adductus, etc. They can also be used in preparation for joint resurfacing procedures of the foot and ankle to optimize placement of an arthroplasty implant.

Next, a breaker tool 1271 can be used to separate the alignment feature 1260*a* from the body 1210. In one embodiment, a breaker tool 1271 can be a "T" shaped tool with a crosswise proximal handle, a shaft, and a distal end. A user may operate the breaker tool 1271 by placing the distal end in a receiver 1276 of one or more detachable connectors 1270. Pressing and/or twisting the distal end into the receiver 1276 breaks one or more bridges 1274 and thus separates the alignment feature 1260*a*. A user may insert the distal end into one or more receivers 1276 to separate the alignment feature 1260*a* from the body 1210.

Next, with the alignment feature 1260*a* separated from the body 1210, and pins 1280*c,d* removed, a user can remove the two parts of the cutting guide 1400 separately. Pins 1280*a,b* remain in the first cuneiform 210 and pins 1280*e,f* remain in the first metatarsal 230.

Figure 15:
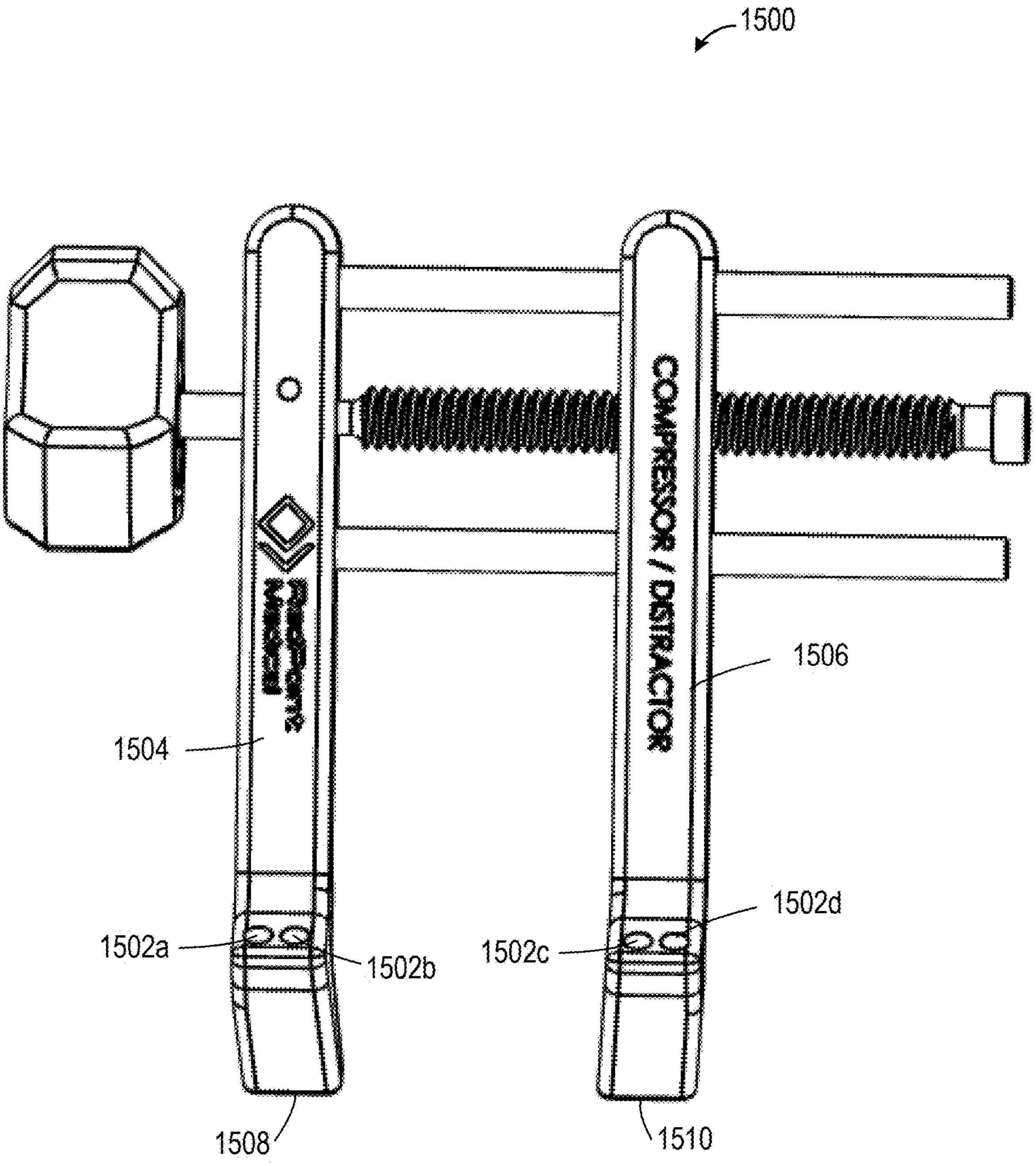
FIG. 15 illustrates an exemplary embodiment of a parallel distractor that can be used with certain embodiments.

Next, a parallel compressor/distractor 1500 such as the exemplary parallel compressor/distractor 1500 illustrated in FIG. 15 is used to distract the first metatarsal 230 relative to the first cuneiform 210. The user slides holes 1502*a,b* over pins 1280*a,b* and holes 1502*c,d* over pins 1280*e,f*. This causes a desired rotation and translation of the first metatarsal 230 relative to the first cuneiform 210. When a user places the parallel compressor/distractor 1500 on over these pins 1280*a,b,e,f* this forces the cut faces of the two bones to become parallel. Advantageously, the cut faces of the two bones can be forced to become parallel because the position, orientation, and angles of the holes 1278 and/or holes of either or both of the alignment feature 1260*a* and alignment feature 1260*b* can be predefined and customized for each patient when the cutting guide 1300 is fabricated. This alignment enables parallel compression of the two bones together using the parallel compressor/distractor 1500. Parallel compression enables more effective compression of the two bones together. Next, the space between the resected surfaces of the first cuneiform 210 and the first metatarsal 230 is prepared for fusion. Then, the parallel compressor/distractor 1500 is activated such that the first cuneiform 210 and the first metatarsal 230 are fused together. The parallel compressor/distractor 1500 may include a first leg 1504 and a second leg 1506. At one end of each leg 1504/1506, the leg may include a toe 1508/1510 at its distal end. In one embodiment, the toes 1508/1510 are angled to point towards each other. The angled configuration of the legs 1504/1506 by way of the toes 1508/1510 may apply a torque force at the toes 1508/1510 which may further assist in pressing two bones connected to the parallel compressor/distractor 1500 together.

Figure 16:
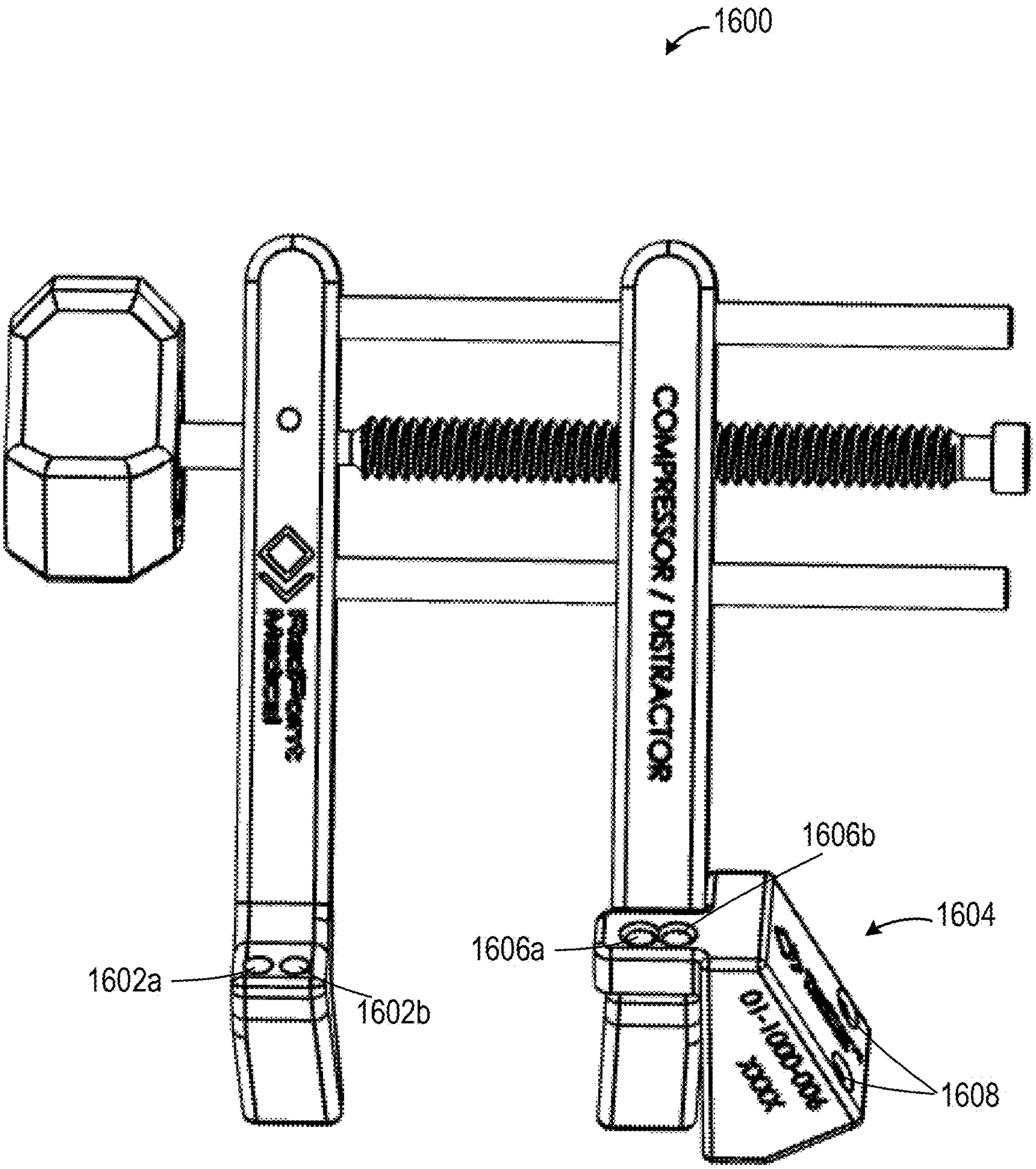
FIG. 16 illustrates an exemplary embodiment of a parallel distractor that can be used with certain embodiments.

Referring to FIG. 16, in certain embodiments, a parallel compressor/distractor 1600 such as the exemplary parallel compressor/distractor 1600 having holes 1602 illustrated in FIG. 16 can be used to distract the first metatarsal 230 relative to the first cuneiform 210. The parallel compressor/distractor 1600 may also include a cross joint guide 1604. The user may slide holes 1602*a,b* over pins 1280*a,b* and holes 1602*c,d* (not visible, obscured by holes 1606*a,b* which are aligned with holes 1602*c,d*) over pins 1280*e,f*.

The cross joint guide 1604 may serve as a guide for cross joint fasteners or other kinds of implants or fixation devices that can be installed across a joint between the first cuneiform 210 and the first metatarsal 230. In one embodiment, the cross joint guide 1604 may include one or more bone attachment features that may take the form of holes 1608 that extend from one side of the cross joint guide 1604 to the other side and/or one or more fixation devices. The holes 1608 may be used to connect a holding across the joint between the first cuneiform 210 and the first metatarsal 230 after compression.

Figure 17:
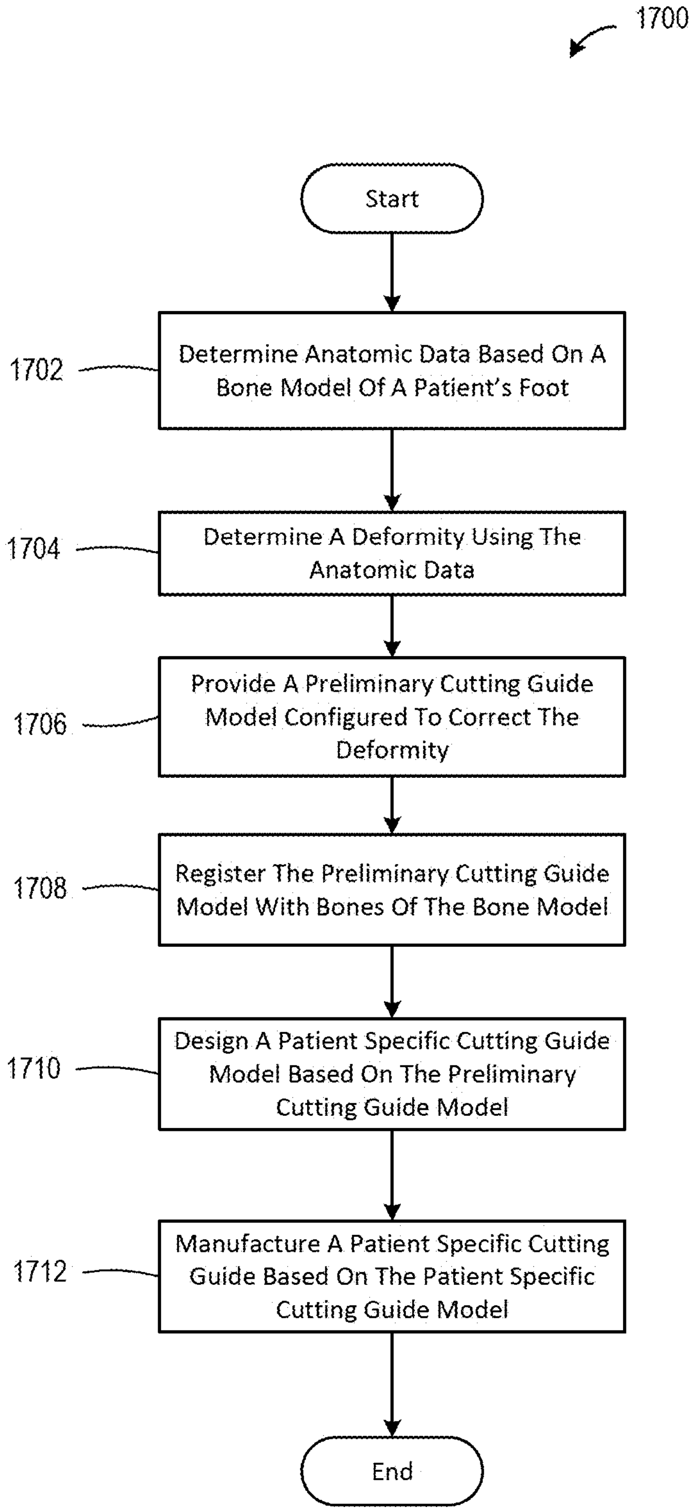
FIG. 17 is a flowchart diagram depicting a method for generating one or more patient specific instruments configured to correct a bone condition, according to one embodiment.

FIG. 17 illustrates a flowchart diagram depicting a method 1700 for generating one or more patient specific instruments configured to correct a bone condition, according to one embodiment. Prior to steps of the method 1700, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve or be a part of anatomic data for a patient.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A bone model or anatomic model of a patient's body or body part(s) may be generated by computing devices that analyze medical imaging images. Structures of a patient's body can be determined using a process called segmentation.

As used herein, "segmentation" or "image segmentation" refers the process of partitioning an image into different meaningful segments. These segments may correspond to different tissue classes, organs, pathologies, bones, or other biologically relevant structures. Medical image segmentation accommodates imaging ambiguities such as by low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while non-parametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

In one embodiment, the method 1700 begins after a bone model of a patient's body or body part(s) is generated. In a first step 1702, the method 1700 may review the bone model and data associated with the bone model to determine anatomic data of a patient's foot.

After step 1702, the method 1700 determine 1704 a deformity in the patient's anatomy using the anatomic data. In certain embodiments, the detection and/or identification of a deformity may employ advanced computer analysis, expert systems, machine learning, and/or automated/artificial intelligence. As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.) Various kinds of deformities may be identified, such as a bunion. The deformities determined may include congenital as well as those caused by injury or trauma.

Next, the method 1700 proceeds and a preliminary cutting guide model is provided 1706 from a repository of template cutting guide models. A preliminary cutting guide model is a model of a preliminary cutting guide.

As used herein, "preliminary cutting guide" refers to a guide configured, designed, and/or engineered to serve as a template, prototype, archetype, or starting point for creating, generating, or fabricating a patient specific cutting guide. In one aspect, the preliminary cutting guide may be used, as-is, without any further changes, modifications, or adjustments and thus become a patient specific cutting guide. In another aspect, the preliminary cutting guide may be modified, adjusted, or configured to more specifically address the goals, objectives, or needs of a patient or a surgeon and by way of the modifications become a patient specific cutting guide. The patient specific cutting guide can be used by a user, such as a surgeon, to guide making one or more resections of a structure, such as a bone for a procedure. Accordingly, a preliminary cutting guide model can be used to generate a patient specific cutting guide model. The patient specific cutting guide model may be used in a surgical procedure to address, correct, or mitigate effects of the identified deformity and may be used to generate a patient specific cutting guide that can be used in a surgical procedure for the patient.

In certain embodiments, the preliminary cutting guide model may be generated based on anatomic data and/or a bone model or a combination of these, and no model or predesigned structure, template, or prototype. Alternatively, or in addition, the preliminary cutting guide model may be, or may originate from, a template cutting guide model selected from a set of template cutting guide model. Each model in the set of template cutting guide models may include one or more cutting guide features positioned and/or sized and/or configured to fit for an average patient's foot. The template cutting guide model may subsequently be modified or revised by an automated process or manual process to generate the preliminary cutting guide model used in this disclosure.

As used herein, "template cutting guide" refers to a guide configured, designed, and/or engineered to serve as a template for creating, generating, or fabricating a patient specific cutting guide. In one aspect, the template cutting guide may be used, as-is, without any further changes, modifications, or adjustments and thus become a patient specific cutting guide. In another aspect, the template cutting guide may be modified, adjusted, or configured to more specifically address the goals, objectives, or needs of a patient or a surgeon and by way of the modifications become a patient specific cutting guide. The patient specific cutting guide can be used by a user, such as a surgeon, to guide making one or more resections of a structure, such as a bone for a procedure. Accordingly, a template cutting guide model can be used to generate a patient specific cutting guide model. The patient specific cutting guide model may be used in a surgical procedure to address, correct, or mitigate effects of the identified deformity and may be used to generate a patient specific cutting guide that can be used in a surgical procedure for the patient.

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

Next, the method 1700 may register 1708 the preliminary cutting guide model with one or more bones of the bone model. This step 1708 facilitates customization and modification of the preliminary cutting guide model to generate a patient specific cutting guide model from which a patient specific cutting guide can be generated. The registration step 1708 combines two models and/or patient imaging data and positions both models for use in one system and/or in one model.

As used herein, "registration" or "image registration" refers to a method, process, module, component, apparatus, and/or system that seeks to achieve precision in the alignment of two images. As used here, "image" may refer to either or both an image of a structure or object and another image or a model (e.g., a computer based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

Next, the method 1700 may design 1710 a patient specific cutting guide model based on the preliminary cutting guide model. The design step 1710 may be completely automated or may optionally permit a user to make changes to a preliminary cutting guide model or partially completed patient specific cutting guide model before the patient specific cutting guide model is complete. A preliminary cutting guide model and patient specific cutting guide model are two examples of an instrument model. As used herein, "instrument model" refers to a model, either physical or digital, that represents an instrument, tool, apparatus, or device. Examples, of an instrument model can include a cutting guide model, a patient specific cutting guide model, and the like. In one embodiment, a patient specific cutting guide and a patient specific cutting guide model may be unique to a particular patient and that patient's anatomy and/or condition.

The method 1700 may conclude by a step 1712 in which patient specific cutting guide may be manufactured based on the patient specific cutting guide model. Various manufacturing tools, devices, systems, and/or techniques can be used to manufacture the patient specific cutting guide. As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

Figure 18:
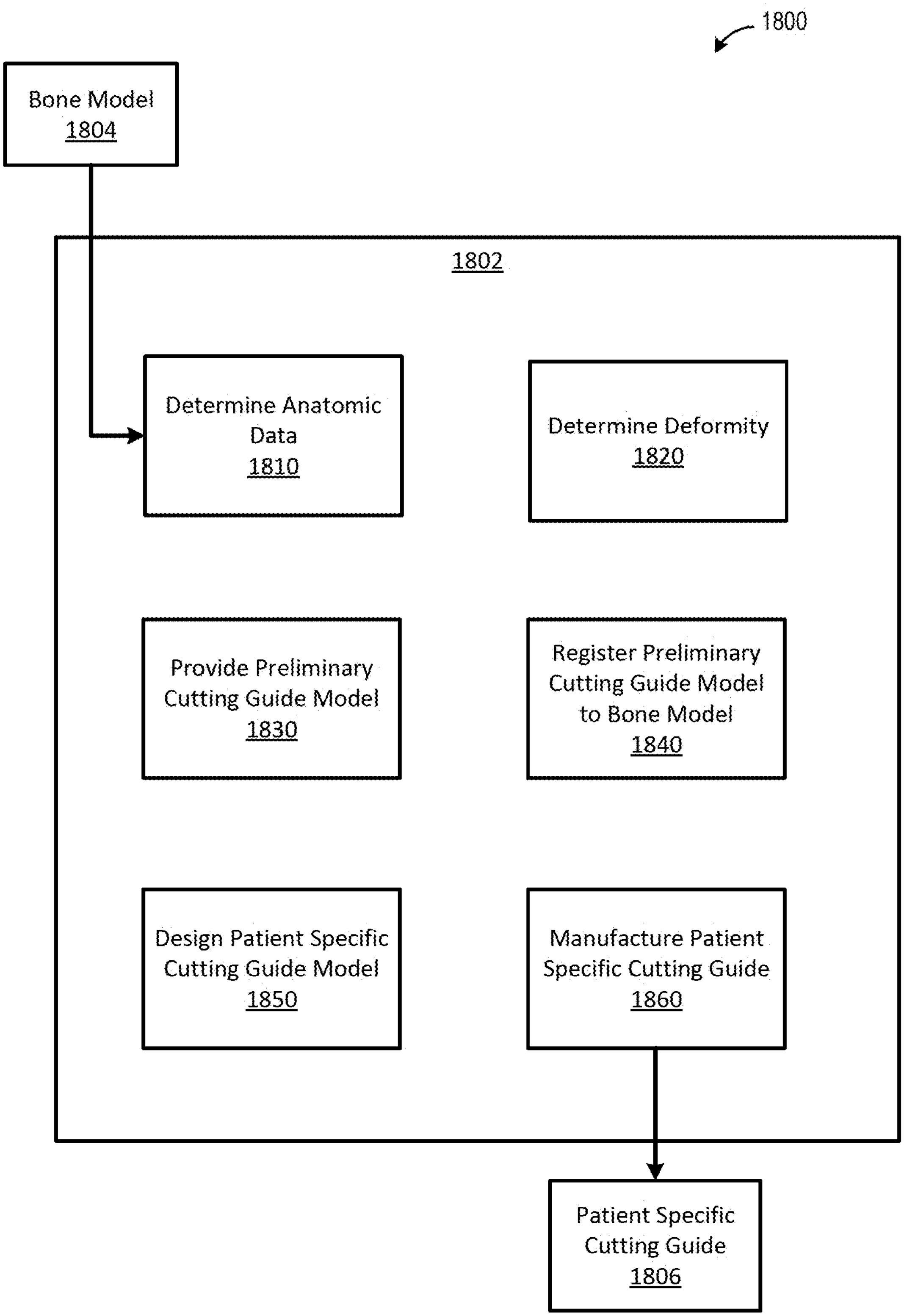
FIG. 18 illustrates an exemplary system configured to generate one or more patient specific instruments configured to correct a bone condition, according to one embodiment.

FIG. 18 illustrates an exemplary system 1800 configured to generate one or more patient specific instruments configured to correct a bone condition, according to one embodiment. "Bone condition" refers to any of a variety of conditions of bones of a patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). "Malrotation" refers to a condition in which a part, typically a part of a patient's body has rotated from a normal position to an unnormal or uncommon position. The system 1800 may include an apparatus 1802 configured to accept, review, receive or reference a bone model 1804 and provide a patient specific cutting guide 1806. In one embodiment, the apparatus 1802 is a computing device. In another embodiment, the apparatus 1802 may be a combination of computing devices and/or software components or a single software component such as a software application.

The apparatus 1802 may include a determination module 1810, a deformity module 1820, a provision module 1830, a registration module 1840, a design module 1850, and a manufacturing module 1860. Each of which may be implemented in one or more of software, hardware, or a combination of hardware and software.

The determination module 1810 determines anatomic data 1812 from a bone model 1804. In certain embodiments, the system 1800 may not include a determination module 1810 if the anatomic data is available directly from the bone model 1804. In certain embodiments, the anatomic data for a bone model 1804 may include data that identifies each anatomic structure within the bone model 1804 and attributes about the anatomic structure. For example, the anatomic data may include measurements of the length, width, height, and density of each bone in the bone model. Furthermore, the anatomic data may include position information that identifies where each structure, such as a bone is in the bone model 1804 relative to other structures, including bones. The anatomic data may be in any suitable format and may be stored separately or together with data that defines the bone model 1804.

In one embodiment, the determination module 1810 may use advanced computer analysis such as image segmentation to determine the anatomic data. Alternatively, or in addition the determination module 1810 may use software and/or systems that implement one or more artificial intelligence methods (e.g., machine learning and/or neural networks) for deriving, determining, or extrapolating, anatomic data from the bone model. In one embodiment, the determination module 1810 may perform an anatomic mapping of the bone model 1804 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

The deformity module 1820 determines or identifies one or more deformities or other anomalies based on the anatomic data 1812. The deformity may include a deformity between two bones of a patient's foot as represented in the bone model 1804. In one embodiment, the deformity module 1820 may compare the anatomic data 1812 to a general model that is representative of most patient's anatomies and that does not have a deformity or anomaly. In one embodiment, if the anatomic data 1812 does not match the general model a deformity is determined. Various deformities may be detected including those that have well-known names for the condition and those that are unnamed.

The provision module 1830 is configured to provide a preliminary cutting guide model 1838. The provision module 1830 may use a variety of methods to provide the preliminary cutting guide model. In one embodiment, the provision module 1830 may generate preliminary cutting guide model. In the same or an alternative embodiment, the provision module 1830 may select a template cutting guide model for an osteotomy procedure configured to correct the deformity identified by the deformity module 1820. In one embodiment, the provision module 1830 may select a template cutting guide model from a set of template cutting guide models (e.g., a library, set, or repository of template cutting guide models).

The registration module 1840 registers the preliminary cutting guide model with one or more bones or other anatomical structures of the bone model 1804. As explained above, registration is a process of combining medical imaging data, patient imaging data, and/or one or more models such that the preliminary cutting guide model can be used with the bone model 1804.

The design module 1850 designs a patient specific cutting guide (or patient specific cutting guide model) based on the preliminary cutting guide model. The design operation of the design module 1850 may be completely automated, partially automated, or completely manual. A user may control how automated or manual the designing of the patient specific cutting guide (or patient specific cutting guide model) is.

The manufacturing module 1860 may manufacture a patient specific cutting guide 1806 using the preliminary cutting guide model. The manufacturing module 1860 may use a patient specific cutting guide model generated from the preliminary cutting guide model. The manufacturing module 1860 may provide the patient specific cutting guide model to one or more manufacturing tools and/or fabrication tool. The patient specific cutting guide model may be sent to the tools in any format such as an STL file or any other CAD modeling or CAM file or method for data exchange. In one embodiment, a user can adjust default parameters for the patient specific cutting guide such as types and/or thicknesses of materials, dimensions, and the like before the manufacturing module 1860 provides the patient specific cutting guide model to a manufacturing tool.

FIGS. 19A-19H are top perspective, top perspective, bottom, front elevation, rear elevation, right, left, and alternative top perspective, respectively, of a patient-specific cutting guide, or cutting guide 1900, according to one alternative embodiment.

The cutting guide 1900 may be designed to facilitate resection of a first cuneiform near a distal end and a first metatarsal near a proximal end with planar cuts at the proper angles to provide dual-plane correction of the orientation of the first metatarsal relative to the first cuneiform, thereby providing correction in a lateral direction, in a plantar direction, and/or a dorsal direction.

As shown, the cutting guide 1900 may have a body 1910 with a monolithic construction and the general shape of a rectangular prism. As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

The body 1910 includes a proximal side 1912, a distal side 1914, a medial side 1916, a lateral side 1918, a superior side 1920, and an inferior side 1922. In the illustrated embodiment, the body 1910 may also include a proximal arm 1930 that extends from the body 1910 and a distal arm 1940 that extends from the body 1910. The proximal side 1912 is the side closest to the core of the patient when the cutting guide 1900 is in use. The distal side 1914 is the side furthest from the core of the patient when the cutting guide 1900 is in use. The medial side 1916 is the side facing medially when the cutting guide 1900 is in use. The lateral side 1918 is the side facing laterally when the cutting guide 1900 is in use. The superior side 1920 is the side facing up away from the bone(s) when the cutting guide 1900 is in use. The inferior side 1922 is the side facing down, facing, and/or contacting the bone(s) (e.g., contacting a surface of one or more bones) when the cutting guide 1900 is in use.

The inferior side 1922 may be custom contoured to match the shapes of one or more of the surfaces of the first cuneiform and/or the first metatarsal. In one embodiment, the inferior side 1922 may include a bone engagement surface 1924. The bone engagement surface 1924 can be shaped to match a first surface of a first bone and a second surface of a second bone of a joint.

As used herein, "bone engagement surface" refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, articulations of foot, and the like. (Search "joint" on Wikipedia.com Dec. 19, 2021. CC-BY-SA 3.0 Modified. Accessed Jan. 20, 2022.)

In one example, the bone engagement surface 1924 can be shaped such that the bone engagement surface 1924 matches a surface of a cuneiform bone and a surface of a metatarsal bone of a tarsometatarsal ("TMT") joint. The bone engagement surface 1924 can be so shaped because it is fabricated from a bone model of the patient's bones. The body 1910 is configured, designed, and/or fabricated to seat transverse to a joint (e.g., a TMT joint) with the bone engagement surface 1924 engaging a first surface of a first bone and a second surface of a second bone.

In one embodiment, the body 1910 is configured to reside on the dorsal surfaces of the first cuneiform and the first metatarsal to provide proper alignment of the body 1910 with the metatarsocuneiform joint (e.g., the joint between the first metatarsal and the medial cuneiform bone, aka a TMT joint). In another embodiment, the body 1910 is configured to reside or sit between the medial surfaces and the dorsal surfaces, or on the medial surfaces of the first cuneiform and the first metatarsal to provide proper alignment of the body 1910 with the metatarsocuneiform joint (e.g., the joint between the first metatarsal and the medial cuneiform bone) for an osteotomy.

In certain embodiments, the bone engagement surface 1924 may include a cuneiform apposition portion 1926 and a metatarsal apposition portion 1928. As shown, the cuneiform apposition portion 1926 may be contoured to match the contour of the surface of the first cuneiform on which it is to rest, and the metatarsal apposition portion 1928 may similarly be contoured to match the contour of the surface of the first metatarsal on which it is to rest. (See FIG. 19C) Thus, the body 1910 may have only one stable position and orientation relative to the first cuneiform and the first metatarsal during a surgical osteotomy for correcting the condition.

Advantageously, the fidelity of the patient imaging data enables the bone model, preliminary cutting guide model, and patient specific instrument (e.g., patient specific cutting guide, patient specific pin guide, patient specific alignment guide, etc.) to uniquely match a particular patient. Consequently, the bone engagement surface 1924 can engage the surfaces of the bones of a joint in a single configuration. Such a close matching fit facilitates the surgical osteotomy.

Figure 19A:
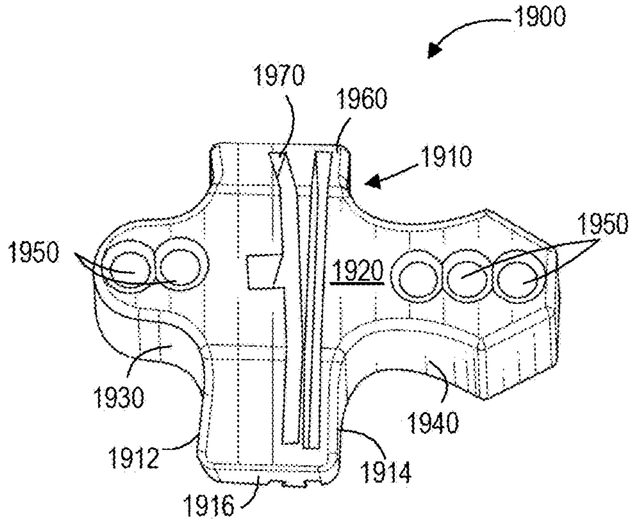
FIGS. 19A-19H are top perspective, top perspective, bottom, front elevation, rear elevation, right, and left, and alternative top perspective, respectively, of a patient-specific cutting guide according to one embodiment.
Figure 19B:
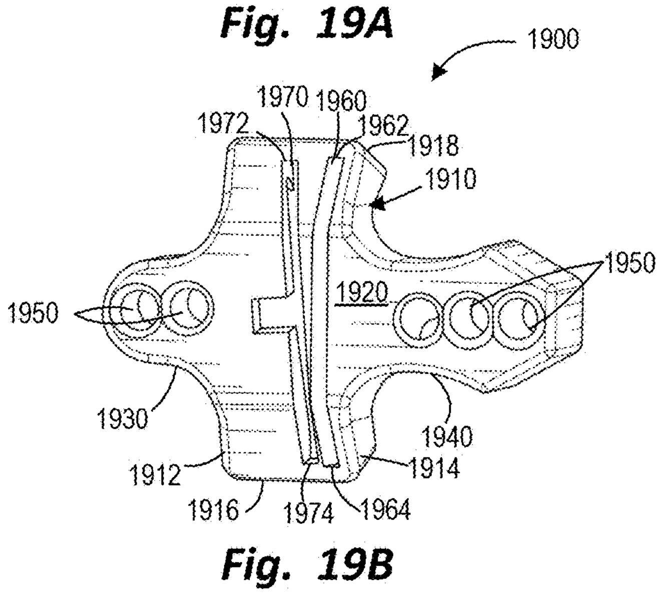
Figure 19C:
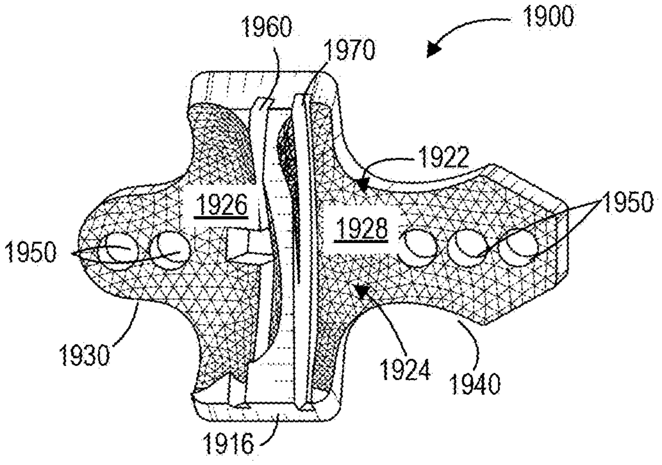
Figure 19D:
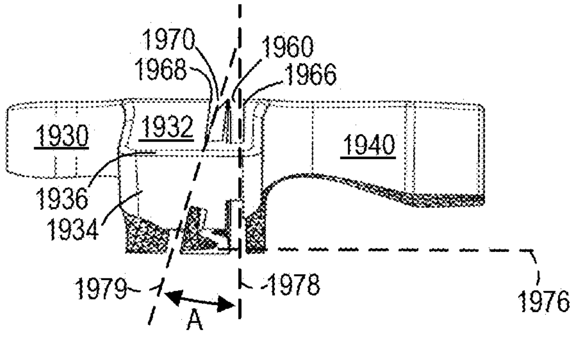
Figure 19E:
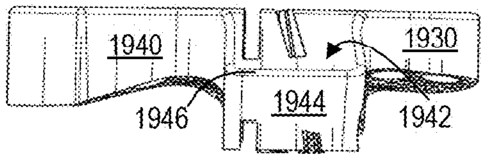
Figure 19F:
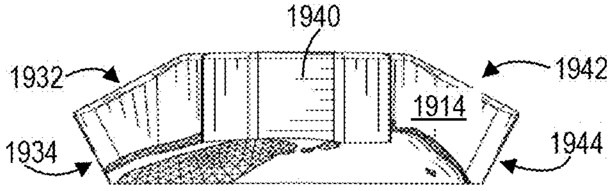
Figure 19G:
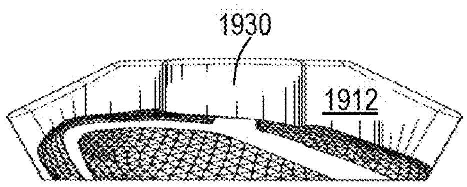

FIG. F 19D illustrates the cutting guide 1900 from a view facing the medial side 1916. FIG. 19E illustrates the cutting guide 1900 from a view facing the lateral side 1918. In certain embodiments, the cutting guide 1900 may include one or more features that facilitate use of the cutting guide 1900 while avoiding certain soft tissue in the vicinity of a joint. For example, the medial side 1916 may include a medial superior surface 1932 and a medial inferior surface 1934 that meet at a medial edge 1936. Advantageously, the medial inferior surface 1934 may extend from inferior side 1922 to the medial edge 1936 at an angle such that the medial inferior surface 1934 does not impinge soft tissue near the joint (e.g., near a medial end of the joint). In certain embodiments, the angle may range between about 80 and about 170 degrees. In another example, the lateral side 1918 may include a lateral superior surface 1942 and a lateral inferior surface 1944 that meet at a lateral edge 1946. Of course, the medial superior surface 1932 may extend from the superior side 1920 to the medial edge 1936 at an angle. The angle of the medial superior surface 1932 may enable use of the cutting guide 1900 in tighter openings and thus minimize the size of incisions used for a procedure.

Advantageously, the lateral inferior surface 1944 may extend from inferior side 1922 to the lateral edge 1946 at an angle such that the lateral inferior surface 1944 does not impinge soft tissue near the joint (e.g., near a medial end of the joint). In certain embodiments, the angle may range between about 80 and about 170 degrees. Of course, the lateral superior surface 1942 may extend from the superior side 1920 to the lateral edge 1946 at an angle. The angle of the lateral superior surface 1942 may enable use of the cutting guide 1900 in tighter openings and thus minimize the size of incisions used for a procedure.

The body 1910 may further include guide features that guide a cutter to resect the first cuneiform and the first metatarsal in the manner needed to make the desired correction. For example, the guide features may be used to guide a planar cutting blade, an arcuate cutting blade, a drill or mill, a burr, and/or the like.

In the embodiment of FIGS. 19A through 19H, the guide features may guide a reciprocating planar blade, such as that of a surgical bone saw, that forms planar cuts in the first cuneiform and the first metatarsal. Various manual or powered tools may be used to form the planar cuts. In one embodiment, a sagittal bone saw can be used. In one example, the guide features may take the form of a first slot 1960 and a second slot 1970. The first slot 1960 may include a lateral end 1962 and a medial end 1964. The second slot 1970 may include a lateral end 1972 and a medial end 1974.

In one embodiment, the first slot 1960 and the second slot 1970 extend from the superior side 1920 to the inferior side 1922. In certain embodiments, the first slot 1960 may extend from near the lateral side 1918 to near the medial side 1916. In other embodiments, one of, or both of, the first slot 1960 and the second slot 1970 may extend from one of the medial side 1916 or the lateral side 1918 of the body 1910. In certain embodiments, the first slot 1960 and second slot 1970 intersect. In other embodiments, the first slot 1960 and second slot 1970 do not intersect.

Thus, upon desired positioning of the cutting guide 1900, the second slot 1970 may be positioned over at least a portion of the first cuneiform to facilitate resection of the first cuneiform, while the first slot 1960 may be positioned over at least a portion of the first metatarsal to facilitate resection of the first metatarsal. In one embodiment, the second slot 1970 is positioned near the distal end of the first cuneiform and the first slot 1960 is positioned near the proximal end of the first metatarsal. The first slot 1960 and second slot 1970 together, with the bone engagement surface 1924 overlying the first cuneiform and the first metatarsal, are positioned to guide resection of the first cuneiform and the first metatarsal during a surgical osteotomy for correcting a condition.

In alternative embodiments, a guide feature may be designed to guide a different type of cutter, such as a drill, mill, or side-cutting burr. In such embodiments, the guide feature may not be a slot, but may instead be a translatable or rotatable cutter retainer that guides translation and/or rotation of the cutter relative to the bone. In certain embodiments, two or more guide features may be replaced by a single guide feature sized to permit a surgeon to resect both a first cuneiform and a first metatarsal using a single cutting guide 1900.

In one embodiment, a first guide feature is configured to define a first cut surface that can be formed by resecting a first bone. A second guide feature is configured to define a second cut surface that can be formed by resecting a second bone. In such an embodiment, one or the other or both of the first cut surface and the second cut surface can be oriented according to one or more angles relative to landmarks on the bones or other anatomical structures.

Alternatively, or in addition, in certain embodiments, one or both of, the first guide feature and second guide feature may be positioned on, or in, the body 1910 and/or have an orientation based on patient imaging data. The patient imaging data can be used to position and orient one, or both, of the first guide feature and second guide feature such that formation of one, or both, of the first cut surface and the second cut surface and fixation of the two cut surfaces against each other mitigates a condition of the patient. For example, as described in the present disclosure, patient imaging data can be used to generate bone models of bones of the patient. The bone models can be used to determine and/or define contours for a bone engagement surface 1924, a position for a first slot 1960, an orientation for a first slot 1960, a position for a second slot 1970, an orientation for a second slot 1970, as well as other features and attributes of one or more patient specific instruments that can be used in a procedure.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface(s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

Figure 20:
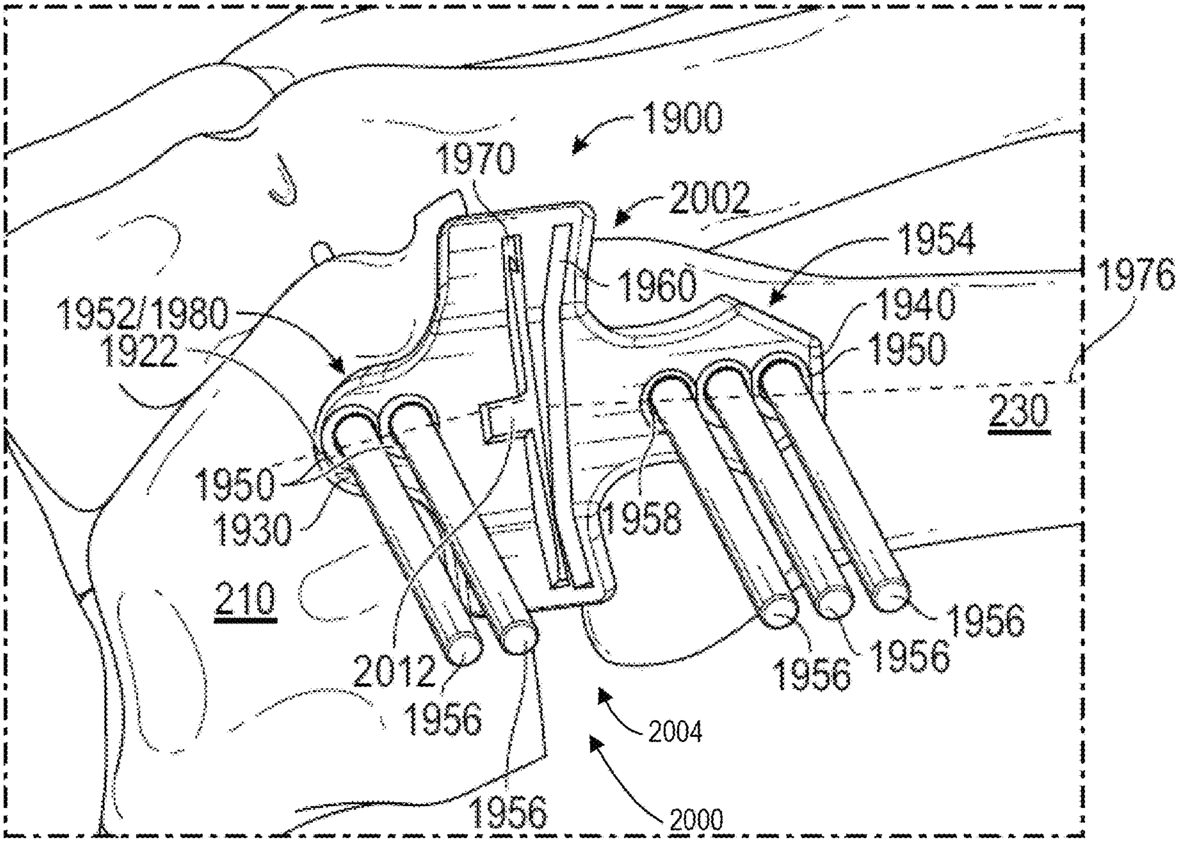
FIG. 20 illustrates a perspective view of a first cuneiform and a first metatarsal with one embodiment of a patient-specific cutting guide positioned over a tarsometatarsal ("TMT") joint.

FIG. 20 illustrates one embodiment of the cutting guide 1900 secured to a first metatarsal 230 and a first cuneiform 210. In the illustrated embodiment, the first guide feature may take the form of the first slot 1960 and the second guide feature may take the form of the second slot 1970. Referring now to FIGS. 20 and 19D, the position and/or angles (e.g., orientation) of one or both of the guide features based on patient imaging data is illustrated. In the illustrated embodiment, the first slot 1960 is positioned between the distal side 1914 and the second slot 1970. The first slot 1960 is oriented based on a desired angle for mitigating the condition of the patient. In one example, the first slot 1960 is angled perpendicular to a longitudinal axis of the first metatarsal 230. This orientation of the first slot 1960 enables the first cut surface to extend from the body 1910 toward the bone to form a cut surface that is also perpendicular to the longitudinal axis 1976 of one of the bones of a joint. "Longitudinal axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point. In the illustrated embodiment, the longitudinal axis 1976 is the longitudinal axis of the first metatarsal 230.

In the illustrated embodiment, the second slot 1970 is positioned between the proximal side 1912 and the first slot 1960. In addition in the illustrated embodiment, the second slot 1970 is oriented based on a desired angle for mitigating the condition of the patient. In the illustrated embodiment, the orientation of the second slot 1970 can be described in reference to a first angle A and a second angle B. FIG. 19D illustrates first angle A. In one embodiment, a second cut surface formed by resection using second slot 1970 extends inferiorly away from a first cut surface formed by resection using first slot 1960. Described another way, angle A is an angle between a first plane 1978 that includes the first slot 1960 and a first cut surface formed by resection using first slot 1960 and a second plane that includes the second slot 1970 and a second cut surface formed by resection using second slot 1970, the second plane extending from the first plane toward the proximal side 1912 of the body 1910. In certain embodiments, angle A can range between about 4 degrees to about 18 degrees. In certain embodiments, angle A may start at 0 degrees and then increase to a positive number of degrees as illustrated or decrease to a negative number of degrees depending on how a surgeon may prescribe adjustments for a correction.

Figure 19H:
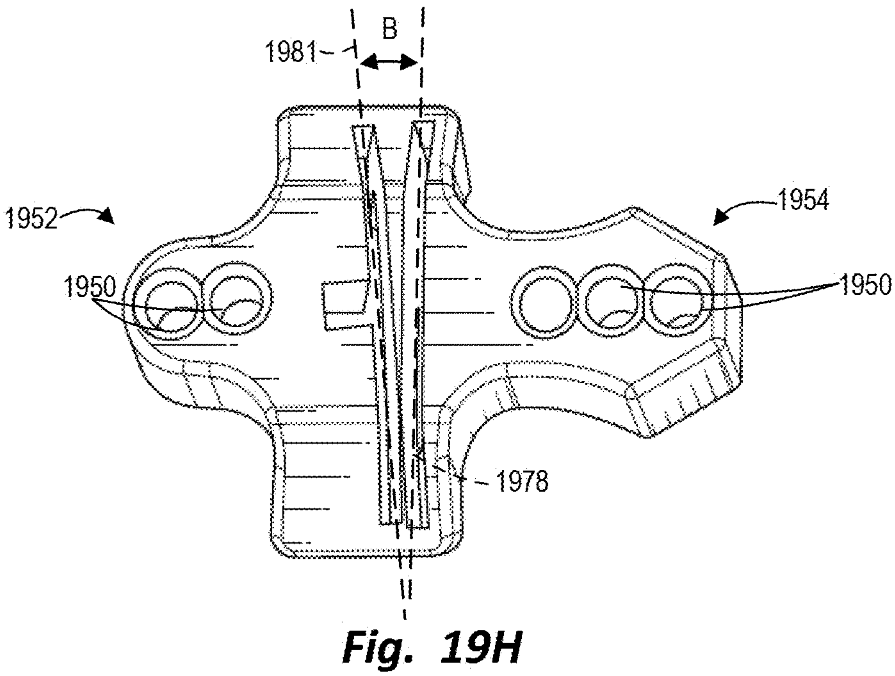

FIG. 19H illustrates second angle B. In one embodiment, a second cut surface formed by resection using second slot 1970 extends posteriorly away from a first cut surface formed by resection using first slot 1960. Described another way, in the illustrated embodiment, angle B is an angle between the first plane 1978 that includes the first slot 1960 and a first cut surface formed by resection using first slot 1960 and a third plane 1981 that includes the second slot 1970 and a second cut surface formed by resection using second slot 1970, the third plane 1981 extending from the first plane toward the proximal side 1912 of the body 1910. In certain embodiments, angle B can range between about 0 degrees to about 35 degrees. In certain embodiments, angle B may start at 0 degrees and then increase to a positive number of degrees as illustrated or decrease to a negative number of degrees depending on how a surgeon may prescribe adjustments for a correction.

Those of skill in the art will appreciate that the position and orientation of the first slot 1960 and second slot 1970 and the corresponding cut surface a surgeon can form using these guide features can vary depending on the anatomical structures of the patient, the osteotomy procedure being performed, preferences of the surgeon, the nature of the condition, and the like. For example in the illustrated embodiment, the medial end 1964 of the first slot 1960 is closer to the medial end 1974 of the second slot 1970 than the lateral end 1962 is in relation to the lateral end 1972. In another embodiment, the lateral end 1962 of the first slot 1960 may be closer to the lateral end 1972 of the second slot 1970 than the medial end 1964 is in relation to the medial end 1974. Of course in another embodiment, the first slot 1960 and second slot 1970 may be configured such that a first distance between lateral end 1962 and lateral end 1972 and a second distance between medial end 1964 and medial end 1974 are substantially the same.

Referring to FIG. 19D, in one embodiment, anatomical data about the patient can be used to define other structures of the cutting guide 1900 or other patient specific instruments. For example, anatomical data about the patient that can be captured in the patient imaging data (e.g., due to the fidelity of the technology providing the patient imaging data) can be used to define how deep a first guide feature and/or second guide feature is. Controlling the depth of the first guide feature and/or second guide feature can be used to manage how deep a surgeon's cutting instruments can reach within the first guide feature and/or second guide feature. Managing a depth for one or more guide features may be referred to as defining a patient specific height for the cutting guide 1900.

For example, in one embodiment, patient imaging data can be used to define a distance between at a first top edge 1966 of the first guide feature (e.g., first slot 1960) and the first surface (e.g., a surface of a first bone such as a first metatarsal 230). Alternatively, or in addition, patient imaging data can be used to define a distance between at a second top edge 1968 of the second guide feature (e.g., second slot 1970) and the second surface (e.g., a surface of a second bone such as a first cuneiform 210). Managing the distance between a first top edge 1966 and/or second top edge 1968 and a bone surface is one way to provide a stop within the cutting guide 1900. The stop can serve to limit how deep a surgeon will resect hard tissue/soft tissue when using the cutting guide 1900 for a procedure. If a surgeon resects until the resection instruments engages the stop, the surgeon can be assured that the resection extends to a desired depth (not too far and not too short).

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

Referring to FIGS. 19H and 20, in one embodiment, the body 1910, or one or more arms, may include one or more bone attachment features that facilitate attachment of the body 1910 to the first cuneiform 210 and/or first metatarsal 230. Such bone attachment features may include any of a wide variety of fasteners including, but not limited to, holes, spikes, fastening devices, and/or the like.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like. In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft. In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

Effective connection of the cutting guide 1900 to one or more bones across a joint can ensure that cut surfaces are formed in desired locations and orientation and mitigate removal of hard tissue and/or soft tissue outside in undesired locations.

Accordingly, the cutting guide 1900 includes one or more bone attachment features. As embodied in FIGS. 19A through 19H, the bone attachment features may take the form of one or more holes 1950 that extend from the inferior side 1922 to the superior side 1920 and/or one or more fixation devices. The holes 1950 may be shaped to accommodate pins, K-wires, and/or other elongated bone fixation elements that can be anchored in the first cuneiform 210 and/or the first metatarsal 230 to keep the cutting guide 1900 in place.

FIG. 20 illustrates one example of a cutting guide 1900 coupled to the bones using a proximal bone attachment feature 1952 and a distal bone attachment feature 1954. In the illustrated embodiment, the proximal bone attachment feature 1952 includes at least one hole 1950 and a fastener and the distal bone attachment feature 1954 includes at least one hole 1950 and a fastener. In FIG. 20 the fasteners are K-wires. Advantageously, the proximal bone attachment feature 1952 and the distal bone attachment feature 1954 each include at least two holes 1950, each with a K-wire passing through the hole 1950 and into bone facing the inferior side 1922. Using two holes 1950 and two fasteners ensures a stable coupling between the cutting guide 1900 and the bone(s). Advantageously, in certain embodiments, the two holes 1950 of the proximal bone attachment feature 1952 and distal bone attachment feature 1954 are align such that inserted K-wires are parallel to each other. Among other benefits, parallel K-wires of each of the proximal bone attachment feature 1952 and distal bone attachment feature 1954 prevent the cutting guide 1900 from pivoting around one of the K-wires of a proximal bone attachment feature 1952 or a distal bone attachment feature 1954.

In the illustrated embodiment, the proximal arm 1930 includes the proximal bone attachment feature 1952 and the distal arm 1940 includes the distal bone attachment feature 1954. In one embodiment, the holes 1950 of the proximal bone attachment feature 1952 are aligned with each other and aligned perpendicular to a guide feature such as the second slot 1970. The holes 1950 of the distal bone attachment feature 1954 may also be aligned with each other and aligned perpendicular to another guide feature such as the first slot 1960. This means that the aligned holes 1950 (and K-wires secured within them) of the distal bone attachment feature 1954 will also be perpendicular to the cut surface formed using the first slot 1960. This also means that the aligned holes 1950 (and K-wires secured within them) of the proximal bone attachment feature 1952 will also be perpendicular to the cut surface formed using the second slot 1970. Consequently, at least one of the proximal bone attachment feature 1952 and the distal bone attachment feature 1954 can be used to position and orient a cut surface of the first metatarsal 230 and a cut surface of the first cuneiform 210.

Returning to FIGS. 19A through 20, the body 1910 may further have features that facilitate desired translation and orientation of the first metatarsal 230 and/or first cuneiform 210 in order to fuse or join the two bones to complete the procedure. For example, in the illustrated embodiment, the cutting guide 1900 may include at least one alignment feature. A second alignment feature may be integrated into the cutting guide 1900 or the second alignment feature may be a separate feature from the cutting guide 1900.

In the illustrated embodiment, the proximal bone attachment feature 1952 serves as both a bone attachment feature and as an alignment feature, e.g., proximal alignment feature 1980. In this manner, the proximal bone attachment feature 1952 can provide both a bone attachment feature and an alignment feature in a single feature. In situations where a second bone of a joint, such as a first metatarsal 230, does not need to be rotated, translated, and/or reoriented to mitigate a patient's condition, the distal bone attachment feature 1954 may also serve as both a bone attachment feature and as an alignment feature, e.g., distal alignment feature 1990.

Typically, in an osteotomy for a condition such as a hallux valgus, it is desirable to rotate the first metatarsal 230 to address the condition. The first metatarsal 230 may be rotated for example to re-position distal plantar sesamoids from a lateral orientation to a more plantar orientation. Research has shown that performing such re-orientation mitigates recurrence of a hallux valgus condition. In such situations, the distal bone attachment feature 1954 may serve as a bone attachment feature and as a reference for the positioning of a distal alignment feature 1990 that is separate from the cutting guide 1900.

For example, in such instances, the distal bone attachment feature 1954 may serve as a reference for placement of a distal alignment feature 1990 (See FIG. 24A) that is parallel to the distal bone attachment feature 1954 as measured along the longitudinal axis 1976 of the first metatarsal 230. Subsequent to formation of a cut surface on the first metatarsal 230, the distal alignment feature 1990 can be coupled to the first metatarsal 230 in parallel to the distal bone attachment feature 1954 (e.g., by way of a pin guide). In certain embodiments, the distal alignment feature 1990 can include two or more aligned holes and/or a pair of K-wires that enter the bone in parallel to each other. In addition, in such a situation, the proximal alignment feature 1980 and the distal alignment feature 1990 may not be aligned initially. Instead, the proximal alignment feature 1980 and distal alignment feature 1990 may be configured to align when the bone coupled to the distal alignment feature 1990 is rotated. Fasteners 1956 of the distal bone attachment feature 1954 may be aligned with longitudinal axis 1976 and perpendicular to first slot 1960 by way of holes 1950. Fasteners 1956 of the proximal bone attachment feature 1952 may be aligned with reference line 1992 and perpendicular to second slot 1970 by way of holes 1950. The reference line 1992 may not be aligned with the longitudinal axis 1976.

FIG. 20 illustrates an example cutting guide 1900 seated transverse to a tarsometatarsal ("TMT") joint 2000. The TMT joint 2000 includes a lateral end 2002 and a medial end 2004. In certain embodiments, such as the illustrated embodiment, the body 1910 is configured to extend between the lateral end 2002 and the medial end 2004. In addition, the proximal arm 1930 and the distal arm 1940 may be aligned with each other.

Figure 23:
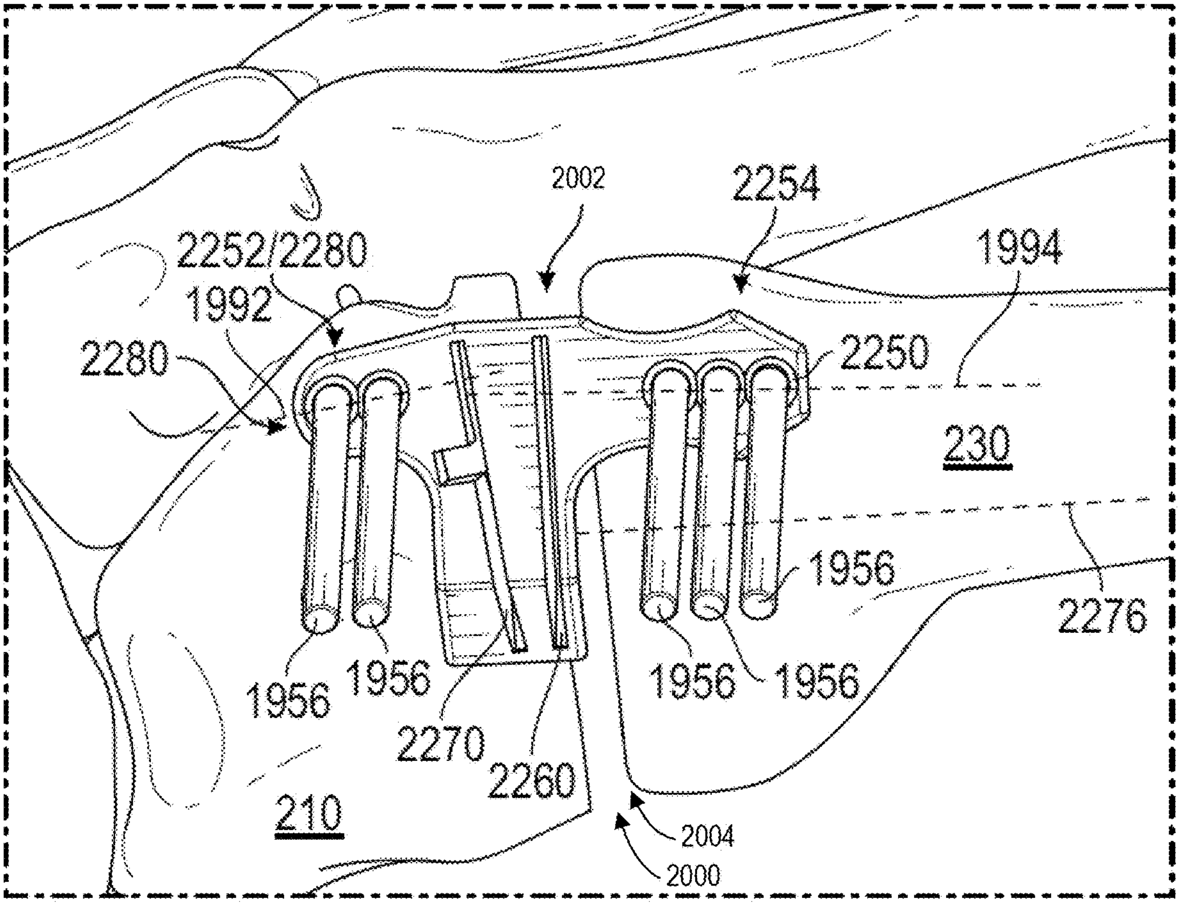
FIG. 23 illustrates a perspective view of a first cuneiform and a first metatarsal with one embodiment of a patient-specific cutting guide positioned over a TMT joint.

Furthermore, in certain embodiments, the proximal arm 1930 and the distal arm 1940 may be positioned extending from the body 1910 near the lateral end 2002 (See FIG. 23). Said another way, the proximal arm 1930 and the distal arm 1940 may be positioned extending from the body 1910 such that the arms extend over a dorsal surface of the first cuneiform 210 and a dorsal surface of the first metatarsal 230. In another embodiment, the proximal arm 1930 and the distal arm 1940 may be positioned extending from the body 1910 near the medial end 2004.

FIG. 20 illustrates an example cutting guide 1900 at a particular stage in an osteotomy procedure. In one embodiment, a surgeon has formed an incision transverse to a TMT joint 2000 with a dorsal approach. In the illustrated embodiment, the cutting guide 1900 may be configured (e.g., the bone engagement surface 1924) to seat between the dorsal surface and medial surface of both the first cuneiform 210 and the first metatarsal 230. The surgeon has also formed the incision down to the cortical bone surface of the first cuneiform 210 and the first metatarsal 230. Further, the surgeon has cut, or moved to the side, soft tissue covering the cortical bone surface of the first cuneiform 210 and the first metatarsal 230 sufficient to seat the bone engagement surface 1924 onto the cortical bone surface of the first cuneiform 210 and the first metatarsal 230.

A surgeon has deployed two or more fasteners 1956 (e.g., K-wires) through the holes 1950 of the proximal bone attachment feature 1952 and the distal bone attachment feature 1954. In certain embodiments, the distal bone attachment feature 1954 and/or the proximal bone attachment feature 1952 can include an additional hole 1958 for another fastener 1956. The additional hole 1958 and fastener 1956 can help keep the cutting guide 1900 in place during resection and alignment operations. In certain embodiments, the additional hole 1958 is aligned with another two holes 1950 of the distal arm 1940 but need not be aligned.

Next, a surgeon can resect a distal articular surface of the first cuneiform 210 and a proximal articular surface of the first metatarsal 230 by way of the second slot 1970 and the first slot 1960. After resection, the distal end of the first cuneiform 210 includes a planar cut surface and the proximal end of the first metatarsal 230 includes a planar cut surface. FIG. 20 illustrates that the bone engagement surface 1924 conforms to the surface of the two bones (e.g., first cuneiform 210 and first metatarsal 230).

Figure 21B:
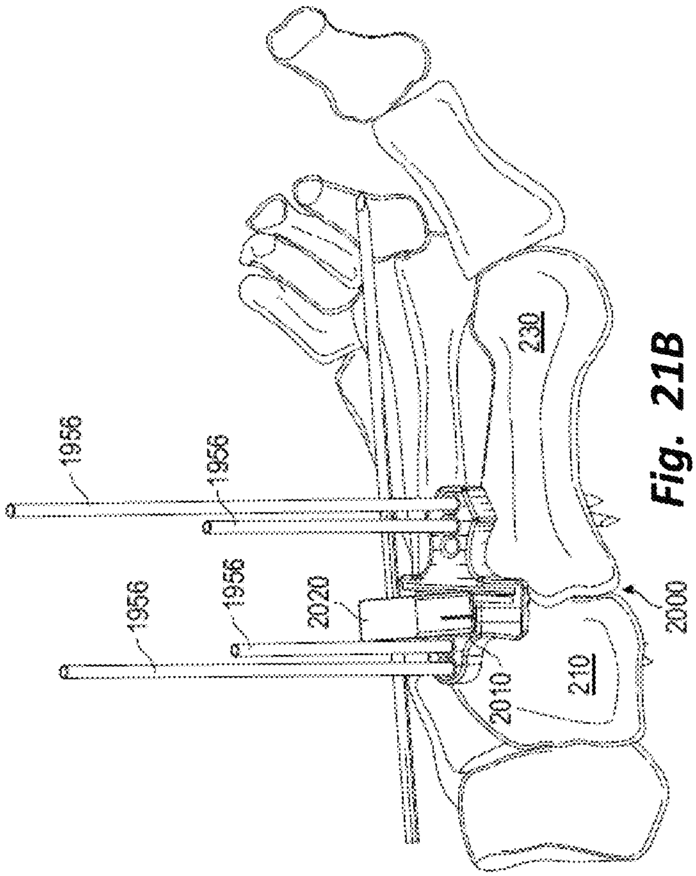
FIGS. 21A, 21B illustrate a perspective view of an alignment guide and of a first cuneiform and a first metatarsal with one embodiment of a patient-specific cutting guide according to one embodiment.
Figure 21A:
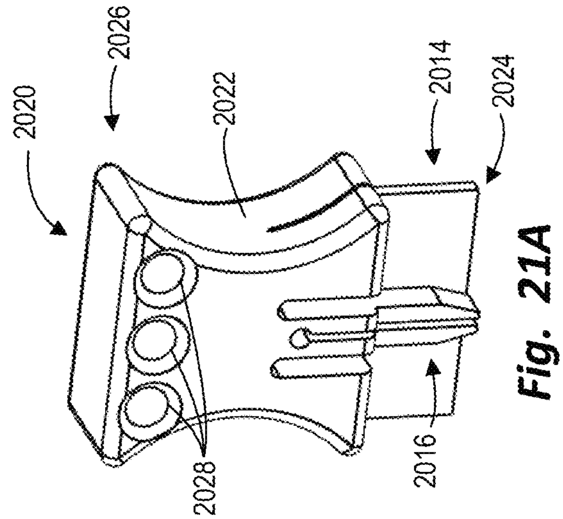

FIGS. 21A, 21B illustrate a perspective view of a first cuneiform and a first metatarsal with one embodiment of a patient-specific cutting guide. Prior to resection completed in the illustrated stage of FIG. 20, a surgeon may desire to check or confirm that the desired cutting guide is being used and that a selected cutting guide will provide a desired alignment between the bones of the foot after the resection and fixation steps.

Accordingly, in the illustrated embodiment, the cutting guide 1900 may include one member of a coupler 2010 configured to engage a corresponding member of the coupler coupled to an alignment guide 2020. Those of skill in the art appreciate that various designs of a coupler may be used. In the illustrated embodiment, the coupler 2010 includes an opening 2012 (See FIG. 20) that may extend from the superior side 1920 into the body 1910 through to the inferior side 1922 and a post 2014. In one embodiment, the opening 2012 may include one of the slots, such as second slot 1970. The post 2014 may include an engagement member 2016.

In one embodiment, the opening 2012 and the post 2014 engage each other in a friction fit. For example, the post 2014 may slide into the second slot 1970 and the engagement member 2016 may slide into the opening 2012. In one embodiment, the engagement member 2016 may include tabs that are biased outward and greater than a diameter of the opening 2012 such that the tabs engage the opening 2012 when inserted and release the opening when the tabs are pressed together.

The alignment guide 2020 includes a body 2022, an inferior end 2024, and superior end 2026 and one or more openings 2028 near the superior end 2026. The openings 2028 may be aligned. A surgeon may use the alignment guide 2020 by engaging the coupler 2010 to couple the alignment guide 2020 to the cutting guide 1900. Next, a surgeon may insert one or more K-wires through the openings. The openings 2028 and alignment guide 2020 may be configured such that K-wires within the openings extend along an anterior-posterior axis and indicate the orientation and alignment of the first cuneiform 210 and first metatarsal 230 once the osteotomy procedure is completed. A surgeon may compare this alignment with the orientation and alignment of other bones of the patient. In this manner, a surgeon can confirm that osteotomy procedure will accomplish the desired outcome once completed.

FIGS. 22A-22H are top perspective, top, bottom, front elevation, rear elevation, right, left, and alternative top perspective, respectively, of a patient-specific cutting guide 2200 according to one embodiment. The cutting guide 2200 may be designed to facilitate resection of a first cuneiform near a distal end and a first metatarsal near a proximal end with planar cuts at the proper angles to provide dual-plane correction of the orientation of the first metatarsal relative to the first cuneiform, thereby providing correction in a lateral direction, in a plantar direction, and/or a dorsal direction.

As shown, the cutting guide 2200 may have a body 2210 with a monolithic construction and the general shape of a rectangular shape. The body 2210 includes a proximal side 2212, a distal side 2214, a medial side 2216, a lateral side 2218, a superior side 2220, and an inferior side 2222. In the illustrated embodiment, the body 2210 may also include a proximal arm 2230 that extends from the body 2210 and a distal arm 2240 that extends from the body 2210. The proximal side 2212 is the side closest to the core of the patient when the cutting guide 2200 is in use. The distal side 2214 is the side furthest from the core of the patient when the cutting guide 2200 is in use. The medial side 2216 is the side facing medially when the cutting guide 2200 is in use. The lateral side 2218 is the side facing laterally when the cutting guide 2200 is in use. The superior side 2220 is the side facing up away from the bone(s) when the cutting guide 2200 is in use. The inferior side 2222 is the side facing down, facing, and/or contacting the bone(s) (e.g., contacting a surface of one or more bones) when the cutting guide 2200 is in use.

The inferior side 2222 may be custom contoured to match the shapes of one or more of the surfaces of the first cuneiform and/or the first metatarsal. In one embodiment, the inferior side 2222 may include a bone engagement surface 2224. The bone engagement surface 2224 can be shaped to match a first surface of a first bone and a second surface of a second bone of a joint.

In one example, the bone engagement surface 2224 can be shaped such that the bone engagement surface 2224 matches a surface of a cuneiform bone and a surface of a metatarsal bone of a tarsometatarsal ("TMT") joint. The bone engagement surface 2224 can be so shaped because it is fabricated from a bone model of the patient's bones. The body 2210 is configured, designed, and/or fabricated to seat transverse to a joint (e.g., a TMT joint) with the bone engagement surface 2224 engaging a first surface of a first bone and a second surface of a second bone.

FIGS. 22A-22H includes similar components, parts, devices, apparatus, features, and aspects as those disclosed and described in relation to FIGS. 19A-19H, however the difference in FIGS. 22A-22H is that body 2210, bone engagement surface 2224, and/or one or more arms (e.g., proximal arm 2230 and/or distal arm 2240) are configured to couple to the bones and extend transverse to the joint, at least partially, if not completely, on the dorsal sides of the bones. Accordingly, the cutting guide 2200 may be referred to as a dorsal cutting guide.

In addition, the cutting guide 2200 may be configured to avoid contact with soft tissue such as nerves, tendons, blood vessels, and the like that may run along a medial and/or a lateral side of the first metatarsal 230. Accordingly, the cutting guide 2200 may be fabricated to seat transverse to the TMT joint such that the bone engagement surface contacts a dorsal surface of the a first bone (e.g., first cuneiform 210) and/or a second bone (e.g., first metatarsal 230). For example, the proximal arm 2230 and/or distal arm 2240 may be positioned more laterally than in other embodiments.

In the illustrated embodiment, the body 2210 is configured to reside on the dorsal surfaces of the first cuneiform and the first metatarsal to provide proper alignment of the body 2210 with the metatarsocuneiform joint (e.g., the joint between the first metatarsal and the medial cuneiform bone, aka a TMT joint). In another embodiment, the body 2210 is configured to reside or sit between the medial surfaces and the dorsal surfaces for an osteotomy.

In certain embodiments, the bone engagement surface 2224 may include a cuneiform apposition portion 2226 and a metatarsal apposition portion 2228. As shown, the cuneiform apposition portion 2226 may be contoured to match the contour of the surface of the first cuneiform on which it is to rest, and the metatarsal apposition portion 2228 may similarly be contoured to match the contour of the surface of the first metatarsal on which it is to rest. (See FIG. 22C) Thus, the body 2210 may have only one stable position and orientation relative to the first cuneiform and the first metatarsal during a surgical osteotomy for correcting the condition.

Advantageously, the fidelity of the patient imaging data enables the bone model, preliminary cutting guide model, and patient specific instrument (e.g., patient specific cutting guide, patient specific pin guide, patient specific alignment guide, etc.) to uniquely match a particular patient. Consequently, the bone engagement surface 2224 can engage the surfaces of the bones of a joint in a single configuration. Such a close matching fit facilitates the surgical osteotomy.

Figure 22A:
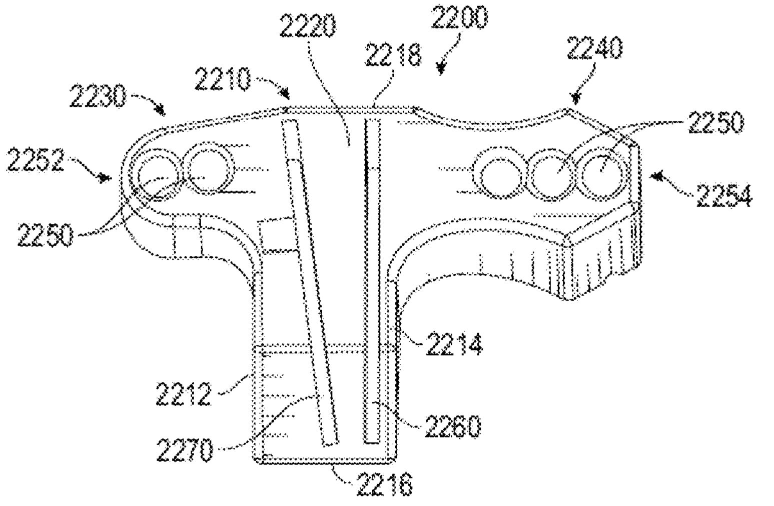
FIGS. 22A-22H are top perspective, top, bottom, front elevation, rear elevation, right, left, and alternative top perspective, respectively, of a patient-specific cutting guide according to one embodiment.
Figure 22B:
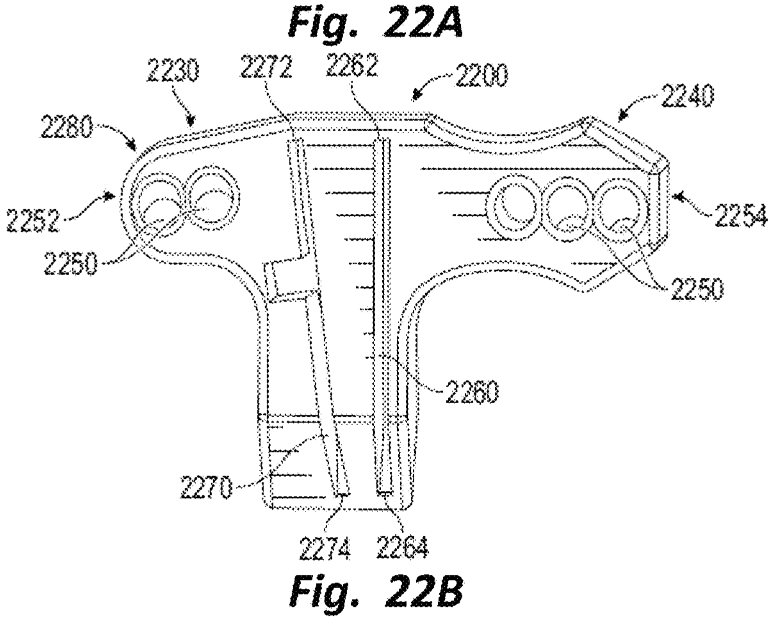
Figure 22C:
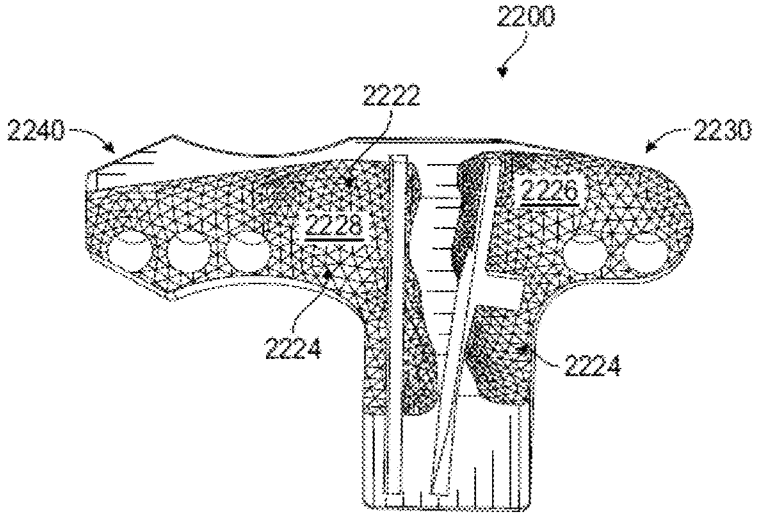
Figure 22F:
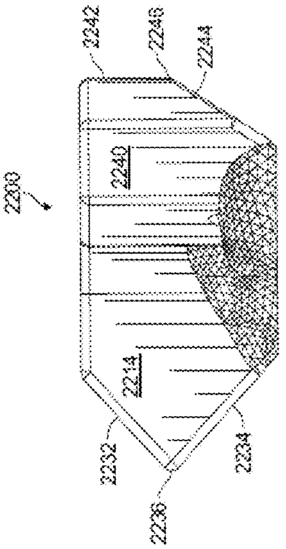
Figure 22E:
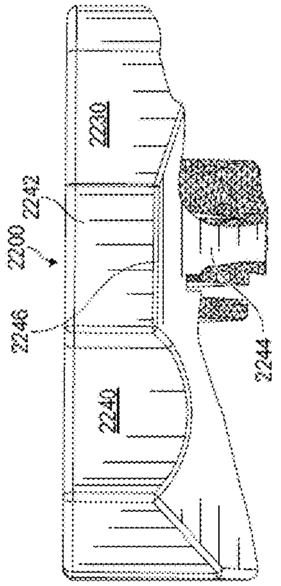

FIG. F 22D illustrates the cutting guide 2200 from a view facing the medial side 2216. FIG. 22E illustrates the cutting guide 2200 from a view facing the lateral side 2218. In certain embodiments, the cutting guide 2200 may include one or more features that facilitate use of the cutting guide 2200 while avoiding certain soft tissue in the vicinity of a joint. For example, the medial side 2216 may include a medial superior surface 2232 and a medial inferior surface 2234 that meet at a medial edge 2236. Advantageously, the medial inferior surface 2234 may extend from inferior side 2222 to the medial edge 2236 at an angle such that the medial inferior surface 2234 does not impinge soft tissue near the joint (e.g., near a medial end of the joint). In certain embodiments, the angle may range between about 80 and 170 degrees. In another example, the lateral side 2218 may include a lateral superior surface 2242 and a lateral inferior surface 2244 that meet at a lateral edge 2246 (See FIG. 22E). Of course, the medial superior surface 2232 may extend from the superior side 2220 to the medial edge 2236 at an angle. The angle of the medial superior surface 2232 may enable use of the cutting guide 2200 in tighter openings and thus minimize the size of incisions used for a procedure.

Advantageously, the lateral inferior surface 2244 may extend from inferior side 2222 to the lateral edge 2246 at an angle such that the lateral inferior surface 2244 does not impinge soft tissue near the joint (e.g., near a medial end of the joint). In certain embodiments, the angle may range between about 80 and 170 degrees. Of course, the lateral superior surface 2242 may extend from the superior side 2220 to the lateral edge 2246 at an angle. The angle of the lateral superior surface 2242 may enable use of the cutting guide 2200 in tighter openings and thus minimize the size of incisions used for a procedure.

The body 2210 may further include guide features that guide a cutter to resect the first cuneiform and the first metatarsal in the manner needed to make the desired correction. For example, the guide features may be used to guide a planar cutting blade, an arcuate cutting blade, a drill or mill, a burr, and/or the like.

In the embodiment of FIGS. 22A through 22H, the guide features may guide a reciprocating planar blade, such as that of a surgical bone saw, that forms planar cuts in the first cuneiform and the first metatarsal. Various manual or powered tools may be used to form the planar cuts. In one embodiment, a sagittal bone saw can be used. In one example, the guide features may take the form of a first slot 2260 and a second slot 2270. The first slot 2260 may include a lateral end 2262 and a medial end 2264. The second slot 2270 may include a lateral end 2272 and a medial end 2274.

In one embodiment, the first slot 2260 and the second slot 2270 extend from the superior side 2220 to the inferior side 2222. In certain embodiments, the first slot 2260 may extend from near the lateral side 2218 to near the medial side 2216. In other embodiments, one of, or both of, the first slot 2260 and the second slot 2270 may extend from one of the medial side 2216 or the lateral side 2218 of the body 2210. In certain embodiments, the first slot 2260 and second slot 2270 intersect. In other embodiments, the first slot 2260 and second slot 2270 do not intersect.

Thus, upon desired positioning of the cutting guide 2200, the second slot 2270 may be positioned over at least a portion of the first cuneiform to facilitate resection of the first cuneiform, while the first slot 2260 may be positioned over at least a portion of the first metatarsal to facilitate resection of the first metatarsal. In one embodiment, the second slot 2270 is positioned near the distal end of the first cuneiform and the first slot 2260 is positioned near the proximal end of the first metatarsal. The first slot 2260 and second slot 2270 together, with the bone engagement surface 2224 overlying the first cuneiform and the first metatarsal, are positioned to guide resection of the first cuneiform and the first metatarsal during a surgical osteotomy for correcting a condition.

In alternative embodiments, a guide feature may be designed to guide a different type of cutter, such as a drill, mill, or side-cutting burr. In such embodiments, the guide feature may not be a slot, but may instead be a translatable or rotatable cutter retainer that guides translation and/or rotation of the cutter relative to the bone. In certain embodiments, two or more guide features may be replaced by a single guide feature sized to permit a surgeon to resect both a first cuneiform and a first metatarsal using a single cutting guide 2200.

In one embodiment, a first guide feature is configured to define a first cut surface that can be formed by resecting a first bone. A second guide feature is configured to define a second cut surface that can be formed by resecting a second bone. In such an embodiment, one or the other or both of the first cut surface and the second cut surface can be oriented according to one or more angles relative to landmarks on the bones or other anatomical structures.

Alternatively, or in addition, in certain embodiments, one or both of, the first guide feature and second guide feature may be positioned on, or in, the body 2210 and/or have an orientation based on patient imaging data. The patient imaging data can be used to position and orient one, or both, of the first guide feature and second guide feature such that formation of one, or both, of the first cut surface and the second cut surface and fixation of the two cut surfaces against each other mitigates a condition of the patient. For example, as described in the present disclosure, patient imaging data can be used to generate bone models of bones of the patient. The bone models can be used to determine and/or define contours for a bone engagement surface 2224, a position for a first slot 2260, an orientation for a first slot 2260, a position for a second slot 2270, an orientation for a second slot 2270, as well as other features and attributes of one or more patient specific instruments that can be used in a procedure.

FIG. 23 illustrates a perspective view of a first cuneiform and a first metatarsal with one embodiment of a patient-specific cutting guide positioned over a TMT joint. In the illustrated embodiment, the first guide feature may take the form of the first slot 2260 and the second guide feature may take the form of the second slot 2270. As with the embodiment of FIGS. 19A-19H and 20, the position and/or angles (e.g., orientation) of one or both of the guide features based on patient imaging data is illustrated. The first slot 2260 is oriented based on a desired angle for mitigating the condition of the patient. In one example, the first slot 2260 is angled perpendicular to a longitudinal axis 2276 of the first metatarsal 230. This orientation of the first slot 2260 enables the first cut surface to extend from the body 2210 toward the bone to form a cut surface that is also perpendicular to the longitudinal axis 2276 of one of the bones of a joint.

In the illustrated embodiment, the second slot 2270 is positioned and oriented based on a desired angle for mitigating the condition of the patient. In the illustrated embodiment, the orientation of the second slot 2270 can be described in reference to a first angle A and a second angle B, just as those angles are described above in relation to FIGS. 19D and 19H.

Those of skill in the art will appreciate that the position and orientation of the first slot 2260 and second slot 2270 and the corresponding cut surface a surgeon can form using these guide features can vary depending on the anatomical structures of the patient, the osteotomy procedure being performed, preferences of the surgeon, the nature of the condition, and the like.

Figure 22H:
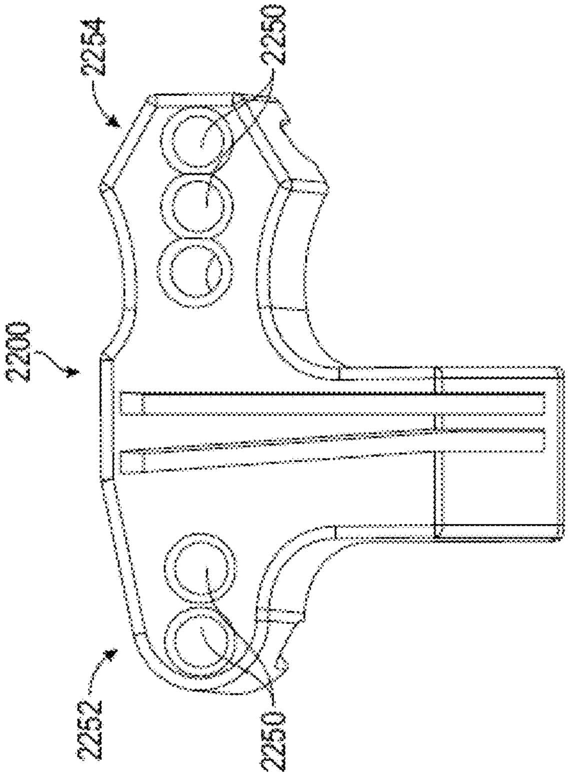
Figure 22D:
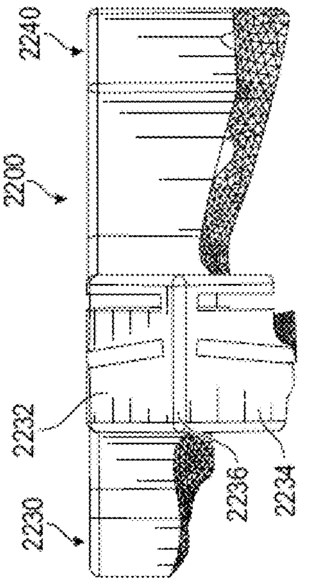
Figure 22G:
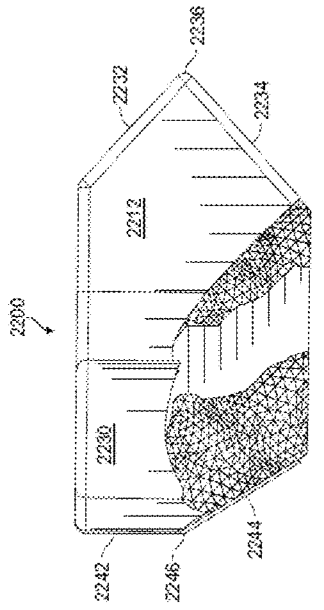

Referring to FIGS. 22H and 23, in one embodiment, the body 2210, or one or more arms, may include one or more bone attachment features that facilitate attachment of the body 2210 to the first cuneiform 210 and/or first metatarsal 230. Such bone attachment features may include any of a wide variety of fasteners including, but not limited to, holes, spikes, fastening devices, and/or the like. Effective connection of the cutting guide 2200 to one or more bones across a joint can ensure that cut surfaces are formed in desired locations and orientation and mitigate removal of hard tissue and/or soft tissue outside in undesired locations.

Accordingly, the cutting guide 2200 includes one or more bone attachment features. As embodied in FIGS. 22A through 22H, the bone attachment features may take the form of one or more holes 2250 that extend from the inferior side 2222 to the superior side 2220 and/or one or more fixation devices. The holes 2250 may be shaped to accommodate pins, K-wires, and/or other elongated bone fixation elements that can be anchored in the first cuneiform 210 and/or the first metatarsal 230 to keep the cutting guide 2200 in place.

FIG. 23 illustrates one example of a cutting guide 2200 coupled to the bones using a proximal bone attachment feature 2252 and a distal bone attachment feature 2254. In the illustrated embodiment, the proximal bone attachment feature 2252 includes at least one hole 2250 and a fastener and the distal bone attachment feature 2254 includes at least one hole 2250 and a fastener. In FIG. 23 the fasteners are K-wires. Advantageously, the proximal bone attachment feature 2252 and the distal bone attachment feature 2254 each include at least two holes 2250, each with a K-wire passing through the hole 2250 and into bone facing the inferior side 2222. Using two holes 2250 and two fasteners ensures a stable coupling between the cutting guide 2200 and the bone(s). Advantageously, in certain embodiments, the two holes 2250 of the proximal bone attachment feature 2252 and distal bone attachment feature 2254 are align such that inserted K-wires are parallel to each other. Among other benefits, parallel K-wires of each of the proximal bone attachment feature 2252 and distal bone attachment feature 2254 prevent the cutting guide 2200 from pivoting around one of the K-wires of a proximal bone attachment feature 2252 or a distal bone attachment feature 2254.

In the illustrated embodiment, the proximal arm 2230 includes the proximal bone attachment feature 2252 and the distal arm 2240 includes the distal bone attachment feature 2254. In one embodiment, the holes 2250 of the proximal bone attachment feature 2252 are aligned with each other and aligned perpendicular to a guide feature such as the second slot 2270 (see reference line 1992). The holes 2250 of the distal bone attachment feature 2254 may also be aligned with each other and aligned perpendicular to another guide feature such as the first slot 2260 (see reference line 1994). This means that the aligned holes 2250 (and K-wires secured within them) of the distal bone attachment feature 2254 will also be perpendicular to the cut surface formed using the first slot 2260. This also means that the aligned holes 2250 (and K-wires secured within them) of the proximal bone attachment feature 2252 will also be perpendicular to the cut surface formed using the second slot 2270. Consequently, at least one of the proximal bone attachment feature 2252 and the distal bone attachment feature 2254 can be used to position and orient a cut surface of the first metatarsal 230 and a cut surface of the first cuneiform 210. In certain embodiments, the proximal bone attachment feature 2252 and distal bone attachment feature 2254 may not be aligned with each other, the offset in the alignment may be the change in orientation of the bones of the joint desired to address the condition. It should be noted that the distal bone attachment feature 2254 may be parallel to the longitudinal axis 2276. In this manner, the distal bone attachment feature 2254 can be used as a reference for positioning a distal alignment feature 2290 on the first metatarsal 230.

Returning to FIGS. 22A through 20, the body 2210 may further have features that facilitate desired translation and orientation of the first metatarsal 230 and/or first cuneiform 210 in order to fuse or join the two bones to complete the procedure. For example, in the illustrated embodiment, the cutting guide 2200 may include at least one alignment feature. A second alignment feature may be integrated into the cutting guide 2200 or the second alignment feature may be a separate feature from the cutting guide 2200.

In the illustrated embodiment, the proximal bone attachment feature 2252 serves as both a bone attachment feature and as an alignment feature, e.g., proximal alignment feature 2280. In this manner, the proximal bone attachment feature 2252 can provide both a bone attachment feature and an alignment feature in a single feature. In situations where a second bone of a joint, such as a first metatarsal 230, does not need to be rotated, translated, and/or reoriented to mitigate a patient's condition, the distal bone attachment feature 2254 may also serve as both a bone attachment feature and as an alignment feature, e.g., distal alignment feature 2290.

Typically, in an osteotomy for a condition such as a hallux valgus, it is desirable to rotate the first metatarsal 230 to address the condition. The first metatarsal 230 may be rotated for example to re-position distal plantar sesamoids from a lateral orientation to a more plantar orientation. Research has shown that performing such re-orientation mitigates recurrence of a hallux valgus condition. In such situations, the distal bone attachment feature 2254 may serve as a bone attachment feature and as a reference for the positioning of a distal alignment feature 2290 that is separate from the cutting guide 2200.

For example, in such instances, the distal bone attachment feature 2254 may serve as a reference for placement of a distal alignment feature 2290 (See FIG. 24A) that is parallel to the distal bone attachment feature 2254 as measured along the longitudinal axis 2276 of the first metatarsal 230. Subsequent to formation of a cut surface on the first metatarsal 230, the distal alignment feature 2290 can be coupled to the first metatarsal 230 in parallel to the distal bone attachment feature 2254 (e.g., by way of a pin guide). In certain embodiments, the distal alignment feature 2290 can include two or more aligned holes and/or a pair of K-wires that enter the bone in parallel to each other. In addition, in such a situation, the proximal alignment feature 2280 and the distal alignment feature 2290 may not be aligned initially. Instead, the proximal alignment feature 2280 and distal alignment feature 2290 may be configured to align when the bone coupled to the distal alignment feature 2290 is rotated.

FIG. 23 illustrates an example cutting guide 2200 seated transverse to a tarsometatarsal ("TMT") joint 2000. The TMT joint 2000 includes a lateral end 2002 and a medial end 2004. In certain embodiments, such as the illustrated embodiment, the body 2210 is configured to extend between the lateral end 2002 and the medial end 2004. In this manner, the first slot 2260 and second slot 2270 extend along the TMT joint 2000 in a lateral medial direction and are long enough that a surgeon can readily resect the respective ends of the respective bones of the joint. In addition, the proximal arm 2230 and the distal arm 2240 may be aligned with each other. In one embodiment, the proximal arm 2230 and distal arm 2240 may extend proximal to the lateral side 2218 and/or proximal to the lateral end 2002 of the joint (e.g., TMT joint 2000).

Advantageously, the cutting guide 2200 can be used with patients that have smaller bones and joints such as children or female patients. The cutting guide 2200 fits directly on the dorsal surfaces of the bones of the joint. This placement can avoid contact with soft tissues that may run along the medial and/or lateral surfaces of the bones of the joint.

FIG. 23 illustrates that the cutting guide 2200 can be secured to the bones using the proximal bone attachment feature 2252 and/or distal bone attachment feature 2254 each of which may include two or more fasteners 1956. In certain embodiments, the fasteners 1956 of the proximal bone attachment feature 2252 are aligned with each other and perpendicular to the second slot 2270. The fasteners 1956 of the distal bone attachment feature 2254 are aligned with each other and perpendicular to the first slot 2260. The fit of the bone engagement surface 2224 to the surfaces (dorsal in this embodiment) of the bones helps to secure the cutting guide 2200 in place and ensure that resection of the bones using the first slot 2260 and second slot 2270 forms the desired cut surfaces for the procedure.

Those of skill in the art will appreciate that in various embodiments certain aspects may interface with one or more dorsal surfaces of each or both of the bones of a joint. The illustrated embodiments provide at least one example. In other embodiments, at least one of a cutting guide body, a proximal arm, a distal arm, and a bone engagement surface of a inferior surface of the body is configured to engage a dorsal surface of one or more of a first bone and a second bone.

It should be noted that the cutting guide 1900 and/or cutting guide 2200 may be configured to engage with a dorsal surface of one bone (e.g., a first cuneiform 210) and a lateral surface of a second bone (e.g., a first metatarsal 230) of a joint (e.g., TMT joint 2000). For example, where the patient has a hallux valgus condition, the first metatarsal 230 may have rotated about its longitudinal axis 1976/2276 such that the lateral surface of the first metatarsal 230 faces dorsal. Advantageously, the present disclosure accounts for this and the cutting guide 1900/2200 is configured to contact a dorsal surface on one bone and a lateral surface of the second bone (or proximal surface if the bone is rotated in the other direction). Furthermore, the proximal alignment feature 1980/2280 may engage with a dorsal surface of a proximal bone and the distal alignment feature 1990/2290 may engage with a dorsal surface of a distal bone, even though the distal bone has rotated.

Figure 24A:
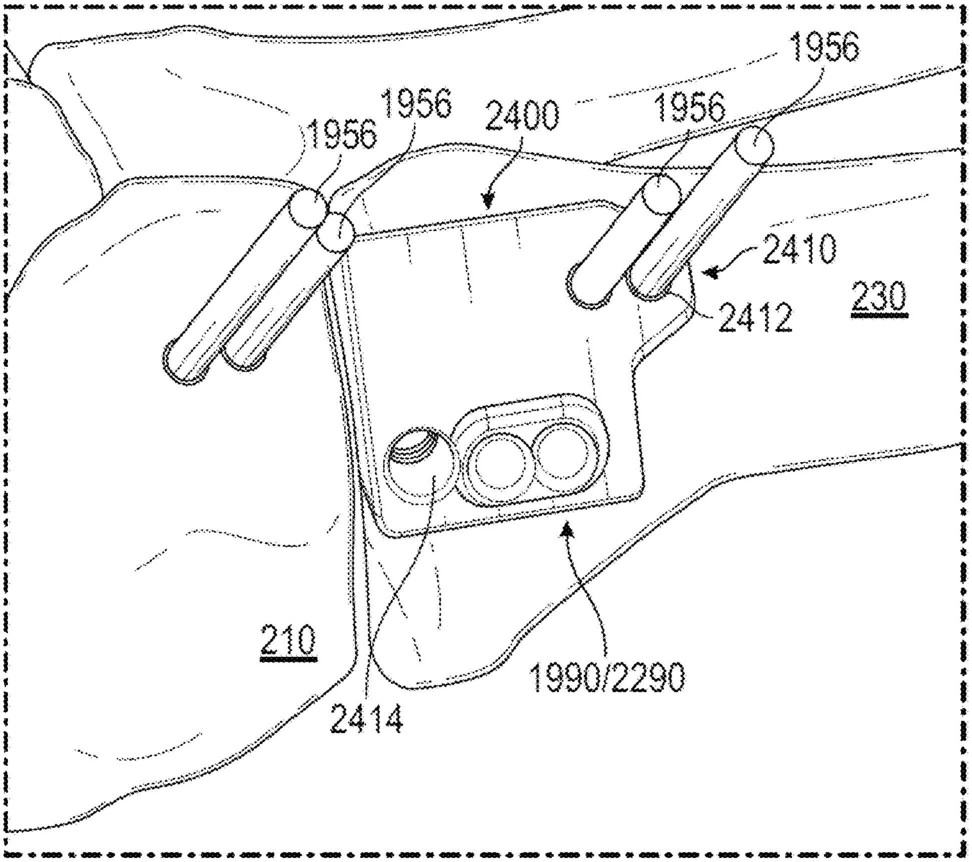
FIG. 24A illustrates a perspective view of the first cuneiform and the first metatarsal of FIG. 23 with one embodiment of a pin guide.

Referring to FIGS. 20 and 23, in the illustrated embodiments, the proximal alignment feature 1980/2280 and distal alignment feature 1990/2290 may be in separate devices rather than being combined in a single device. FIGS. 20 and 23 show the proximal alignment feature 1980/2280 as part of the cutting guide 1900/2200. FIG. 24A illustrates a distal alignment feature 1990/2290 that is part of a separate device. FIG. 24A illustrates a perspective view of the first cuneiform and the first metatarsal of FIGS. 20, 23 with one embodiment of a pin guide 2400 that includes a distal alignment feature 1990/2290.

FIG. 24A illustrates a perspective view of the first cuneiform 210 and the first metatarsal 230 of FIG. 23 after resection of the bones. After resection, a surgeon remove the cutting guide 1900/2200 by sliding it off of the fasteners 1956 and keep the fasteners 1956 connected to the bones. The fasteners 1956 on the first cuneiform 210 can serve as a proximal alignment feature 1980/2280. The fasteners 1956 on the first metatarsal 230 can serve as a guide for a distal alignment feature 1990/2290. For example, the surgeon can slide pin guide 2400 over the fasteners 1956 on the first metatarsal 230. The pin guide 2400 can then identify where to position the distal alignment feature 1990/2290.

The pin guide 2400 includes a bone attachment feature 2410 realized by a pair of holes 2412 that extend from a superior surface to an inferior surface. Advantageously, the holes 2412 can engage with the fasteners 1956 (which have remained in the bone) used with the cutting guide 1900/2200.

The pin guide 2400 also includes a distal alignment feature 1990/2290. In certain embodiments, the distal alignment feature 1990/2290 is offset from the bone attachment feature 2410. In certain embodiments, the bone attachment feature 2410 is offset from the bone attachment feature 2410 by a certain distance that corresponds to a number of degrees of rotation of the first metatarsal 230 from an original position to a new positioned after rotating the first metatarsal 230 about its longitudinal axis 1976/2276. The first metatarsal 230 can be rotated a certain number of degrees about its longitudinal axis 1976/2276 in either a clockwise or a counterclockwise direction. Typically, the first metatarsal 230 is rotated counterclockwise to address a condition such as a hallux valgus condition.

Figure 24B:
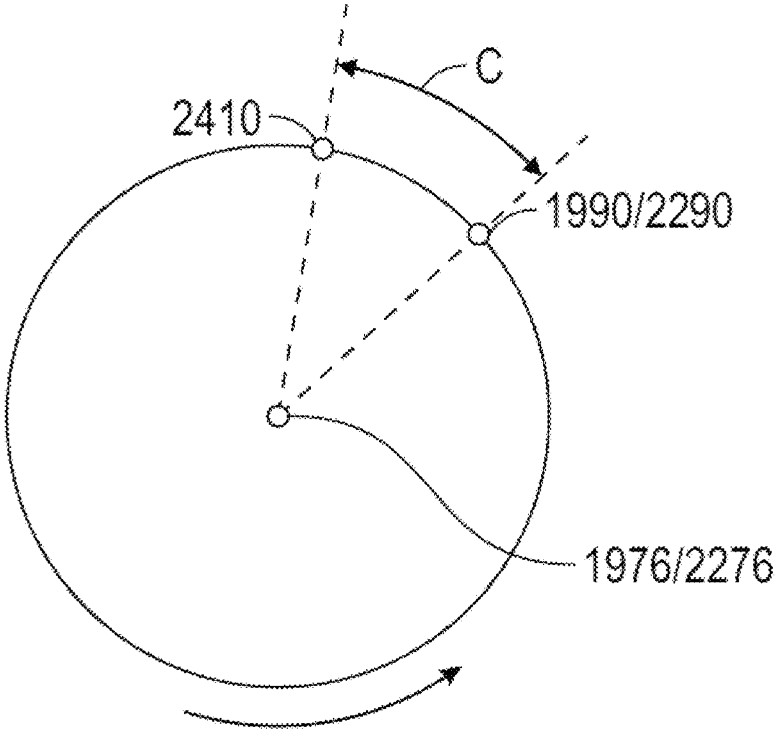
FIG. 24B illustrates a diagram representative of a cross-sectional view of first metatarsal 230 from a proximal base looking towards the distal head.

FIG. 24B illustrates a diagram representative of a cross-sectional view of a first metatarsal 230 from a proximal base (represented as a circle) looking towards the distal head. FIG. 24B illustrates the relationship between the bone attachment feature 2410 and the distal alignment feature 1990/2290. Angle C represents the number of degrees between the first positioned and the second position that the bone will be rotated to once rotated about the longitudinal axis 1976/2276. In certain embodiments, angle C may range between about 0 and about 35 degrees.

Referring now to FIG. 24A, a surgeon may not know per-operatively how much rotation is needed or can be achieved given the condition and anatomy of the patient. Accordingly, the present disclosure may include a number of pin guides 2400 each with a different number of degrees of correction built into the placement of the distal alignment feature 1990/2290 relative to the bone attachment feature 2410. Examples include a 25 degree pin guide 2400, 30 degree pin guide 2400, 35 degree pin guide 2400, 40 degree pin guide 2400, 10 degree pin guide 2400, 15 degree pin guide 2400, and the like. Each pin guide 2400 that provides a different number of degrees of rotation may include a marking that identifies the number of degrees (e.g., "25", "30", etc.). Alternatively, or in addition, certain pin guide 2400 may be configured for use on a joint of a left foot versus a right foot. Similarly, such pin guide 2400 may include an indicator of which foot the guide is to be used with (e.g., "Left", "Right"). Those of skill in the art will appreciate that the degrees for the pin guide 2400 may range from about 2 degrees to about 100 degrees.

In the illustrated embodiment, the bone attachment feature 2410 is perpendicular to the first slot 1960/2260 and parallel to the distal alignment feature 1990/2290 that can be coupled to the first metatarsal 230.

In one embodiment, after a surgeon selects that desired amount of offset by choosing a pin guide 2400 with a desired number of degrees, the surgeon positions the selected pin guide 2400 on the first metatarsal 230 by sliding the holes 2412 over the fasteners 1956. Placement of the pin guide 2400 positions the distal alignment feature 1990/2290 for subsequent rotation of the bone. Next, a surgeon may insert two fasteners 1956 into holes of the distal alignment feature 1990/2290. The fasteners 1956 may mark the position for alignment and sit securely in the bone.

Next a surgeon may de-rotate or rotate the first metatarsal 230 for subsequent fusion to the first cuneiform 210. De-rotation refers to rotation of the first metatarsal 230 about the longitudinal axis 1976/2276 such that the first metatarsal 230 assumes a position before the condition presented, for example a hallux valgus condition. As noted de-rotation may mean rotating the first metatarsal 230 counterclockwise.

Figure 24C:
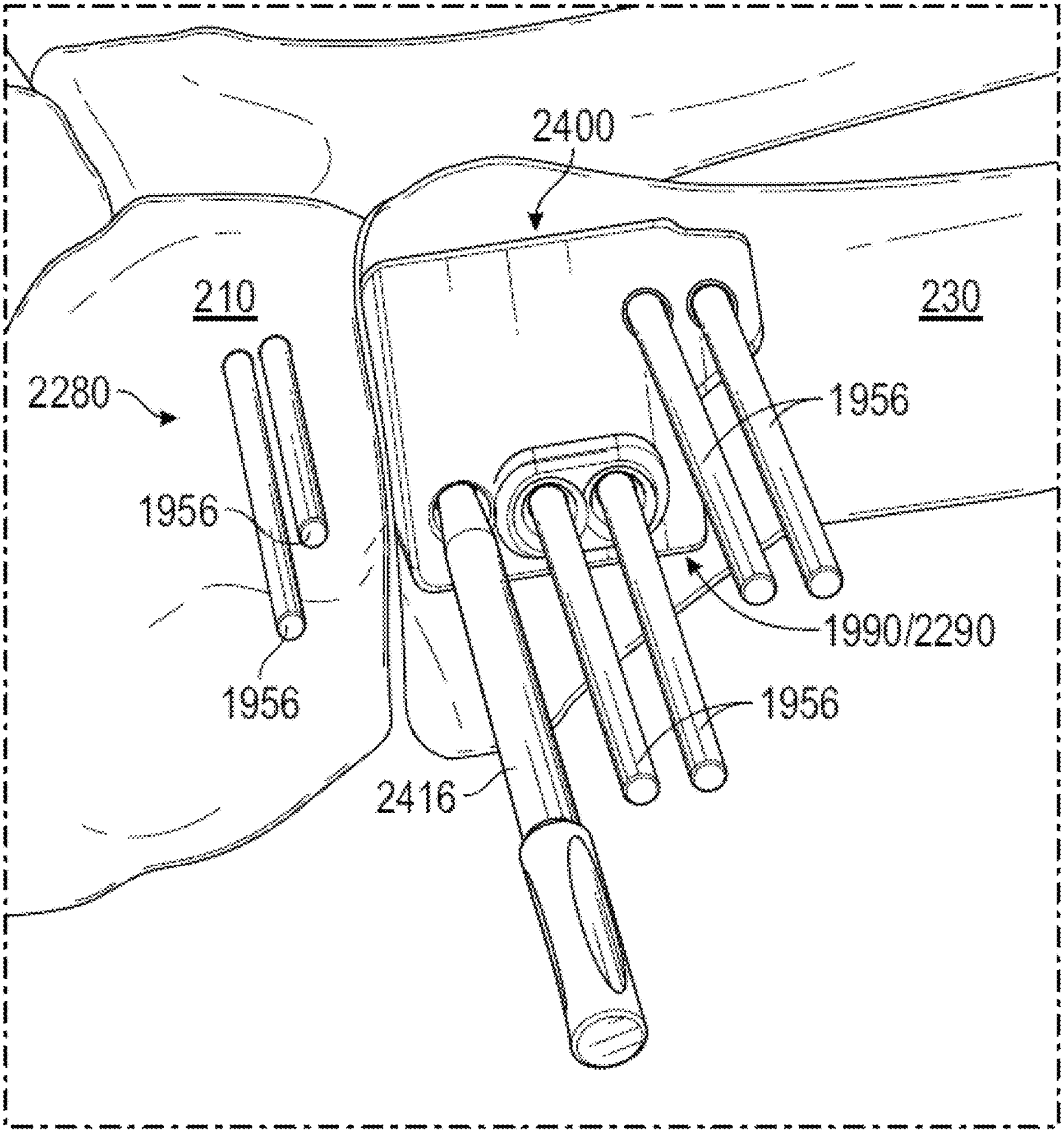
FIG. 24C illustrates a perspective view of the first cuneiform and the first metatarsal of FIG. 24A with a pin guide connected.

FIG. 24C shows one way de-rotation may be performed. FIG. 24C illustrates a perspective view of the first cuneiform and the first metatarsal of FIG. 24A with a pin guide connected. A surgeon may use various ways, devices, or methods to de-rotate the first metatarsal 230. In one embodiment, the pin guide 2400 may include a coupler, such as a threaded hole 2414 configured to thread onto an end of a handle 2416. A surgeon may connect the handle 2416 to the pin guide 2400 by way of the threaded hole 2414. A surgeon can then use the handle 2416 to guide and rotate or de-rotate the first metatarsal 230 into a desired position. In the illustrated embodiment, the surgeon may de-rotate the first metatarsal 230 until the distal alignment feature 1990/2290 substantially aligns with the proximal alignment feature 1980/2280. Alternatively, or in addition, the surgeon may rotate the first metatarsal 230 using fasteners 1956 of the distal alignment feature 1990/2290 and/or the bone attachment feature 2410.

Figure 25A:
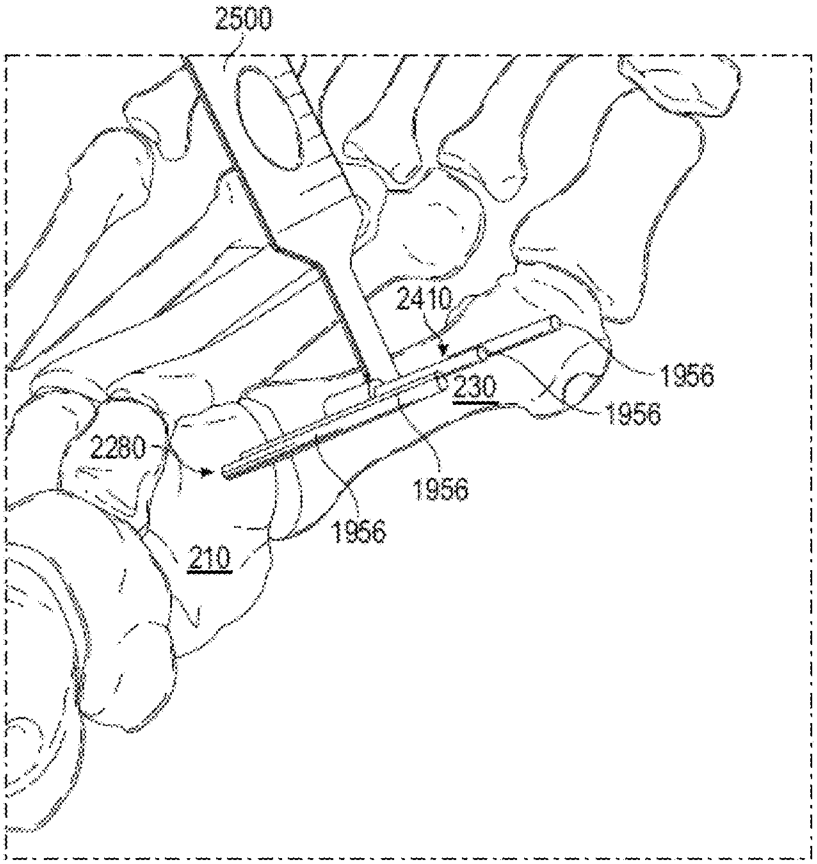
FIG. 25A illustrates a perspective view of the first cuneiform and the first metatarsal of FIG. 23 with one embodiment of a de-rotation handle.

FIG. 25A illustrates a perspective view of the first cuneiform and the first metatarsal of FIG. 23 with one embodiment of a de-rotation handle. As an alternative to using a pin guide 2400 a surgeon may connect a de-rotation handle 2500 to fasteners 1956 of the distal bone attachment feature 1954/2254. The de-rotation handle 2500 may be connected to extend laterally such that once the first metatarsal 230 is de-rotated two more fasteners 1956 can be inserted into the first metatarsal 230 at a position that substantially aligns with the proximal alignment feature 1980/2280.

Figure 25B:
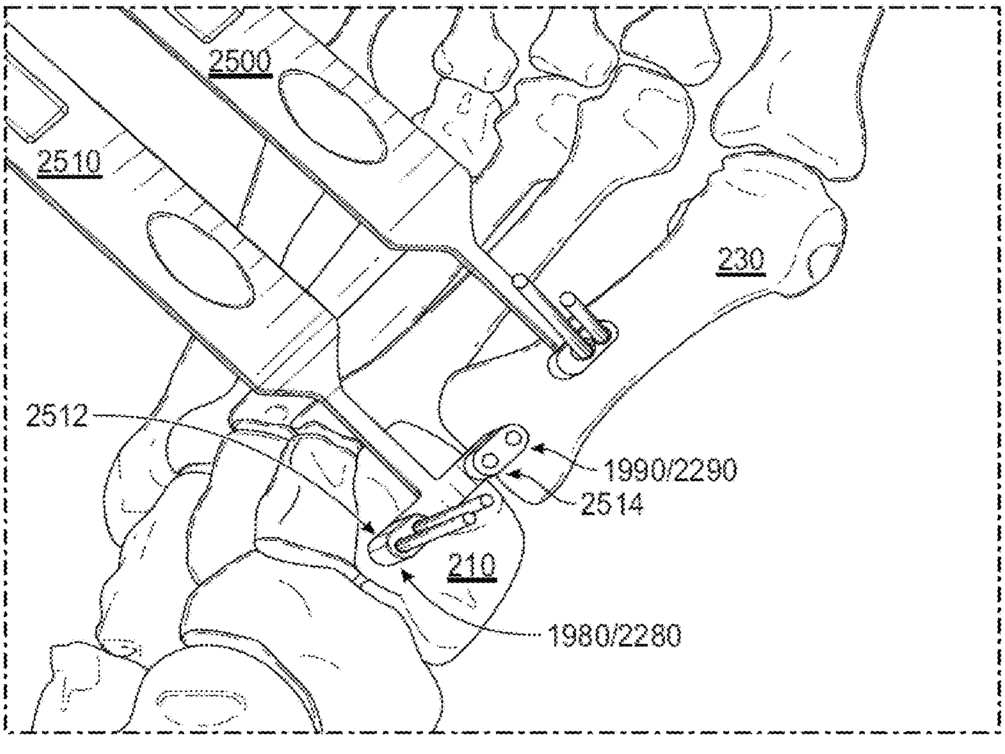
FIG. 25B illustrates a perspective view of the first cuneiform and the first metatarsal of FIG. 25A with the de-rotation handle and first metatarsal rotated.

FIG. 25B illustrates a perspective view of the first cuneiform and the first metatarsal of FIG. 25A with the de-rotation handle and first metatarsal rotated. Once the first metatarsal 230 has been de-rotated a surgeon may connect an alignment handle 2510 to fasteners 1956 of the proximal alignment feature 1980/2280. The alignment handle 2510 may include two proximal alignment holes 2512 and two distal alignment holes 2514. A surgeon may rotate or de-rotate the first metatarsal 230 using the de-rotation handle 2500 until the first metatarsal 230 is in a desired de-rotated/rotated position. Next, a surgeon may slide the proximal alignment holes 2512 over the fasteners 1956 of the proximal alignment feature 1980/2280. The distal alignment holes 2514 may be aligned with the proximal alignment holes 2512. Next, a surgeon may insert a fasteners 1956 (e.g., K-wire) into the distal alignment holes 2514. The fasteners 1956 of the distal alignment holes 2514 may serve as the distal alignment feature 1990/2290. Next, the osteotomy may include a final alignment and compression step.

Figure 26:
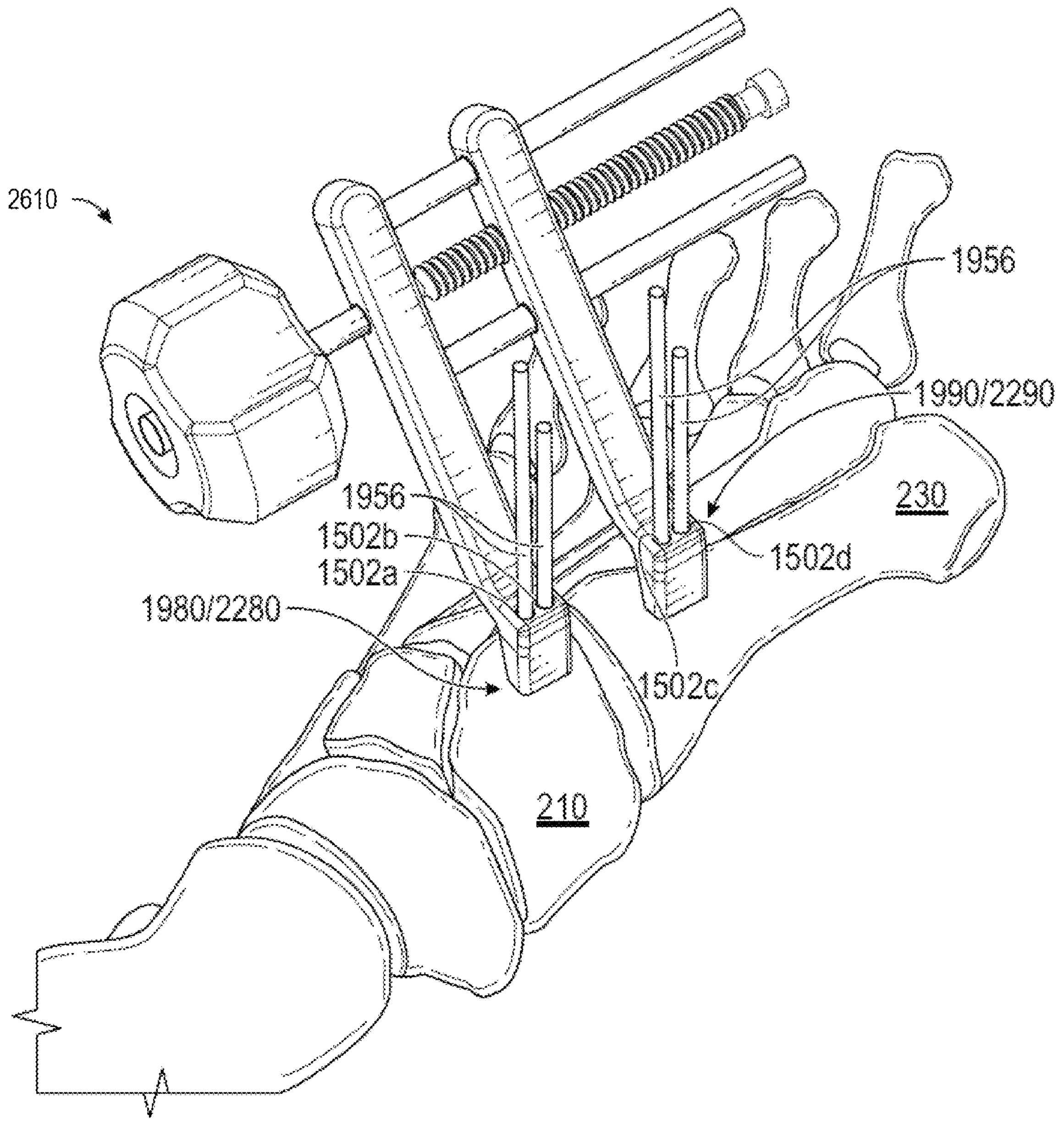
FIG. 26 illustrates a perspective view of the first cuneiform and the first metatarsal of FIGS. 24A, 25A with a compressor/distractor and cross joint guide.

FIG. 26 illustrates a perspective view of the first cuneiform and the first metatarsal of FIGS. 24A, 25A with a compressor/distractor and cross joint guide. In the illustrated embodiment, a surgeon has removed other instruments such that fasteners 1956 of the proximal alignment feature 1980/2280 and fasteners 1956 of the distal alignment feature 1990/2290 remain in the bones. Next, the surgeon may couple an active compression instrument 2610 (which may be similar to the exemplary parallel compressor/distractor 1500 or parallel compressor/distractor 1600) to the fasteners 1956 by sliding the holes 1502*a,b* over the fasteners 1956 of the proximal alignment feature 1980/2280 and the holes 1502*c,d* over the fasteners 1956 of the distal alignment feature 1990/2290. An active compression instrument 2610 refers to any instrument that can compress two or more structures together towards each other or against a stationary object. An "active compression instrument" refers to a mechanical device, apparatus, member, object, body, component, or structure, that is organized, configured, designed, arranged, or engineered to maintain two objects in a compressed state one against the other which may enable a user to perform one or more other operations, method steps, or activities. One example of an active compression instrument is a compressor or an instrument that can function as both a compressor and a distractor. An active compression instrument 2610 may be configured to only provide a compression feature. Alternatively, or in addition, an active compression instrument 2610 may be configured to provide both a compression feature and a distraction feature. The distraction feature is a feature the distracts or separates at least two structures.

According to certain methods, a surgeon may next distract the joint in order to prepare surfaces for fusion. The surgeon may slide holes 1502*a,b* over fasteners 1956 and holes 1502*c,d* over fasteners 1956. The surgeon activates the parallel compressor/distractor 1500 to distract the first metatarsal 230 relative to the first cuneiform 210. Connecting the parallel compressor/distractor 1500 may perform final alignment of the first cuneiform 210 and first metatarsal 230.

Once distracted, the surgeon may remove intruding soft tissue and may fenestrate and/or abrade the cut surfaces of the two bones to encourage fusion and/or osteointegration.

Next, the surgeon may use the parallel compressor/distractor 1500 to compress the two bones together at the newly formed cut surfaces. This causes a desired rotation and translation of the first metatarsal 230 relative to the first cuneiform 210. This forces the cut surfaces (or faces) of the two bones to become parallel. Advantageously, the cut surfaces of the two bones can be forced to become parallel because the position, orientation, and angles of the fasteners 1956 of either, or both, of the proximal alignment feature 1980/2280 and distal alignment feature 1990/2290 can be predefined and customized for each patient when the cutting guide 1900/2200 is fabricated. This alignment enables parallel compression of the two bones together using the parallel compressor/distractor 1500 to provide active compression. Parallel active compression enables more effective compression of the two bones together. The parallel compressor/distractor 1500 is activated such that the first cuneiform 210 and the first metatarsal 230 are pressed together against each other.

Figure 27:
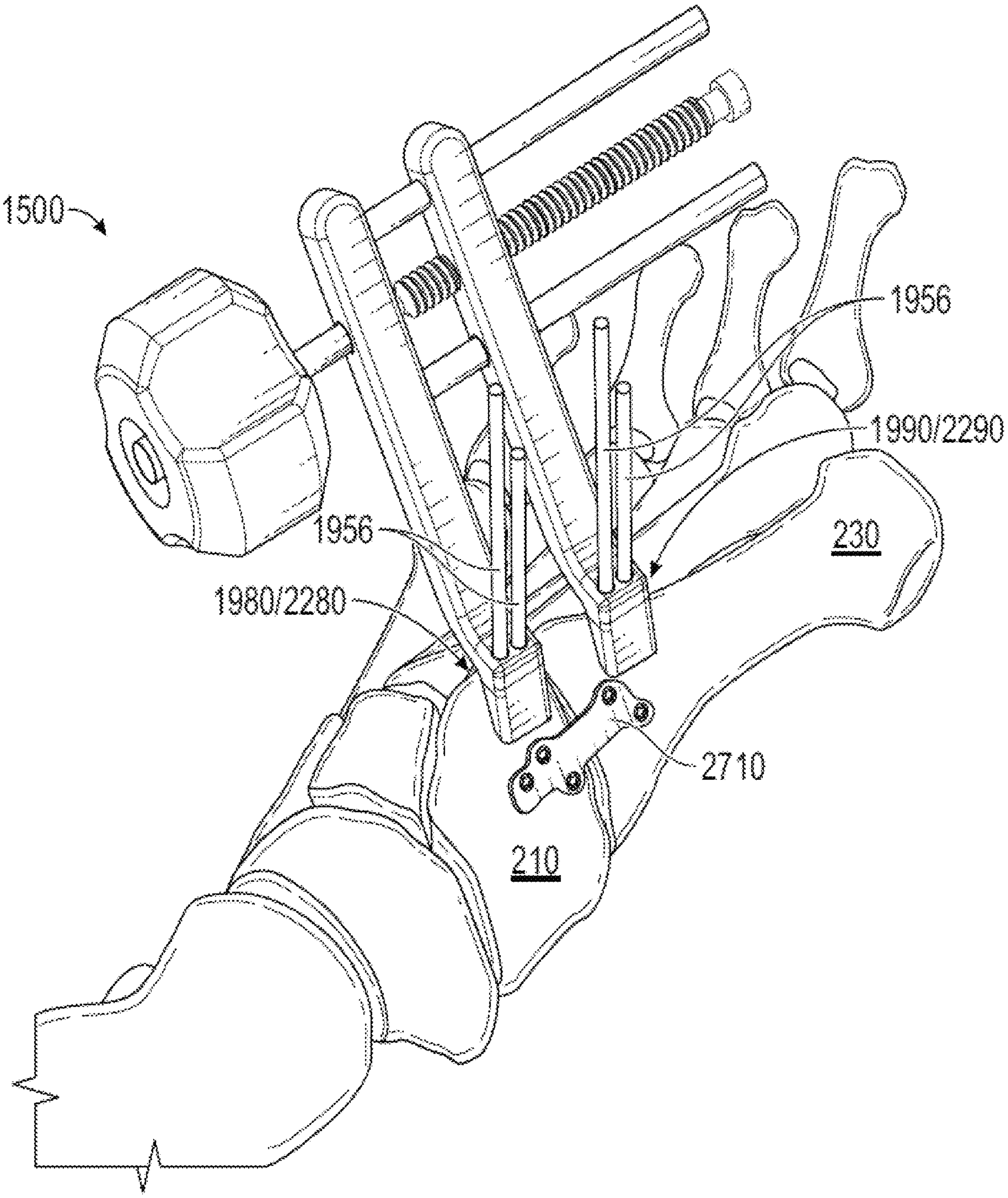
FIG. 27 illustrates a perspective view of the first cuneiform and the first metatarsal of FIGS. 24A, 25A with a compressor/distractor and fastener(s).

Next, various forms of fixation may be used to complete the fusion of the two bones. FIG. 27 illustrates a perspective view of the first cuneiform and the first metatarsal of FIGS. 24A, 25A with a parallel compressor/distractor 1500 and fastener(s). In one embodiment, a surgeon may slide the cross joint guide 1604 over the fasteners 1956 of the distal alignment feature 1990/2290 and use the holes 1608 to deploy fasteners such as K-wires or bone screws across the joint to respectively, temporarily or permanently fuse the joint.

Alternatively, or in addition, the surgeon may leave the parallel compressor/distractor 1500 connected and actively applying a compressive force to press the bones together while another kind of fastener 2710, such as a bone plate. The fastener 2710 may be deployed with one or more bone screws into the bones to connect the first metatarsal 230 to the first cuneiform 210. Advantageously, the fastener 2710 can be deployed which the bones are under active compression. This can promote osteointegration and fusion of the bones to close the joint. With the fastener 2710 deployed a surgeon may release, and remove, the parallel compressor/distractor 1500. This may complete the osteotomy procedure with the remains steps being closing the incision(s) and preparing the patient for recovery.

Figure 28:
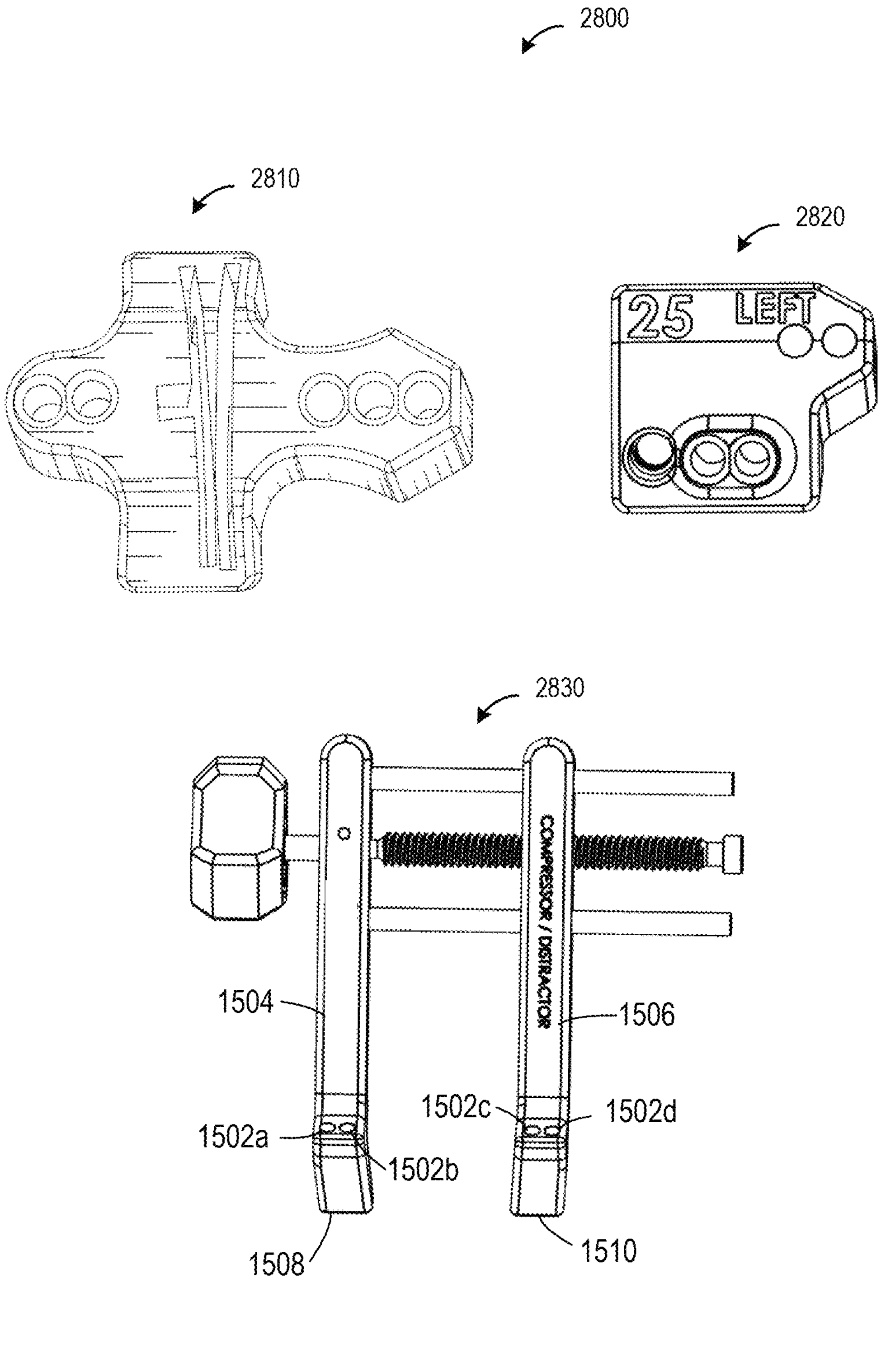
FIG. 28 illustrates a perspective view of an exemplary system for correcting a condition in accordance with one embodiment.

FIG. 28 illustrates a perspective view of an exemplary system 2800 for correcting a condition in accordance with one embodiment. The system 2800 includes a cut guide 2810, a first metatarsal alignment feature 2820, and a compressor/distractor 2830.

In certain embodiments, the cut guide 2810 may be a patient specific instrument, a patient specific cut guide. In certain embodiments, the cut guide 2810 is fabricated for a particular joint, of a particular patient, and/or to address a particular condition. Various example cut guides such as cut guide 300, cut guide 700, cut guide 1043, cut guide 1200, cutting guide 1900, cut guide 2200, or the like may serve as the cut guide 2810 of the system 2800. The cut guide 2810 may include a first guide feature configured to define a first cut surface configured for resection of a first metatarsal of a patient. First slot 1960 and/or first slot 2260 may serve as one example of the first guide feature. The cut guide 2810 may include a second guide feature configured to define a second cut surface configured for resection of a medial cuneiform of a patient. Second slot 1970 and/or second slot 2270 may serve as one example of the second guide feature. The cut guide 2810 may include an inferior side comprising a bone engagement surface shaped to match a first surface of the first metatarsal and a second surface of the medial cuneiform. Inferior side 1922 and/or bone engagement surface 1924 or inferior side 2222 and/or bone engagement surface 2224 may serve as one example of the inferior side and bone engagement surface. In one embodiment, the cut guide 2810 may include a medial cuneiform alignment feature coupled to the medial cuneiform. The proximal alignment feature 1980 and/or the proximal alignment feature 2280 may serve as the medial cuneiform alignment feature. The first guide feature and/or the second guide feature of the cut guide 2810 may be configured based on patient imaging data such that fusion of the first metatarsal at the first cut surface to the medial cuneiform at the second cut surface mitigates the condition. In certain embodiments, the cut guide 2810 is fabricated for single use with a single patient and on a left or a right extremity of the patient.

The first metatarsal alignment feature 2820 may take the form of various devices. In one embodiment, the first metatarsal alignment feature 2820 may include the distal alignment feature 1990 and/or the distal alignment feature 2290 of a pin guide 2400 or one or more fasteners 1956 placed by a surgeon or placed using one or more of a de-rotation handle 2500 and/or alignment handle 2510. The pin guide 2400 may position a plurality of alignment pins such that the first metatarsal 230 can be rotated to align the pins and rotate the first metatarsal 230 through a desired rotation angle about the first metatarsal 230 longitudinal axis.

The system 2800 may include a plurality of pin guides 2400 each of a different size, such as different degrees of offset angle (angle C), different sizes based on gender, and different sizes or configurations based on which extremity is involved. Advantageously, the first metatarsal alignment feature 2820 may be independent of the cut guide 2810. The independence provides flexibility relating to de-rotation of the first metatarsal.

The compressor/distractor 2830 may include the parallel compressor/distractor 1500 and/or the parallel compressor/distractor 1600. The compressor/distractor 2830 can engage the medial cuneiform alignment feature and the first metatarsal alignment feature and compress a first cut surface of the first metatarsal against a second cut surface of the medial cuneiform. The medial cuneiform alignment feature and the first metatarsal alignment feature may be substantially aligned prior to connecting the compressor/distractor 2830. Connecting the compressor/distractor 2830 may provide final alignment of the medial cuneiform alignment feature and the first metatarsal alignment feature. In certain embodiments, the medial cuneiform alignment feature and the first metatarsal alignment feature may not be aligned with each other. Instead, legs of the compressor/distractor 2830 may be configured to engage the unaligned medial cuneiform alignment feature and first metatarsal alignment feature. The compressor/distractor 2830 may also include a compression feature but not a distractor feature. In certain embodiments, different sizes of compressor/distractor 2830 may be included to different sizes of patients.

In certain embodiments, the compressor/distractor 2830 includes legs that are closer to each other at distal end of each leg than at a proximal end of each leg. The legs 1504/1506 and toes 1508/1510 of the compressor/distractor 1500/2830 are one example of such an embodiment. Advantageously, the cut guide 2810 can be customized for a specific patient. In certain embodiments, this means that the position and orientation of one or more of the first guide feature, second guide feature, bone engagement surface, first bone attachment feature, second bone attachment feature, first alignment feature, and/or second alignment feature, can be determined based on patient imaging data and can be engineered and fabricated to address a specific condition for a particular patient. For example, the position and orientation of one or more of the first guide feature, second guide feature may be such that a planter edge of a first cut surface of a first metatarsal 230 contacts a corresponding planter edge of a second cut surface of a first metatarsal 230 as the two cut surfaces are brought together to fuse the joint. The compressor/distractor 1500/2830 may translate and/or rotate one or the other or both of the first metatarsal 230 and first cuneiform 210 such that the two cut surfaces. In this manner, the cut guide 2810 and/or the system 2800 avoids a plantar gap between the two bones. Avoiding a plantar gap can be a factor in a successful fusion that also avoids non-union.

Figure 29:
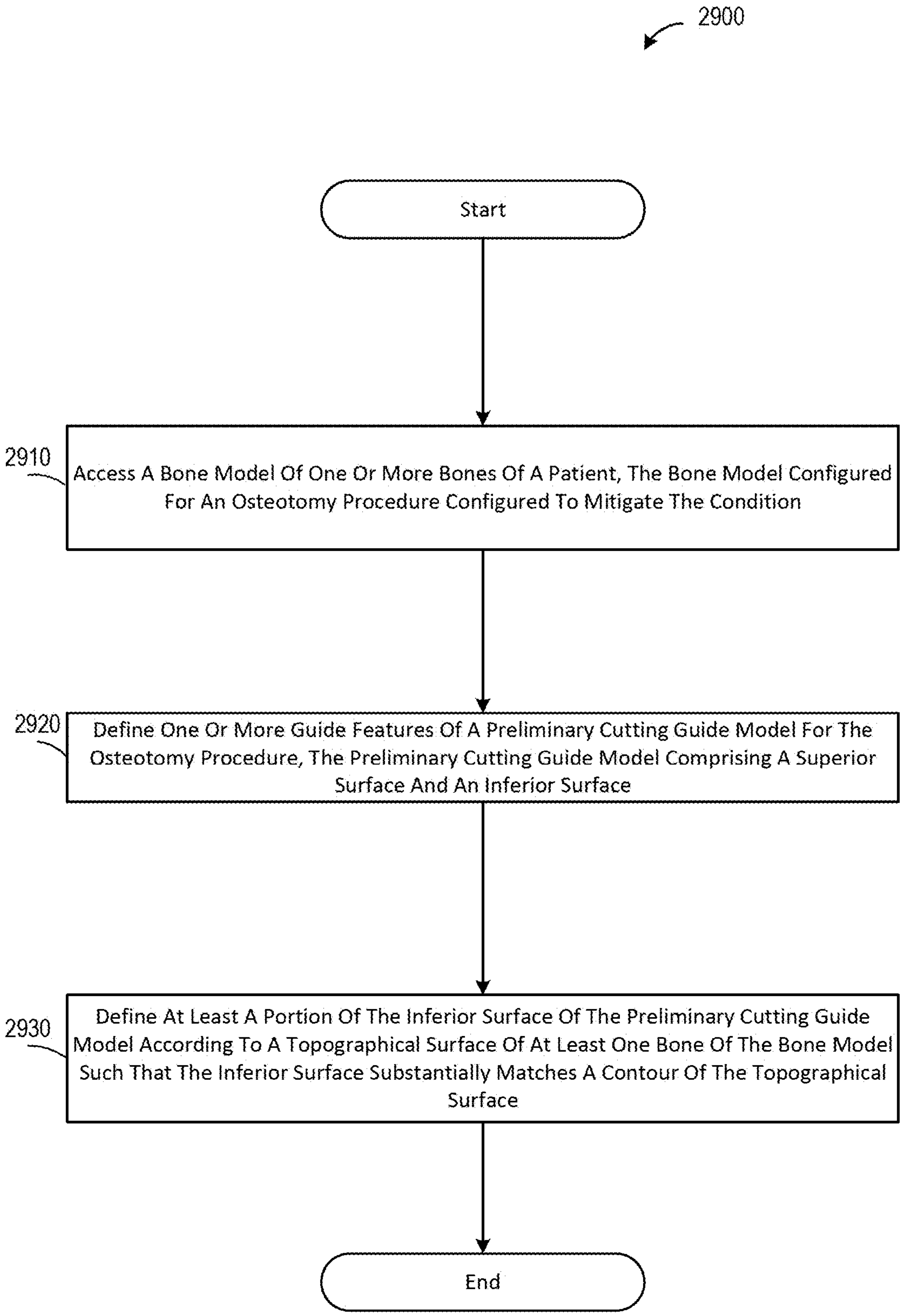
FIG. 29 is a flow chart diagram of one example method for making a patient specific cutting guide according to one embodiment.

FIG. 29 is a flow chart diagram of one example method 2900 for making a patient specific cutting guide according to one embodiment. Prior to steps of the method 2900, a bone model (also referred to as CAD model above) or one or more bones of a patient is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve or be a part of anatomic data for a patient.

A bone model or anatomic model of a patient's body or body part(s) may be generated by computing devices that analyze medical imaging images. Structures of a patient's body can be determined using a process called segmentation. In certain embodiments, the patient imaging data maybe gathered from the patient as the patient is not placing their weight on one or more feet. Alternatively, or in addition, in certain embodiments, the patient imaging data maybe gathered from the patient as the patient is placing their weight on one or more feet. Such imaging may be referred to as weight-bearing patient imaging data. For example in one embodiment, the bone model is derived from patient imaging data generated while the patient placed their weight on at least one joint involved in the osteotomy procedure.

Generally, an osteotomy procedure is not done while a patient places their weight on one or more feet involved in the procedure. Thus, a surgeon can not intraoperatively determine how much correction of bone positioning and/or rotation may be desired to correct a condition such as a hallux valgus. However, because the present disclosure can be used to generate patient specific instrumentation from weight-bearing patient imaging data, the present disclosure can provide instruments such as cut guide, pin guide, bone engagement surface 1924/2224, parallel compressor/distractor, or the like that account for positions and configurations of the patient's bones while bearing the weight of the patient. Advantageously, using weight-bearing patient imaging data can provide for more successful procedures and more long term and lasting correction of conditions for the patient.

In one embodiment, the method 2900 begins after a bone model of a patient's body or body part(s) is generated. In a first step 2910, bone model of one or more bones of a patient based on the condition and/or the bone model is accessed. Next, the method 2900 defines 2920 one or more guide features of a preliminary cutting guide model for an osteotomy procedure, the preliminary cutting guide model comprising a superior surface and an inferior surface. Next, the method 2900 proceeds by defining 2930 at least a portion of the inferior surface of the preliminary cutting guide model according to a topographical surface of at least one bone of the bone model such that the inferior surface substantially matches a contour of the topographical surface. In certain embodiments, the method 2900 may also include a step of defining one or more alignment features of the preliminary cutting guide model for the osteotomy procedure. After step 2930, the preliminary cutting guide model is configured for fabrication of a patient specific cutting guide corresponding to the preliminary cutting guide model. After step 2930, the method 2900 may end.

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

In one aspect, the preliminary cutting guide may be used, as-is, without any further changes, modifications, or adjustments and thus become a patient specific cutting guide. In another aspect, the preliminary cutting guide may be modified, adjusted, or configured to more specifically address the goals, objectives, or needs of a patient or a surgeon and by way of the modifications become a patient specific cutting guide.

The patient specific cutting guide can be used by a user, such as a surgeon, to guide making one or more resections of a structure, such as a bone for a procedure. Accordingly, a preliminary cutting guide model can be used to generate a patient specific cutting guide model. The patient specific cutting guide model may be used in a surgical procedure to address, correct, or mitigate effects of the identified deformity and may be used to generate a patient specific cutting guide that can be used in a surgical procedure for the patient.

Figure 30A:
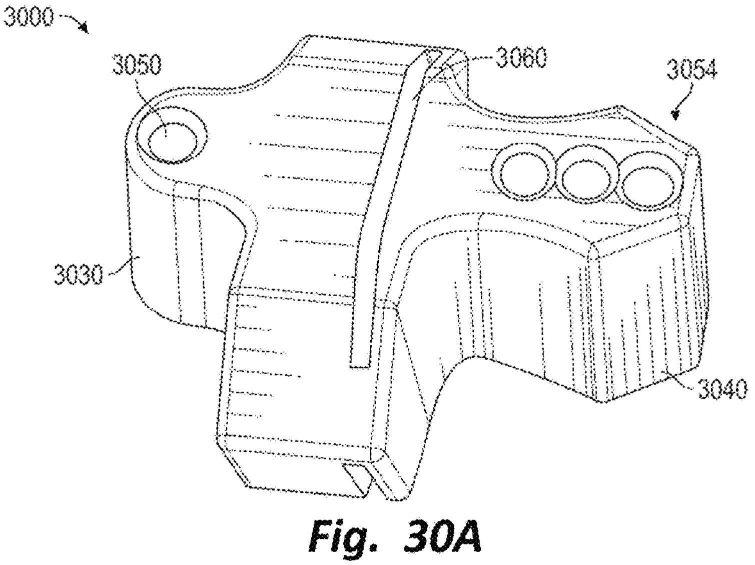
FIGS. 30A-30C illustrates perspective views of an exemplary preliminary cutting guide model modified in accordance with one embodiment for use as a patient-specific cutting guide.
Figure 30B:
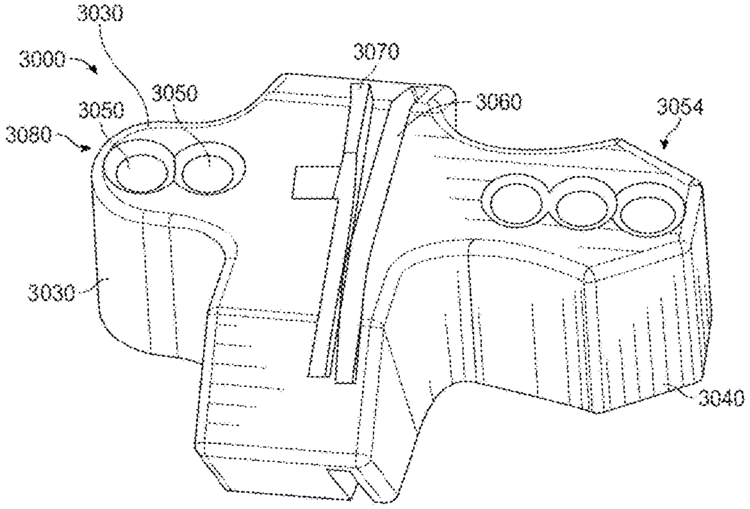
Figure 30C:
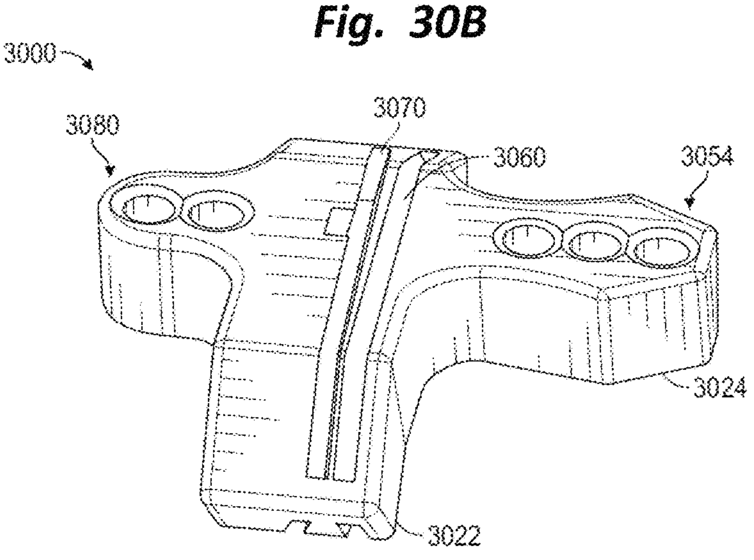

FIGS. 30A-30C illustrates perspective views of an exemplary preliminary cutting guide model modified in accordance with one embodiment for use as a patient-specific cutting guide. In certain embodiments, steps of the method 2900 may include additional steps that add to or expand upon steps of the method 2900.

For example, accessing 2910 a bone model of one or more bones of a patient based on the condition and/or the bone model may include additional steps. For example, the bone model may include a first modeled bone (not shown in FIG. 30A) and a second modeled bone (not shown in FIG. 30A) of a joint of the patient and the bone model may be modified such that the first modeled bone (e.g., a first metatarsal 230) is rotated about a longitudinal axis of the first modeled bone from a first position to a second position. FIG. 30A illustrates one example of a preliminary cutting guide model 3000.

Next, a first cut surface in the first modeled bone is defined that is perpendicular to the longitudinal axis of the first modeled bone. The first cut surface may be defined using a first guide feature 3060 and may be predefined in a preliminary cutting guide model 3000. In certain embodiments, the first cut surface may be formed during the procedure on a patient's bone by a surgeon cutting using a first guide feature 3060. The first guide feature 3060 may be defined in the preliminary cutting guide model 3000 such that cutting using the first guide feature 3060 will form the first cut surface. The first guide feature 3060 may include a slot formed in the preliminary cutting guide model 3000 that is configured to guide formation of the first cut surface.

In one embodiment, the preliminary cutting guide model 3000 may originally include a predefined first guide feature 3060 that is aligned perpendicular to two or more holes 3050 of a distal bone attachment feature 3054. It should be noted that the preliminary cutting guide model 3000 of FIG. 30A does not include a second guide feature and/or a second hole 3050 because the orientation and position of the second guide feature and/or a second hole 3050 has not yet been determined or defined. In certain embodiments, the preliminary cutting guide model 3000 may be selected from a repository of template cutting guide models. Each template cutting guide model may be configured for an osteotomy procedure configured to correct one of a plurality of conditions.

Next, as part of accessing 2910 a bone model, a first angle for a second cut surface of the second modeled bone may be defined. The first angle may be measured relative to the first cut surface and may extend inferiorly away from the first cut surface. FIG. 19D illustrates one example of the first angle by way of angle A. Next, a second angle for the second cut surface of the second modeled bone may be defined. The second angle may be measured relative to the first cut surface and configured to mitigate the condition. FIG. 19H illustrates one example of the first angle by way of angle B.

Next, as part of accessing 2910 a bone model, the bone model of the first modeled bone may be modified to include the first cut surface and the second modeled bone may be modified to include the second cut surface. In addition, one or more guide members of the preliminary cutting guide model 3000 are configured and positioned to enable a surgeon to form the first cut surface and the second cut surface.

Accordingly, referring to FIG. 30B, a second guide feature 3070 in the form of a second slot may be defined in the preliminary cutting guide model 3000 and configured to guide formation of a second cut surface of a second bone of the patient corresponding to the second modeled bone. The first guide feature 3060 and second guide feature 3070 are positioned in the preliminary cutting guide model 3000 such that fixing the first cut surface of the first bone to the second cut surface of the second bone mitigates the condition. Note that the preliminary cutting guide model 3000 includes both the first guide feature 3060 and the second guide feature 3070. In the illustrated embodiment, the second guide feature 3070 is oriented and positioned for formation of the second cut surface. In addition, a second hole 3050 is defined in the proximal arm 3030. The second hole 3050 aligns with a first hole 3050 of the proximal alignment feature 3080 in addition the holes of the proximal alignment feature 3080 are perpendicular to the second guide feature 3070.

In the illustrated embodiment, of FIGS. 30A, 30B, an inferior side, also referred to as the bone engagement surface of the preliminary cutting guide model 3000 has a squared and boxy configuration because the inferior side for the preliminary cutting guide model 3000 has not yet been defined. FIG. 30C illustrates an inferior side 3022, or bone engagement surface 3024 that has been defined to match the contour of bones of the patient based on patient imaging data. The modified preliminary cutting guide model 3000 of FIG. 30C is ready to be manufactured, for example, using additive manufacturing.

Figure 31:
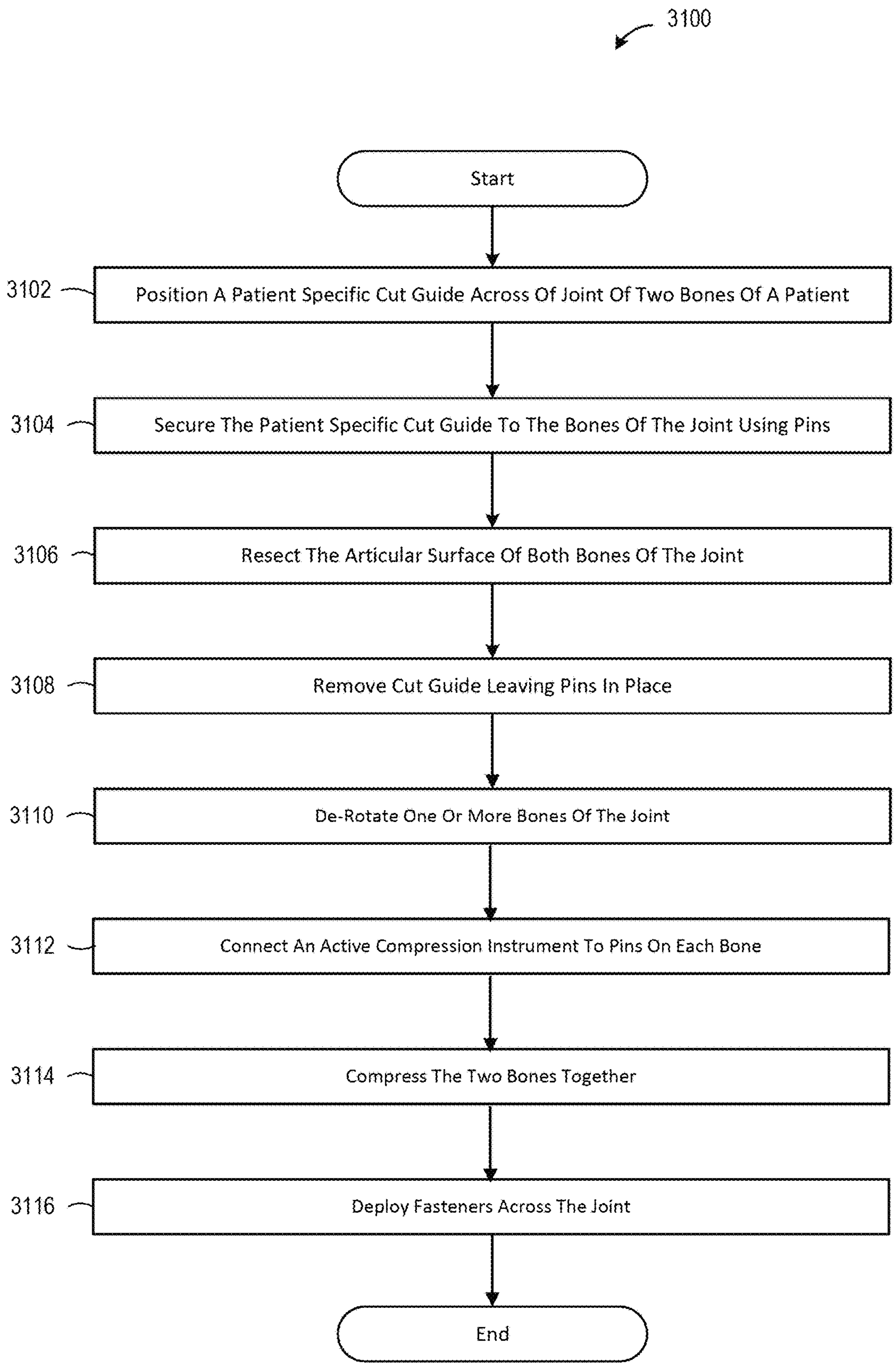
FIG. 31 is a flow chart diagram of one example method for using a patient specific cutting guide according to one embodiment to mitigate a condition present in a patient.

FIG. 31 is a flow chart diagram of one example method 3100 for using a patient specific cutting guide according to one embodiment to mitigate a condition present in a patient. Before the method 3100 begins a surgeon may obtain a patient specific cut guide and/or one or more other instruments that may be patient specific or may be configured for use with most patients.

The method begins and the surgeon positions 3102 a patient specific cut guide across of joint of two bones of a patient. Next, the surgeon may secure 3104 the patient specific cut guide to the bones of the joint using pins (e.g., K-wires). Next, the surgeon may resect 3106 the articular surface of both bones of the joint. Next, the surgeon may remove 3108 the patient specific cut guide while leaving one or more pins in place on the bones. Pins left in place may include pins that are part of the proximal bone attachment feature 2252 and/or the distal bone attachment feature 2254. Next, the surgeon may de-rotate 3110 one or more bones of the joint. Next, the surgeon may connect 3112 an active compression instrument to pins on each bone of the joint. Next, the surgeon may compress 3114 the two bones of the joint together. Next, the surgeon may deploy 3116 fasteners across the joint. The fasteners may be temporary fasteners such as K-wires or bone screws or permanent fasteners such as a bone plate and bone screws.

Those of skill in the art will appreciate that method 3100 is one of many that may be used to address a condition of the patient using the apparatuses, devices, methods, features, and aspects of the present disclosure.

Figure 32:
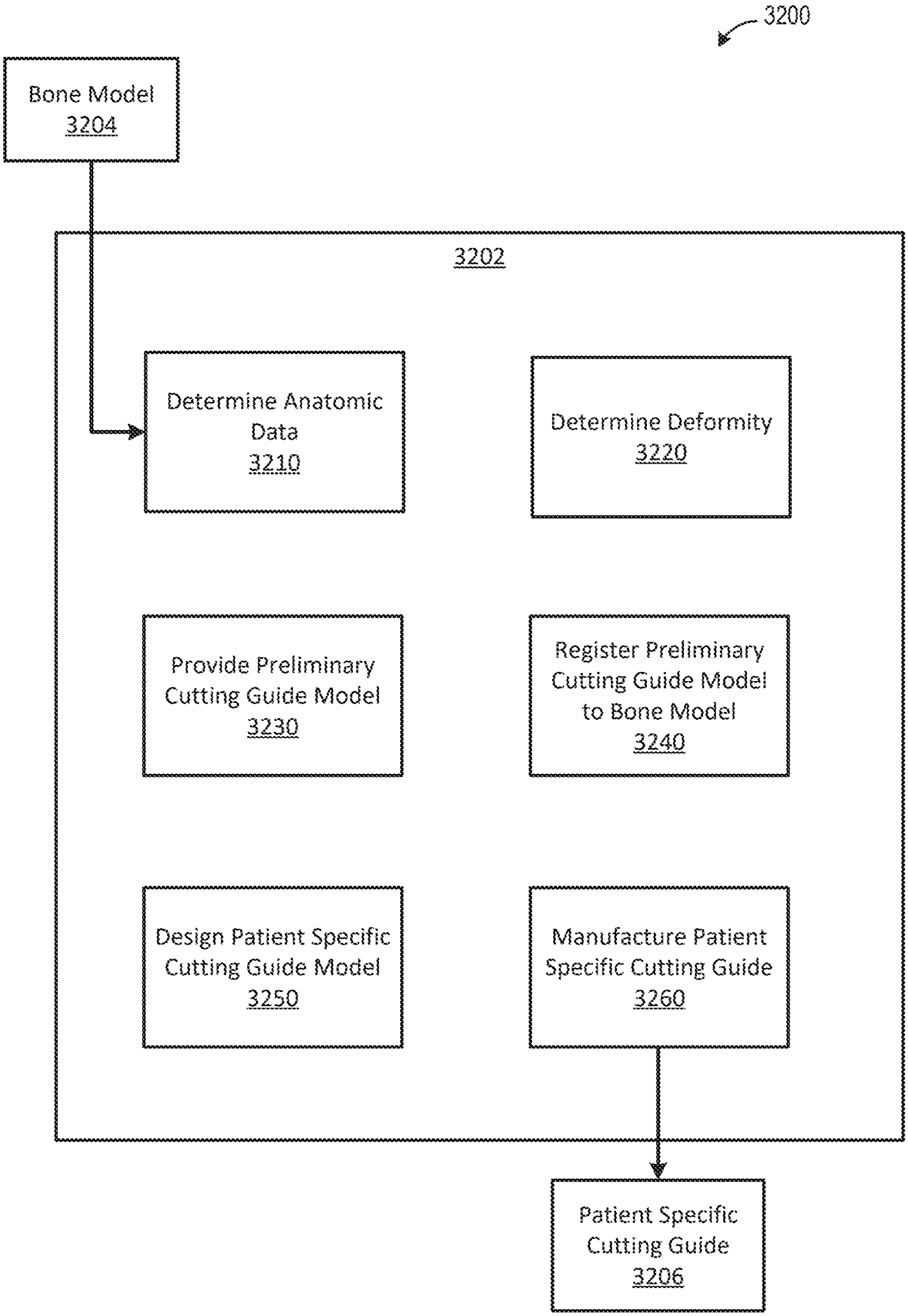
FIG. 32 illustrates an exemplary system configured to generate one or more patient specific instruments configured to correct a bone condition, according to one embodiment.

FIG. 32 illustrates an exemplary system 3200 configured to generate one or more patient specific instruments configured to correct a bone condition, according to one embodiment. The system 3200 may include an apparatus 3202 configured to accept, review, receive or reference a bone model 3204 and provide a patient specific cutting guide 3206. In one embodiment, the apparatus 3202 is a computing device. In another embodiment, the apparatus 3202 may be a combination of computing devices and/or software components or a single software component such as a software application.

The apparatus 3202 may include a determination module 3210, a deformity module 3220, a provision module 3230, a registration module 3240, a design module 3250, and a manufacturing module 3260. Each of which may be implemented in one or more of software, hardware, or a combination of hardware and software.

The determination module 3210 determines anatomic data 3212 from a bone model 3204. In certain embodiments, the system 3200 may not include a determination module 3210 if the anatomic data is available directly from the bone model 3204. In certain embodiments, the anatomic data for a bone model 3204 may include data that identifies each anatomic structure within the bone model 3204 and attributes about the anatomic structure. For example, the anatomic data may include measurements of the length, width, height, and density of each bone in the bone model. Furthermore, the anatomic data may include position information that identifies where each structure, such as a bone is in the bone model 3204 relative to other structures, including bones. The anatomic data may be in any suitable format and may be stored separately or together with data that defines the bone model 3204.

In one embodiment, the determination module 3210 may use advanced computer analysis such as image segmentation to determine the anatomic data. Alternatively, or in addition the determination module 3210 may use software and/or systems that implement one or more artificial intelligence methods (e.g., machine learning and/or neural networks) for deriving, determining, or extrapolating, anatomic data from the bone model. In one embodiment, the determination module 3210 may perform an anatomic mapping of the bone model 3204 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

The deformity module 3220 determines or identifies one or more deformities or other anomalies based on the anatomic data 3212. The deformity may include a deformity between two bones of a patient's foot as represented in the bone model 3204. In one embodiment, the deformity module 3220 may compare the anatomic data 3212 to a general model that is representative of most patient's anatomies and that does not have a deformity or anomaly. In one embodiment, if the anatomic data 3212 does not match the general model a deformity is determined. Various deformities may be detected including those that have well-known names for the condition and those that are unnamed.

The provision module 3230 is configured to provide a preliminary cutting guide model 3238. The provision module 3230 may use a variety of methods to provide the preliminary cutting guide model 3238. In one embodiment, the provision module 3230 may generate preliminary cutting guide model 3238. In the same or an alternative embodiment, the provision module 3230 may select a template cutting guide model 3236 for an osteotomy procedure configured to correct the deformity identified by the deformity module 3220. In one embodiment, the provision module 3230 may select a template cutting guide model 3236 from a set of template cutting guide models 3236 (e.g., a library, set, or repository of template cutting guide models 3236).

The registration module 3240 registers the preliminary cutting guide model 3238 with one or more bones or other anatomical structures of the bone model 3204. As explained above, registration is a process of combining medical imaging data, patient imaging data, and/or one or more models such that the preliminary cutting guide model 3238 can be used with the bone model 3204.

The design module 3250 designs a patient specific cutting guide (or patient specific cutting guide model) based on the preliminary cutting guide model. The design operation of the design module 3250 may be completely automated, partially automated, or completely manual. A user may control how automated or manual the designing of the patient specific cutting guide (or patient specific cutting guide model) is.

The manufacturing module 3260 may manufacture a patient specific cutting guide 3206 using the preliminary cutting guide model 3238. The manufacturing module 3260 may use a patient specific cutting guide model generated from the preliminary cutting guide model 3238. The manufacturing module 3260 may provide the patient specific cutting guide model to one or more manufacturing tools and/or fabrication tool. The patient specific cutting guide model may be sent to the tools in any format such as an STL file or any other CAD modeling or CAM file or method for data exchange. In one embodiment, a user can adjust default parameters for the patient specific cutting guide such as types and/or thicknesses of materials, dimensions, and the like before the manufacturing module 3260 provides the patient specific cutting guide model to a manufacturing tool.

Figure 33:
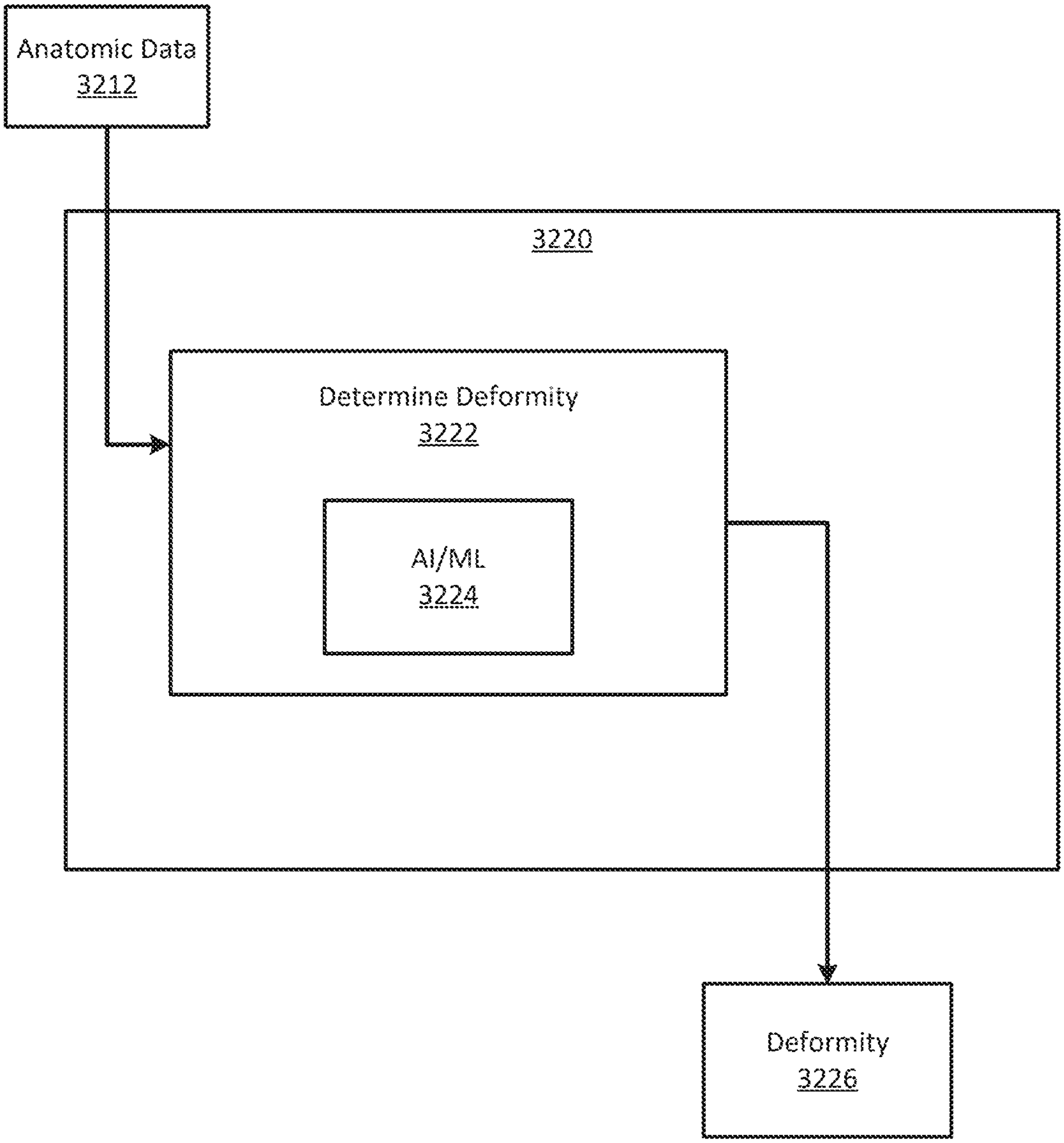
FIG. 33 illustrates an exemplary apparatus configured to determine a deformity, according to one embodiment.

FIG. 33 illustrates an exemplary deformity module 3220 configured to determine a deformity, according to one embodiment. The deformity module 3220 may detect one or more deformities and/or anomalies of a patient's anatomy by analyzing anatomic data 3212 and other inputs, such as a certain type or class of deformities to search for.

The deformity module 3220 may be completely automated, partially automated, or completely manual. A user may control how automated or manual the detection of the deformity is. The user may provide instructions to the deformity module 3220 to facilitate automatic or partially automated detection or determination of one or more deformities.

The deformity module 3220 may include a deformity detection module 3222. The deformity detection module 3222 may be configured for automated determination of a deformity. For example, in one embodiment, the deformity detection module 3222 includes an artificial intelligence or machine learning module 3224. The artificial intelligence or machine learning module 3224 is configured to implement one or more of a variety of artificial intelligence modules that may be trained for detecting an anomaly or deformity based on anatomic data 3212. In another embodiment, the deformity module 3220 may receive patient imaging data, a bone model, a CAD model or the like and use these inputs to determine deformities in the bones of a patient.

In one embodiment, the artificial intelligence or machine learning module 3224 may be trained using a large data set of anatomic data 3212 for healthy non-deformed bones and a large data set of anatomic data 3212 for deformed bones in which the deformity has been previously identified and labeled in the dataset. The artificial intelligence or machine learning module 3224 may implement, or use, a neural network configured according to the training such that as the artificial intelligence or machine learning module 3224 accepts the anatomic data 3212 for a particular patient, the artificial intelligence or machine learning module 3224 is able to determine what deformity 3226 exists in the patient's bones, when such a deformity 3226 exists.

Figure 34A:
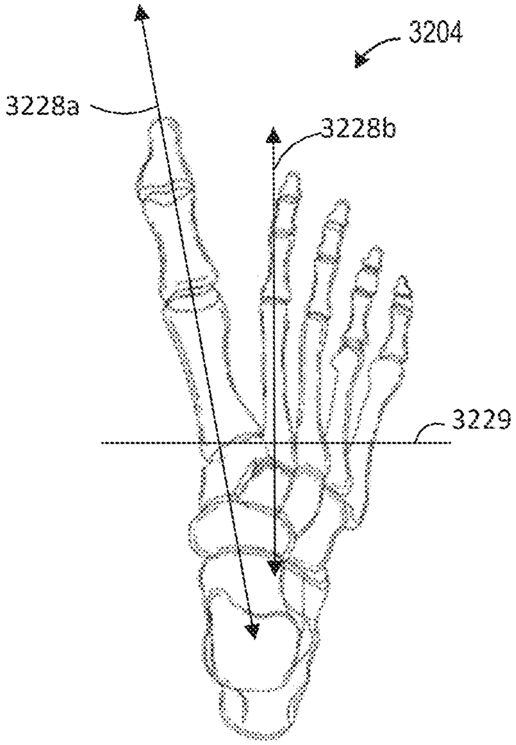
FIGS. 34A and 34B illustrates one example of a method for determining a deformity and a correction for the deformity, according to one embodiment.
Figure 34B:
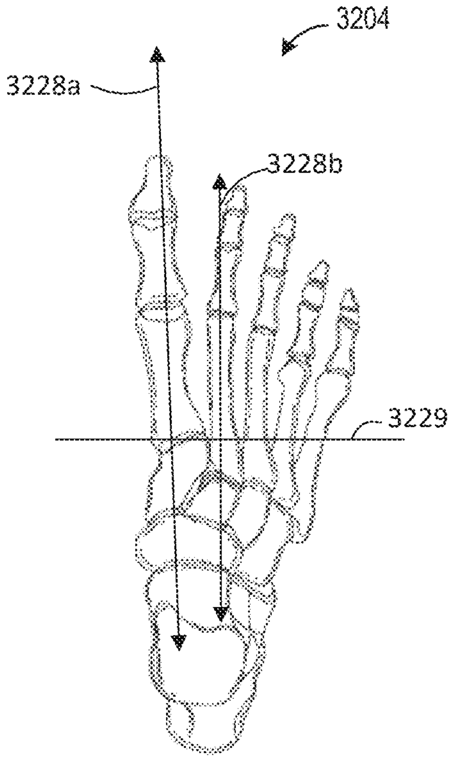

FIGS. 34A and 34B illustrates one example of a method for determining a deformity and a correction for the deformity, according to one embodiment. The deformity module 3220 may use a particular method for determining whether or not two or more bones have a deformity 3226. The deformity module 3220 may use one or more advanced computing techniques for determining the deformity 3226.

Referring now to FIG. 34A, in one embodiment, the deformity module 3220 starts by identifying a center longitudinal axis 3228*a*, 3228*b* (FIG. 34A shows two of the plurality of axes for clarity) for each bone in the bone model 3204. For example, the deformity module 3220 may identify the center longitudinal axis 3228*a* for a first metatarsal and the center longitudinal axis 3228*b* for the second metatarsal.

Next, the deformity module 3220 may identify a reference axis 3229 perpendicular with one of the center longitudinal axes 3228*a,b*, such as center longitudinal axis 3228*b*. The reference axis 3229 may be at or near a joint between bones of the bone model 3204. The deformity module 3220 may determine that a deformity 3226 exists if the center longitudinal axes 3228*a,b* are not parallel or are not parallel when measured with a predefined margin for error. FIG. 34A illustrates a bone model 3204 with a deformity 3226. The deformity 3226 is that the first metatarsal is not parallel or not sufficiently parallel to the second metatarsal at the joint between the first metatarsal and the medial cuneiform bones. Once the deformity 3226 is determined, the deformity module 3220 or apparatus 3202 may determine what steps, procedures, or instrumentation can be used to correct the deformity 3226. The deformity module 3220 may use a name, label, tag, or other identifier for a particular deformity 3226.

FIG. 34B illustrates the bone model 3204 of FIG. 34A after a corrective procedure and/or application of corrective implants may be performed. The center longitudinal axes 3228_a,b_ are parallel, or sufficiently parallel, such that the deformity 3226 is not a problem for a patient.

Figure 35:
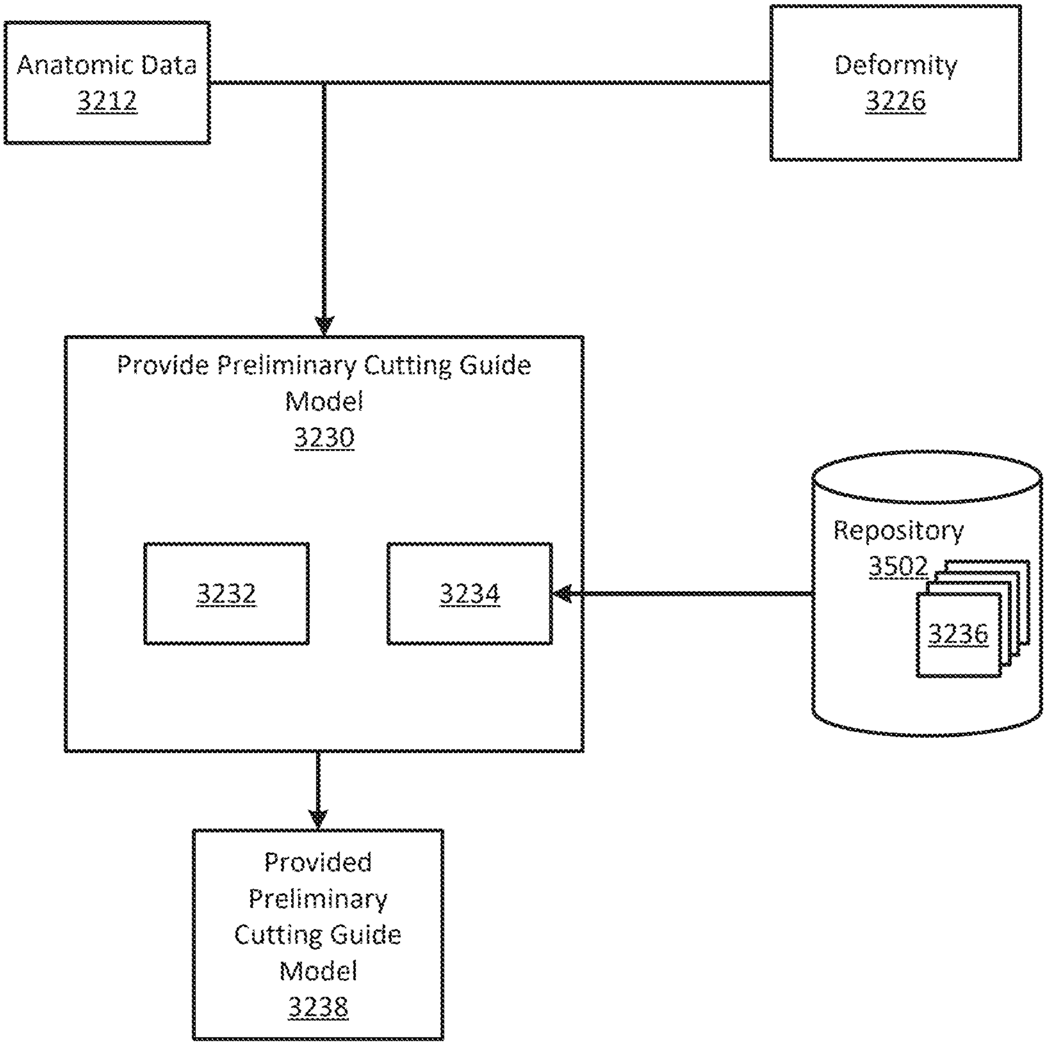
FIG. 35 illustrates an exemplary selection module configured to provide a preliminary cutting guide model, according to one embodiment.

FIG. 35 illustrates an exemplary provision module 3230 configured to provide a preliminary cutting guide model, according to one embodiment. The provision module 3230 may accept anatomic data 3212 and a designation, identifier, label, or name of a deformity 3226. In the illustrated embodiment, the provision module 3230 may generate a preliminary cutting guide model 3238 (e.g., generate from 'scratch') or the provision module 3230 may select a template cutting guide model 3236 automatically from a set of template cutting guide models 3236 stored in a repository 3502. The provision module 3230 may incorporate a variety of parameters in order to provision, generate, determine, or select a template cutting guide model 3236. For example, in addition to the anatomic data 3212, the provision module 3230 may include patient imaging data, deformity parameters for a variety of angular deformities (in all 3 planes) of the midfoot or hind foot and ankle where an osteotomy could be used, patient preferences, and/or surgeon input parameters.

In one embodiment, the provision module 3230 may include a generator 3232 and/or a selection module 3234. In one embodiment, the generator 3232 is configured to generate a preliminary cutting guide model 3238. In certain embodiments, the generator 3232 may generate or create the preliminary cutting guide model based on anatomic data and/or a bone model or a combination of these and no other inputs. (e.g. no model or predesigned structure, template, or prototype). Alternatively, or in addition, the generator 3232 may generate or create the preliminary cutting guide model using a standard set of features or components that can be combined to form the preliminary cutting guide model. The generated preliminary cutting guide model may subsequently be modified or revised by an automated process, and/or manual process, to generate the preliminary cutting guide model used in this disclosure.

The selection module 3234 may be configured to select a template cutting guide model 3236 for an osteotomy procedure configured to correct the deformity identified by the deformity module 3220. In one embodiment, the provision module 3230 may select a template cutting guide model 3236 from a set of template cutting guide models 3236 (e.g., a library, set, or repository of template cutting guide models 3236). In one embodiment, the template cutting guide model 3236 may include digital models. In another embodiment, the template cutting guide model 3236 may include physical models. In such an embodiment, the repository 3502 may be a warehouse or other inventory repository. Where the template cutting guide model 3236 are physical models, the systems, modules, and methods of this disclosure can be used and the physical model may be milled or machined (e.g., a CNC machine) to form a patient specific cutting guide that conforms to the bone surfaces of the patient.

Selection of a suitable template cutting guide model 3236 may be completely automated and/or may be partially automated and/or may depend on confirmation from a user before a generated preliminary cutting guide model or a proposed template cutting guide model 3236 becomes the preliminary cutting guide model 3238. In another embodiment, the selection module 3234 may facilitate a manual selection by a user of a template cutting guide model 3236 that would become the preliminary cutting guide model 3238. The selection module 3234 may use the anatomic data 3212 or the bone model 3204 or a combination of these to select a suitable template cutting guide model that would become the preliminary cutting guide model 3238.

In another embodiment, the generator 3232 may facilitate revisions or edits by a user of a generated cutting guide model that will become the preliminary cutting guide model 3238. The selection module 3234 may use the anatomic data 3212 or the bone model 3204 or a combination of these to select a suitable template cutting guide model that would become the preliminary cutting guide model 3238.

The repository 3502 may include any number of, and/or a variety of template cutting guide models 3236. The template cutting guide models 3236 may be distinguished based on a gender or age of the patient, which joint of a midfoot, hind foot, or ankle will be cut, which material will be used for the template cutting guide, and the like. The template cutting guide model 3236 may differ from each other in what degree of deformity correction the template cutting guide model 3236 is designed to provide. In addition, the template cutting guide models 3236 may be distinguished based how one or more features of the template cutting guide model 3236 are positioned, arranged, and/or configured relative to each other. For example in certain template cutting guide models 3236, the number, position, and/or configuration of alignment features 1260_a,b_ and/or bone attachment features (e.g., holes 1240) may vary based on needs or preferences of patients, the nature of the deformity, and/or surgeon preferences.

In certain embodiments, the template cutting guide models 3236 may vary in how the slots 1350,1352 (e.g., guide features, See FIG. 13) for the cuts are positioned, angled, and oriented relative to each other and/or to a longitudinal axis of respective bones at a joint for use with the template cutting guide model 3236. For example in one template cutting guide model 3236 the slot 1352 for a resection of a metatarsal bone may be perpendicular to a longitudinal axis of the metatarsal bone and the slot 1350 may be angled relative to a longitudinal axis of the cuneiform or cuboid bone such that once the two bones are brought together the deformity is corrected. Alternatively, in another template cutting guide model 3236 the slot 1352 for a resection of a metatarsal bone may be angled relative to a longitudinal axis of the metatarsal bone and the slot 1350 may be perpendicular to a longitudinal axis of the cuneiform or cuboid bone such that once the two bones are brought together the deformity is corrected.

The selection module 3234 may be configured to automatically select a template cutting guide model 3236 and/or provide an automatic template cutting guide model 3236 recommendation that can be changed by a user, such as a surgeon. For example, in one embodiment, the provision module 3230 and/or selection module 3234 includes an artificial intelligence or machine learning module. The artificial intelligence or machine learning module is configured to implement one or more of a variety of artificial intelligence modules that may be trained for selecting a template cutting guide model 3236 based on anatomic data 3212 and/or other input parameters. In one embodiment, the artificial intelligence or machine learning module may be trained using a large data set of anatomic data 3212 for suitable template cutting guide models 3236 identified and labeled in the dataset by professionals for use to treat a particular deformity 3226. The artificial intelligence or machine learning module may implement, or use, a neural network configured according to the training such that as the artificial intelligence or machine learning module is able to select a suitable template cutting guide model 3236. The template cutting guide model 3236 selected by the selection module 3234 can become the preliminary cutting guide model 3238.

Figure 36:
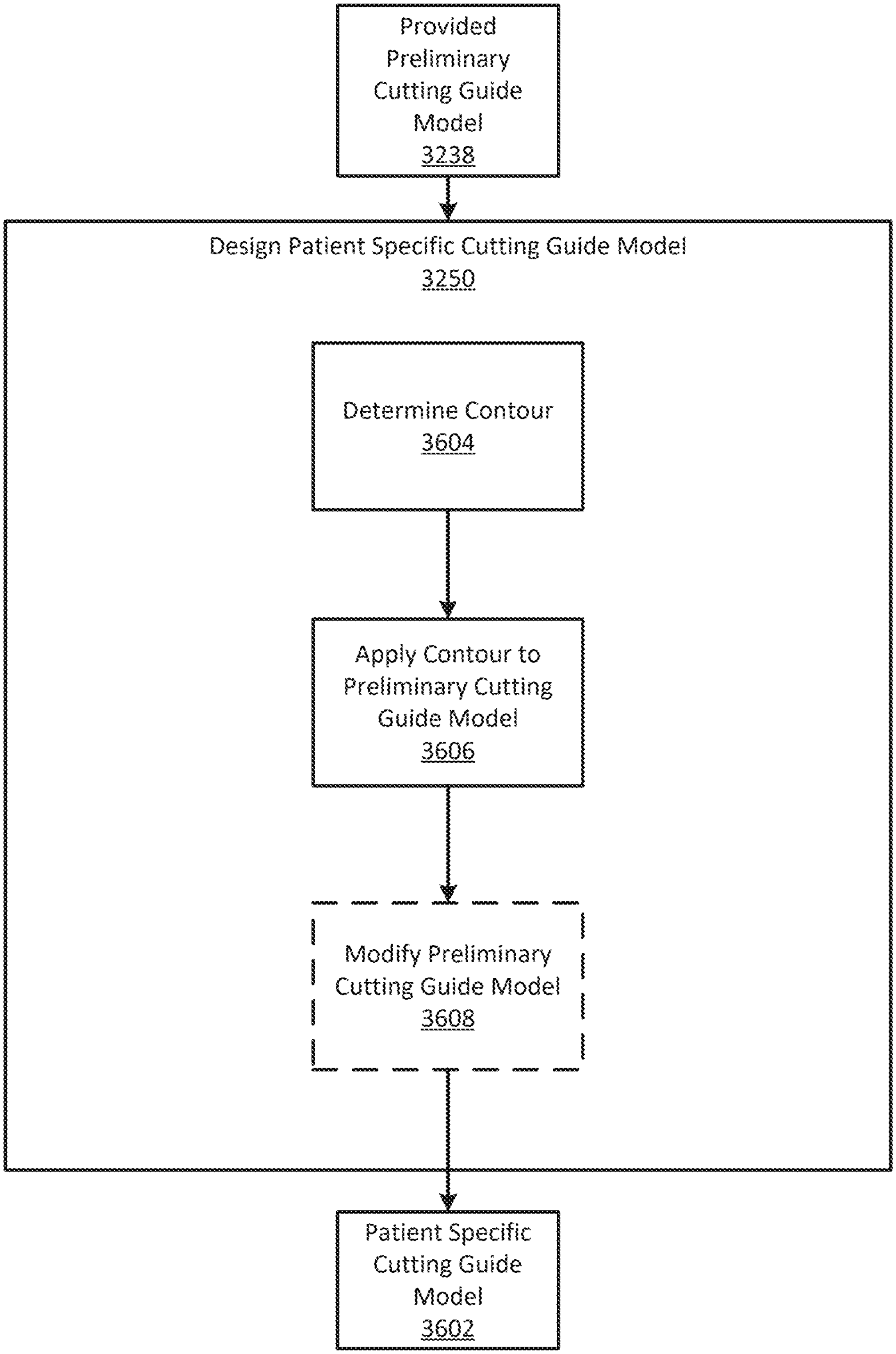
FIG. 36 illustrates an exemplary design module configured to design a patient specific cutting guide model, according to one embodiment.

FIG. 36 illustrates an exemplary design module 3250 configured to design a patient specific cutting guide model, according to one embodiment. The design module 3250 may accept a preliminary cutting guide model 3238 and generate a patient specific cutting guide model 3602. In one embodiment, the design module 3250 includes a contour module 3604, an application module 3606, and/or an optional modification module 3608.

Referring now to FIGS. 3A-3D, and 36, the design module 3250 may modify the preliminary cutting guide model 3238 such that the bone-facing and/or bone-contacting surfaces of the preliminary cutting guide model 3238 match a contour of the surfaces and/or joint of bones of a joint that is to be resected using the preliminary cutting guide model 3238.

The contour module 3604 may determine a contour of the bones that will contact the preliminary cutting guide model 3238. The contour module 3604 may use a bone model 3204 and/or anatomic data 3212 to determine the contour. For example, the contour module 3604 may determine the shapes of the first cuneiform 210 and/or the first metatarsus 230.

The application module 3606 may apply the contour to the provided preliminary cutting guide model 3238 to custom contour a bone apposition side 330 of the preliminary cutting guide model 3238 to match the shapes of the first cuneiform 210 and/or the first metatarsus 230. Applying the contour to the preliminary cutting guide model 3238 may convert the preliminary cutting guide model 3238 to a patient specific cutting guide model 3602.

Generation of the contours of the cuneiform apposition portion 342 and the metatarsus apposition portion 344 of the preliminary cutting guide model 3238 may be performed relative easily in various CAD programs. In some embodiments, the shapes of the corresponding surfaces of the first cuneiform 210 and the first metatarsus 230 may be obtained directly from the bone model 3204, anatomic data 3212, CAD models and/or CT scan data, and simply copied onto the preliminary cutting guide model 3238. Various operations may be used to copy surfaces from one object to another. Additionally or alternatively, various Boolean operations, such as a Boolean subtraction operation, may be used to remove material from a model for the body 310 of the preliminary cutting guide model 3238 with a shape that matches the surfaces of the first cuneiform 210 and the first metatarsus 230.

In certain embodiments, the design module 3250 may include an optional module, such as a modification module 3608. The modification module 3608 may enable a user such as a technician or surgeon to make additional modifications to the design and configuration of the preliminary cutting guide model 3238. In one embodiment, the user can change any of the features, angles, configurations, or parameters of the preliminary cutting guide model 3238. For example, a surgeon may be aware of other concerns or anatomic deformities of a patient, for example on an opposite foot or in connection with a hip or other orthopedic joint which motivate the surgeon to adjust an angle of one of more guide features of the preliminary cutting guide model 3238.

Alternatively, or in addition, a user may use the modification module 3608 to modify a predefined osteotomy procedure. The user may add, remove, or modify steps and the instrumentation used in the osteotomy procedure to create a patient specific osteotomy procedure. In this manner, a user may configure features of a preliminary cutting guide model 3238 or modified preliminary cutting guide model and/or osteotomy procedure specific to a patient specific osteotomy procedure the surgeon is planning for the patient. As used herein, "patient specific osteotomy procedure" refers to an osteotomy procedure that has been adjusted, tailored, modified, or configured to specifically address the needs or desires or a particular patient. In certain aspects, one patient specific osteotomy procedure may be useable in connection with only one patient. In other aspects, one patient specific osteotomy procedure may be useable with a number of patients having a particular class of characteristics.

The user may review the preliminary cutting guide model 3238 and may adjustments or revisions or make no adjustments or revisions. The output of the modification module 3608 and/or the application module 3606 is a patient specific cutting guide model 3602.

Figure 37:
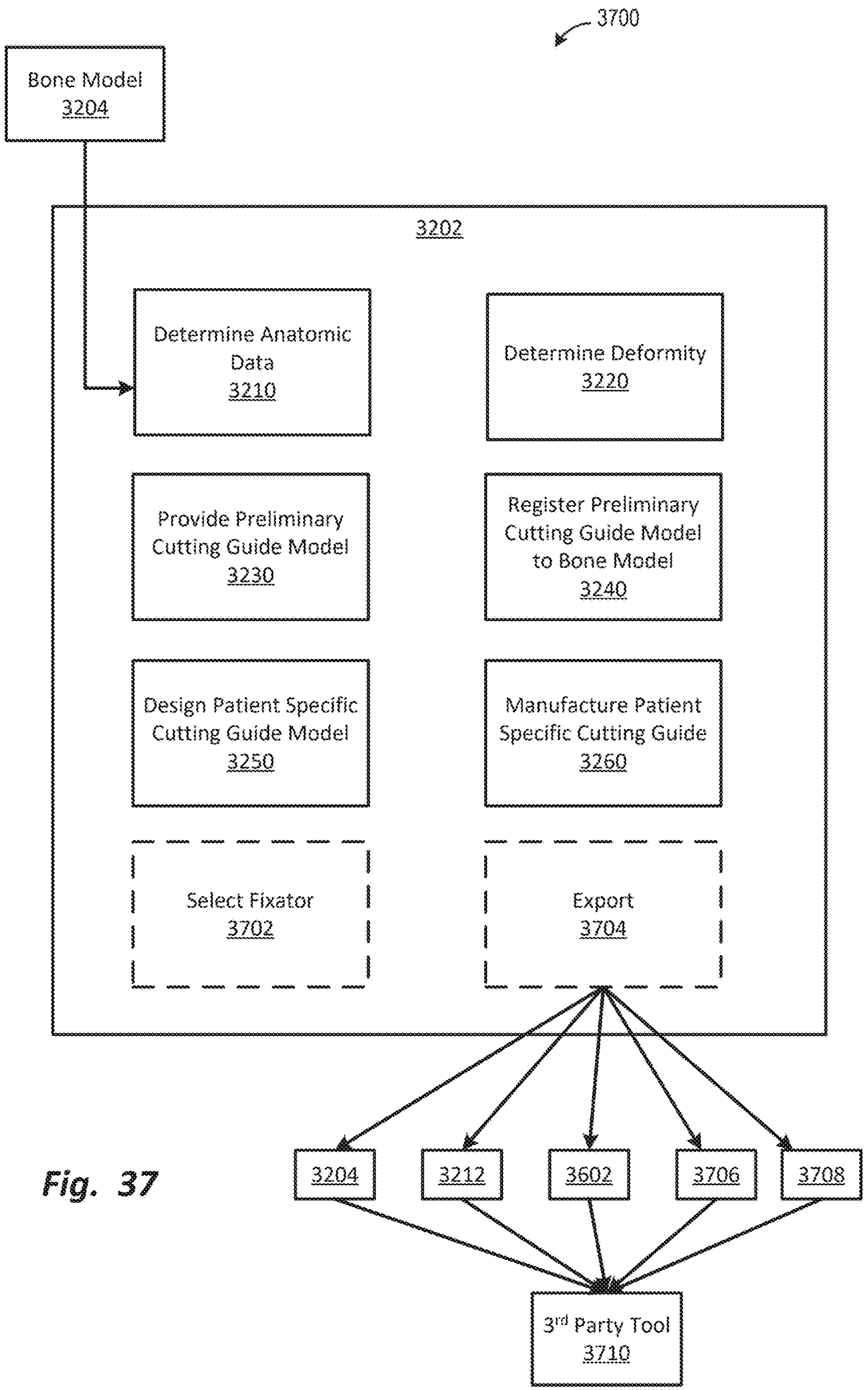
FIG. 37 illustrates an exemplary system configured to generate one or more patient specific instruments configured to correct a bone condition, according to one embodiment.

FIG. 37 illustrates an exemplary system 3700 configured to generate one or more patient specific instruments configured to correct a bone condition, according to one embodiment. The system 3700 may include similar components or modules to those described in relation to FIG. 32. In addition, the system 3700 may include a fixator selector 3702 and/or an export module 3704.

The fixator selector 3702 enables a user to determine which fixator(s) to use for an osteotomy procedure planned for a patient. In one embodiment, the fixator selector 3702 may recommend one or more fixators based on the bone model 3204, the deformity 3226 or input from a user or a history of prior osteotomy procedures performed to correct a particular deformity 3226. In one embodiment, the fixator selector 3702 selects a bone plate for fixation of two bones of the patient during an osteotomy procedure. The fixator selector 3702 may select a fixator model from a set of predefined fixator models or select a physical fixator from a set of fixators. The fixators may include a plate and associated accessories such as screws, anchors, and the like.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

In one embodiment, the fixator selector 3702 includes an artificial intelligence or machine learning module. The artificial intelligence or machine learning module is configured to implement one or more of a variety of artificial intelligence modules that may be trained for selecting fixator(s) based on anatomic data 3212 and/or other input parameters. In one embodiment, the artificial intelligence or machine learning module may be trained using a large data set of anatomic data 3212 for suitable fixator(s) identified and labeled in the dataset by professionals for use to treat a particular deformity 3226. The artificial intelligence or machine learning module may implement, or use, a neural network configured according to the training such that as the artificial intelligence or machine learning module is able to select or recommend suitable fixator(s).

The export module 3704 is configured to enable exporting of a patient specific cutting guide model 3602 for a variety of purposes including, but not limited to, fabrication/manufacture of a patient specific cutting guide 3206 and/or fixator(s), generation of a preoperative plan, generation of a physical bone model matching the bone model 3204, and the like. In one embodiment, the export module 3704 is configured to export the bone model 3204, anatomic data 3212, a patient specific cutting guide model 3602, a preoperative plan 3706, a fixator model 3708, or the like. In this manner the custom instrumentation and/or procedural steps for an osteotomy procedure can be used in other tools. The preoperative plan 3706 may include a set of step by step instructions or recommendation for a surgeon or other staff in performing an osteotomy procedure such as patient specific osteotomy procedure. The preoperative plan 3706 may include images and text instructions and may include identification of instrumentation to be used for different steps of the osteotomy procedure. The instrumentation may include the patient specific cutting guide 3206 and/or one or more fixators. In one embodiment, the export module 3704 may provide a fixator model which can be used to fabricate a fixator for the osteotomy procedure.

The exports (3204, 3212, 3602, 3706, and 3708) may be inputs for a variety of 3$^{rd}$ party tools 3710 including a manufacturing tool, a simulation tool, a virtual reality tool, an augmented reality tool, an operative procedure simulation tool, a robotic assistance tool, and the like. A surgeon can then use these tools when performing an osteotomy procedure or for rehearsals and preparation for the osteotomy procedure. For example, a physical model of the bones, patient specific cutting guide 3206, and/or fixators can be fabricated, and these can be used for a rehearsal operative procedure. Alternatively, a surgeon can use the bone model 3204, preliminary cutting guide model 3238, and/or a fixator model to perform a simulated osteotomy procedure using an operative procedure simulation tool.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. A method for remediating a condition present in a patient's foot, the method comprising:
- receiving anatomic data for a patient's foot to an artificial intelligence module, the artificial intelligence module determining a preliminary cutting guide configured to correct a deformity identified by the anatomic data; and
- providing the preliminary cutting guide configured to define a cutting guide to remediate a bunion deformity in a patient's foot.

2. The method of claim 1, wherein the anatomic data identifies the bunion deformity and the method further comprises generating a cutting guide based on the preliminary cutting guide, the cutting guide configured to remediate the deformity.

3. The method of claim 2, wherein generating the cutting guide comprises manufacturing a patient-specific cutting guide based on the preliminary cutting guide.

4. The method of claim 1, further comprising:
- providing the anatomic data of the patient's foot to the artificial intelligence module; and
- determining the deformity by the artificial intelligence module based on at least one of the anatomic data, a bone model, and a Computer Aided Design (CAD) model.

5. The method of claim 4, further comprising providing a plurality of input parameters to the artificial intelligence module, the artificial intelligence module configured to use the input parameters to determine the deformity.

6. The method of claim 1, wherein determining the preliminary cutting guide comprises the artificial intelligence module generating a preliminary cutting guide model.

7. The method of claim 1, wherein determining the preliminary cutting guide comprises the artificial intelligence module selecting the preliminary cutting guide from a set of template cutting guide.

8. The method of claim 2, further comprising the artificial intelligence module determining at least one fixator to use in an osteotomy procedure planned for the patient's foot and wherein the osteotomy procedure comprises the cutting guide configured to remediate the bunion deformity present in a patient's foot.

9. A method for remediating a condition present in a patient's foot, the method comprising:
- determining, by an artificial intelligence module, a bunion deformity between a first metatarsal and a second metatarsal of a patient's foot, the determined bunion deformity based on at least one of anatomic data, a bone model, and a Computer Aided Design (CAD) model;

providing the determined bunion deformity to an artificial intelligence module;

selecting, by an artificial intelligence module, a preliminary cutting from a set of template cutting guide models, the preliminary cutting configured to correct the determined bunion deformity; and generating a cutting guide based on the selected preliminary cutting guide.

10. The method of claim 9, wherein the bone comprises a bone model of at least the first metatarsal and the second metatarsal of the patient's foot.

11. The method of claim 9, wherein generating the cutting guide comprises modifying the selected the preliminary cutting guide to form a patient-specific cutting guide that is used to generate the cutting guide.

12. The method of claim 9, wherein generating the cutting guide comprises manufacturing a patient-specific cutting guide based on the selected the preliminary cutting guide.

13. The method of claim 9, wherein generating the cutting guide comprises:

determining a contour of bones that will contact the preliminary cutting guide, the contour based on at least one of a bone model of the bones and anatomic data of the patient;

applying the contour to the selected preliminary cutting guide to contour a bone apposition side of the selected preliminary cutting guide.

14. The method of claim 13, further comprising modifying the selected preliminary cutting guide to include one or more modifications provided by a user.

15. The method of claim 9, further comprising an artificial intelligence module determining at least one fixator to use in an osteotomy procedure planned for the patient's foot and wherein the osteotomy procedure comprises the cutting guide configured to remediate a condition present in a patient's foot.

16. A non-transitory computer-readable medium storing a set of instructions for remediating a condition present in a patient's foot, the set of instructions comprising:

one or more instructions that, when executed by one or more processors of a device, cause the device to:

determine, by an artificial intelligence module, a bunion deformity of a first metatarsal in relation to a second metatarsal of a patient's foot, the determined bunion deformity based on a bone model comprising bone models of at least the first metatarsal and the second metatarsal of the patient's foot;

provide the determined bunion deformity to the artificial intelligence module;

select, by the artificial intelligence module, a preliminary cutting guide model from a set of template cutting guide models, the preliminary cutting guide model configured to correct the determined bunion deformity of the first metatarsal in relation to the second metatarsal; and generate a cutting guide based on the selected preliminary cutting guide model.

17. The non-transitory computer-readable medium of claim 16, wherein the one or more instructions that cause the device to generate the cutting guide, cause the device to modify the selected the preliminary cutting guide model to form a patient-specific cutting guide model that is used to generate the cutting guide.

18. The non-transitory computer-readable medium of claim 16, wherein the one or more instructions that cause the device to generate the cutting guide, cause the device to manufacture a patient-specific cutting guide based on the selected preliminary cutting guide model.

19. The non-transitory computer-readable medium of claim 16, wherein the one or more instructions, when generating the cutting guide, cause the device to:

determine a contour of bones of the patient that will contact the preliminary cutting guide model, the contour based on the bone model; and apply the contour to the selected preliminary cutting guide model to contour a bone apposition side of the selected preliminary cutting guide model.

20. The non-transitory computer-readable medium of claim 19, wherein the one or more instructions further cause the device to:

modify the selected preliminary cutting guide model to include one or more modifications provided by a user.

* * * * *